(12) United States Patent
Mackay et al.

(10) Patent No.: US 10,940,212 B2
(45) Date of Patent: Mar. 9, 2021

(54) IL-21 AGONIST ANTIBODIES AND METHODS OF TREATMENT USING SAME

(71) Applicant: Monash University, Clayton (AU)

(72) Inventors: Charles Reay Mackay, Clayton (AU); Di Yu, Clayton (AU); Remy Robert, Clayton (AU)

(73) Assignee: MONASH UNIVERSITY, Clayton (AU)

( * ) Notice: Subject to any disclaimer, the term of this patent is extended or adjusted under 35 U.S.C. 154(b) by 273 days.

(21) Appl. No.: 15/537,095

(22) PCT Filed: Dec. 18, 2015

(86) PCT No.: PCT/AU2015/050814
§ 371 (c)(1),
(2) Date: Jun. 16, 2017

(87) PCT Pub. No.: WO2016/094962
PCT Pub. Date: Jun. 23, 2016

(65) Prior Publication Data
US 2019/0111148 A1 Apr. 18, 2019

(30) Foreign Application Priority Data
Dec. 19, 2014 (AU) .............................. 2014905159

(51) Int. Cl.
*A61K 39/395* (2006.01)
*A61K 47/68* (2017.01)
*C07K 16/24* (2006.01)
*A61K 38/20* (2006.01)
*A61K 39/00* (2006.01)

(52) U.S. Cl.
CPC .......... *A61K 47/6813* (2017.08); *A61K 38/20* (2013.01); *A61K 47/6845* (2017.08); *C07K 16/244* (2013.01); *A61K 2039/505* (2013.01); *C07K 2317/24* (2013.01); *C07K 2317/33* (2013.01); *C07K 2317/34* (2013.01); *C07K 2317/74* (2013.01); *C07K 2317/75* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 6,309,636 | B1 | 10/2001 | Do Couto | |
|---|---|---|---|---|
| 2005/0215770 | A1* | 9/2005 | Bell | C07K 16/28 530/388.22 |
| 2009/0130102 | A1* | 5/2009 | Weaver | C07K 16/00 424/133.1 |
| 2009/0191214 | A1 | 7/2009 | Jaspers | |
| 2012/0225065 | A1 | 9/2012 | Jaspers | |

FOREIGN PATENT DOCUMENTS

| WO | 05/112983 A2 | 12/2005 |
|---|---|---|
| WO | 06/057027 A1 | 6/2006 |
| WO | 06/105538 A2 | 10/2006 |
| WO | 2007111714 A2 | 10/2007 |
| WO | 08/112543 A2 | 9/2008 |
| WO | 09/100035 A2 | 8/2009 |
| WO | 2010055366 A2 | 5/2010 |
| WO | 14/205501 A1 | 12/2014 |

OTHER PUBLICATIONS

Leong et al., "112: The mechanism and application of a superagonistic antibody for human IL-21", Cytokine, 70(1):54 (2014).
Mackay et al., "A super-agonist monoclonal antibody to human IL-21 and its application in immunomodulation", Internet, http://www.flintbox.com/public/project/24071, posted Sep. 19, 2013, retrieved Feb. 26, 2016 (abstract only).
Spolski et al., "The Yin and Yang of Interleukin-21 in Allergy, Autoimmunity and Cancer", Current Opinion in Immunology, 20(3):295-301 (2008).
Vogelzang et al., "A Fundamental Role for Interleukin-21 in the Generation of T Follicular Helper Cells", Immunity, 29:127-137 (2008).
Written Opinion for PCT application No. PCT/AU14/000673, dated Aug. 8, 2014.
European Search Report for European application No. 14817437.8 dated Dec. 22, 2016.
Sondergaard et al: "IL-21: roles in immunopathology and cancer therapy". Tissue Antigens. vol. 74. No. 6. Dec. 1, 2009 (Dec. 1, 2009). pp. 467-479.
Carter P J: "Potent Antibody Therapeutics by design". Nature Reviews Immunology. vol. 6. Apr. 7, 2006 (Apr. 7, 2006). pp. 343-357.
Gershoni et a. "Epitope mapping—The first step in developing epitope-based vaccines" Biodrugs. vol. 21. No. 3. Jan. 1, 2007 (Jan. 1, 2007). pp. 145-156.
Smyth et al: "Interleukin 21 Enhances Antibody-Mediated Tumor Rejection". Cancer Research. vol. 68. No. 8. Apr. 15, 2008 (Apr. 15, 2008). pp. 3019-3025.
Sondergaard et al., "Interleukin 21 therapy increases the density of tumor infiltrating CD8+ T cells and inhibits the growth of syngeneic tumors", Cancer Immunol. Immunother, 56:1417-1428 (2007).
BioLegend 2012-2013 Catalog and Reference Material, p. 415 (2012)—Antibody clone 2B2-G20 has a VH and VL amino acid sequence of SEQ ID No. 2 and 3, respectively. Each of SEQ ID No. 2 and 3 are as described in the instant application (U.S. Appl. No. 15/537,095).
Topalian et al, "Safety, Activity, and Immune Correlate of Anti-PD-1 Antibody in Cancer", The New England Journal of Medicine, vol. 366, No. 26, pp. 2443-2454, Jun. 28, 2012.

\* cited by examiner

*Primary Examiner* — Dong Jiang
(74) *Attorney, Agent, or Firm* — DLA Piper LLP

(57) ABSTRACT

The invention relates to IL-21, to antibodies and related fragments thereof for binding to IL-21, to production of said antibodies and fragments and to use of said antibodies and fragments for detection and therapy of various conditions, in particular inflammation, infection and oncology.

8 Claims, 16 Drawing Sheets

Specification includes a Sequence Listing.

Figure 2

Heavy chain

EVQLQQSGADLVRSGASVKLSCTASGFNIK DYYIH WVKQRPEQGLELIG WIDPESGDTEYAPKFQV
                                CDR1                                     CDR2

KATMTADTSSNTAYLQLSSLTSEDTAVYYCND GSGY WGQGTTLTVSS
                                  CDR3

Light chain

DVVMTQTPLTLSVTLGQPASISC KSSQSLLDSDGETYLN WLLQRPGQSPKRLIS LVSKLDS
                       CDR1                                    CDR2

GVPDRFTGSGSGTDFTLKISRVEAEDLGVYYC WQGTHFPYT FGGGTKLEIK
                                            CDR

Figure 9

Human IL-21

| Secretion signal peptide | Helix A | Loop AB | He |
|---|---|---|---|

MRSSPGNMERIVICLMVIFLGTLVHKSSSQGQDRHMIRMRQLIDIVDQLKNYVNDLVPEFLPAPEDVETNCEWSA

| llx B | Loop BC | Helix C | Loop CD | Helix D |
|---|---|---|---|---|

FSCFQKAQLKSANTGNNERIINVSIKKLKRKPPSTNAGRRQKHRLTCPSCDSYEKKPPKEFLERFKSLLQKMIHQHLS

SRTHGSEDS

Peptide 1 (P1, 30aa): FLPAPEDVETNCEWSAFSCF*QK*AQLKSANT

Peptide 2 (P2, 27aa): AQLKSANTGNNERIINVS*IKKLKRK*PP

Peptide 3 (P3, 30aa): *IKKLKRK*PPSTNAGRRQKHRLT*CPSCD*SYE

Peptide 4 (P4, 23aa): PPSTNAGRRQKHRLT*CPSCD*SYE

Peptide 5 (P5, 15aa): PPSTNAGRRQKHRLT

Peptide 1 (P1, 30aa): FLPAPEDVETNCEWSAFSCFQKAQLKSANT    No binding

Peptide 2 (P2, AQLKSANTGNNERIINVSIKKLKRKPP    Strongest

Peptide 3 (P3, 30aa): IKKLKRKPPSTNAGRRQKHRLT*CPSCD*SYE    weaker

Peptide 4 (P4, 23aa): PP*STNAGRRQ*KHRLT*CPSCD*SY    weakest

Peptide 5 (P5, 15aa): PP*STNAGRRQ*KHRLT    No binding

Refined epitope of 2P2: **IK*KLKRK*PP*STNAGRRQ*KHRLT*CPSCD*SYE**

Figure 12
A
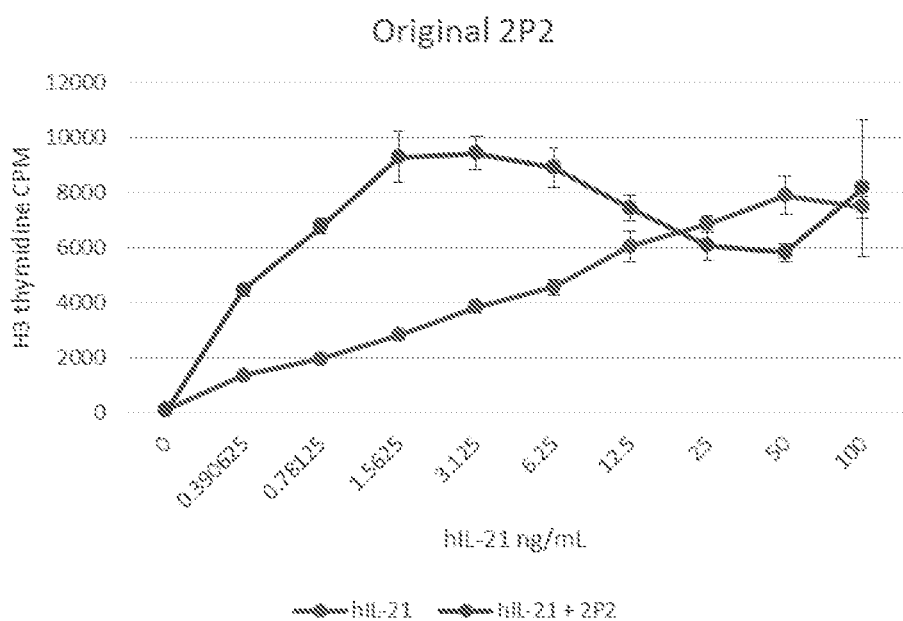
B
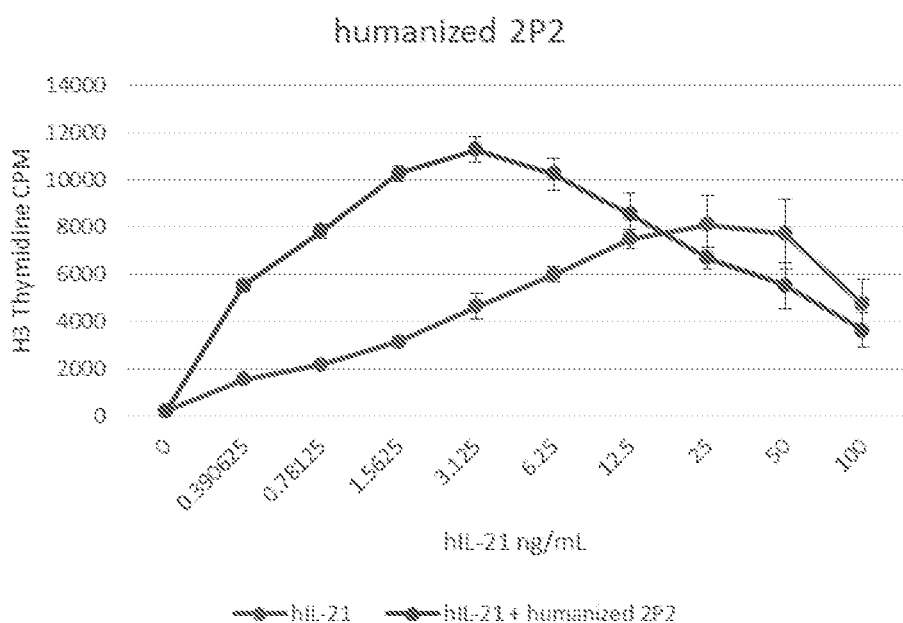

SEQUENCE LISTING

```
<160> NUMBER OF SEQ ID NOS: 42

<210> SEQ ID NO 1
<211> LENGTH: 155
<212> TYPE: PRT
<213> ORGANISM: Artificial Sequence
<220> FEATURE:
<223> OTHER INFORMATION: core amino acid sequence of 2P2 binding epitope

<400> SEQUENCE: 1

Met Glu Arg Ile Val Ile Cys Leu Met Val Ile Phe Leu Gly Thr Leu
1               5                   10                  15

Val His Lys Ser Ser Gln Gly Gln Asp Arg His Met Ile Arg Met
            20                  25                  30

Arg Gln Leu Ile Asp Ile Val Asp Gln Leu Lys Asn Tyr Val Asn Asp
            35                  40                  45

Leu Val Pro Glu Phe Leu Pro Ala Pro Glu Asp Val Glu Thr Asn Cys
    50                  55                  60

Glu Trp Ser Ala Phe Ser Cys Phe Gln Lys Ala Gln Leu Lys Ser Ala
65                  70                  75                  80

Asn Thr Gly Asn Asn Glu Arg Ile Ile Asn Val Ser Ile Lys Lys Leu
                85                  90                  95

Lys Arg Lys Pro Pro Ser Thr Asn Ala Gly Arg Arg Gln Lys His Arg
            100                 105                 110

Leu Thr Cys Pro Ser Cys Asp Ser Tyr Glu Lys Lys Pro Pro Lys Glu
            115                 120                 125

Phe Leu Glu Arg Phe Lys Ser Leu Leu Gln Lys Met Ile His Gln His
        130                 135                 140

Leu Ser Ser Arg Thr His Gly Ser Glu Asp Ser
145                 150                 155

<210> SEQ ID NO 2
<211> LENGTH: 113
<212> TYPE: PRT
<213> ORGANISM: Artificial Sequence
<220> FEATURE:
<223> OTHER INFORMATION: amino acid sequence of VH chain of antibody 2P2

<400> SEQUENCE: 2

Glu Val Gln Leu Gln Gln Ser Gly Ala Asp Leu Val Arg Ser Gly Ala
1               5                   10                  15

Ser Val Lys Leu Ser Cys Thr Ala Ser Gly Phe Asn Ile Lys Asp Tyr
            20                  25                  30
```

```
Tyr Ile His Trp Val Lys Gln Arg Pro Glu Gln Gly Leu Glu Leu Ile
            35                  40                  45

Gly Trp Ile Asp Pro Glu Ser Gly Asp Thr Glu Tyr Ala Pro Lys Phe
 50                  55                  60

Gln Val Lys Ala Thr Met Thr Ala Asp Thr Ser Ser Asn Thr Ala Tyr
 65                  70                  75                  80

Leu Gln Leu Ser Ser Leu Thr Ser Glu Asp Thr Ala Val Tyr Tyr Cys
                85                  90                  95

Asn Asp Gly Ser Gly Tyr Trp Gly Gln Gly Thr Thr Leu Thr Val Ser
               100                 105                 110

Ser
```

```
<210> SEQ ID NO 3
<211> LENGTH: 112
<212> TYPE: PRT
<213> ORGANISM: Artificial Sequence
<220> FEATURE:
<223> OTHER INFORMATION: amino acid sequence of VL chain of antibody 2P2

<400> SEQUENCE: 3

Asp Val Val Met Thr Gln Thr Pro Leu Thr Leu Ser Val Thr Leu Gly
 1               5                  10                  15

Gln Pro Ala Ser Ile Ser Cys Lys Ser Ser Gln Ser Leu Leu Asp Ser
                20                  25                  30

Asp Gly Glu Thr Tyr Leu Asn Trp Leu Leu Gln Arg Pro Gly Gln Ser
            35                  40                  45

Pro Lys Arg Leu Ile Ser Leu Val Ser Lys Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
                85                  90                  95

Thr His Phe Pro Tyr Thr Phe Gly Gly Gly Thr Lys Leu Glu Ile Lys
               100                 105                 110
```

```
<210> SEQ ID NO 4
<211> LENGTH: 30
<212> TYPE: PRT
<213> ORGANISM: Artificial Sequence
<220> FEATURE:
<223> OTHER INFORMATION: amino acid sequence of 2P2 binding epitope

<400> SEQUENCE: 4

Ile Lys Lys Leu Lys Arg Lys Pro Pro Ser Thr Asn Ala Gly Arg Arg
 1               5                  10                  15

Gln Lys His Arg Leu Thr Cys Pro Ser Cys Asp Ser Tyr Glu
                20                  25                  30
```

```
<210> SEQ ID NO 5
<211> LENGTH: 8
<212> TYPE: PRT
<213> ORGANISM: Artificial Sequence
<220> FEATURE:
<223> OTHER INFORMATION: amino acid sequence of CDR1 of VH chain of
      antibody 2P2 using IMGT numbering scheme

<400> SEQUENCE: 5

Gly Phe Asn Ile Lys Asp Tyr Tyr
 1               5
```

```
<210> SEQ ID NO 6
<211> LENGTH: 8
<212> TYPE: PRT
<213> ORGANISM: Artificial Sequence
<220> FEATURE:
<223> OTHER INFORMATION: amino acid sequence of CDR2 of VH chain of
      antibody 2P2 using IMGT numbering scheme

<400> SEQUENCE: 6

Ile Asp Pro Glu Ser Gly Asp Thr
1               5

<210> SEQ ID NO 7
<211> LENGTH: 6
<212> TYPE: PRT
<213> ORGANISM: Artificial Sequence
<220> FEATURE:
<223> OTHER INFORMATION: amino acid sequence of CDR3 of VH chain of
      antibody 2P2 using IMGT numbering scheme

<400> SEQUENCE: 7

Asn Asp Gly Ser Gly Tyr
1               5

<210> SEQ ID NO 8
<211> LENGTH: 11
<212> TYPE: PRT
<213> ORGANISM: Artificial Sequence
<220> FEATURE:
<223> OTHER INFORMATION: amino acid sequence of CDR1 of VL chain of
      antibody 2P2 using IMGT numbering scheme

<400> SEQUENCE: 8

Gln Ser Leu Leu Asp Ser Asp Gly Glu Thr Tyr
1               5                   10

<210> SEQ ID NO 9
<211> LENGTH: 3
<212> TYPE: PRT
<213> ORGANISM: Artificial Sequence
<220> FEATURE:
<223> OTHER INFORMATION: amino acid sequence of CDR2 of VL chain of
      antibody 2P2 using IMGT numbering scheme

<400> SEQUENCE: 9

Leu Val Ser
1

<210> SEQ ID NO 10
<211> LENGTH: 9
<212> TYPE: PRT
<213> ORGANISM: Artificial Sequence
<220> FEATURE:
<223> OTHER INFORMATION: amino acid sequence of CDR3 of VL chain of
      antibody 2P2 using IMGT numbering scheme

<400> SEQUENCE: 10

Trp Gln Gly Thr His Phe Pro Tyr Thr
1               5

<210> SEQ ID NO 11
<211> LENGTH: 5
<212> TYPE: PRT
<213> ORGANISM: Artificial Sequence
<220> FEATURE:
<223> OTHER INFORMATION: amino acid sequence of CDR1 of VH chain of
      antibody 2P2

<400> SEQUENCE: 11
```

Asp Tyr Tyr Ile His
1               5

<210> SEQ ID NO 12
<211> LENGTH: 17
<212> TYPE: PRT
<213> ORGANISM: Artificial Sequence
<220> FEATURE:
<223> OTHER INFORMATION: amino acid sequence of CDR2 of VH chain of
      antibody 2P2

<400> SEQUENCE: 12

Trp Ile Asp Pro Glu Ser Gly Asp Thr Glu Tyr Ala Pro Lys Phe Gln
1               5                   10                  15
Val

<210> SEQ ID NO 13
<211> LENGTH: 4
<212> TYPE: PRT
<213> ORGANISM: Artificial Sequence
<220> FEATURE:
<223> OTHER INFORMATION: amino acid sequence of CDR3 of VH chain of
      antibody 2P2

<400> SEQUENCE: 13

Gly Ser Gly Tyr
1

<210> SEQ ID NO 14
<211> LENGTH: 16
<212> TYPE: PRT
<213> ORGANISM: Artificial Sequence
<220> FEATURE:
<223> OTHER INFORMATION: amino acid sequence of CDR1 of VL chain of
      antibody 2P2

<400> SEQUENCE: 14

Lys Ser Ser Gln Ser Leu Leu Asp Ser Asp Gly Glu Thr Tyr Leu Asn
1               5                   10                  15

<210> SEQ ID NO 15
<211> LENGTH: 7
<212> TYPE: PRT
<213> ORGANISM: Artificial Sequence
<220> FEATURE:
<223> OTHER INFORMATION: acid sequence of CDR2 of VL chain of antibody
      2P2

<400> SEQUENCE: 15

Leu Val Ser Lys Leu Asp Ser
1               5

<210> SEQ ID NO 16
<211> LENGTH: 9
<212> TYPE: PRT
<213> ORGANISM: Artificial Sequence
<220> FEATURE:
<223> OTHER INFORMATION: amino acid sequence of CDR3 of VL chain of
      antibody 2P2

<400> SEQUENCE: 16

Trp Gln Gly Thr His Phe Pro Tyr Thr
1               5

<210> SEQ ID NO 17
<211> LENGTH: 339

```
<212> TYPE: DNA
<213> ORGANISM: Artificial Sequence
<220> FEATURE:
<223> OTHER INFORMATION: nucleotide sequence encoding the VH chain of
      antibody 2P2

<400> SEQUENCE: 17
gaggttcagc tgcagcagtc tggggcagac cttgtgaggt caggggcctc agtcaagttg    60
tcctgcacag cttctggctt caacattaaa gactactata tacactgggt gaagcagagg   120
cctgaacagg gcctggagtt gattggatgg attgatcctg agagtggtga tactgaatat   180
gccccgaagt ccaggtcaa ggccactatg actgcagaca catcctccaa tacagcctac    240
ctgcagctca gcagcctgac atctgaggac actgccgtct attactgtaa tgacggtagt   300
ggttactggg gccaaggcac cactctcaca gtctcctca                          339

<210> SEQ ID NO 18
<211> LENGTH: 339
<212> TYPE: DNA
<213> ORGANISM: Artificial Sequence
<220> FEATURE:
<223> OTHER INFORMATION: nucleotide sequence encoding the VL chain of
      antibody 2P2

<400> SEQUENCE: 18
gatgttgtga tgacccagac tccactcact ttgtcggtta cccttggaca accagcctcc    60
atctcttgca gtcaagtca gagcctctta gatagtgatg gagagacata tttgaattgg    120
ttgctacaga ggccaggcca gtctccaaag cgcctcatct ctctggtgtc taaactggac   180
tctggagtcc ctgacaggtt cactggcagt ggatcaggga cagatttcac actgaaaatc   240
agcagagtgg aggctgagga tttgggagtt tattattgct ggcaaggtac acattttccg   300
tacacattcg gaggggggac caagctggaa ataaaacgc                          339

<210> SEQ ID NO 19
<211> LENGTH: 30
<212> TYPE: PRT
<213> ORGANISM: Artificial Sequence
<220> FEATURE:
<223> OTHER INFORMATION: Amino Acid Sequence of 2P2 binding epitope

<400> SEQUENCE: 19

Phe Leu Pro Ala Pro Glu Asp Val Glu Thr Asn Cys Glu Trp Ser Ala
1               5                   10                  15

Phe Ser Cys Phe Gln Lys Ala Gln Leu Lys Ser Ala Asn Thr
            20                  25                  30

<210> SEQ ID NO 20
<211> LENGTH: 27
<212> TYPE: PRT
<213> ORGANISM: Artificial Sequence
<220> FEATURE:
<223> OTHER INFORMATION: Amino Acid Sequence of 2P2 binding epitope

<400> SEQUENCE: 20

Ala Gln Leu Lys Ser Ala Asn Thr Gly Asn Asn Glu Arg Ile Ile Asn
1               5                   10                  15

Val Ser Ile Lys Lys Leu Lys Arg Lys Pro Pro
            20                  25

<210> SEQ ID NO 21
<211> LENGTH: 23
<212> TYPE: PRT
```

```
<213> ORGANISM: Artificial Sequence
<220> FEATURE:
<223> OTHER INFORMATION: Amino Acid Sequence of 2P2 binding epitope

<400> SEQUENCE: 21

Pro Pro Ser Thr Asn Ala Gly Arg Arg Gln Lys His Arg Leu Thr Cys
1               5                   10                  15

Pro Ser Cys Asp Ser Tyr Glu
            20

<210> SEQ ID NO 22
<211> LENGTH: 15
<212> TYPE: PRT
<213> ORGANISM: Artificial Sequence
<220> FEATURE:
<223> OTHER INFORMATION: amino acid sequence of 2P2 binding epitope

<400> SEQUENCE: 22

Pro Pro Ser Thr Asn Ala Gly Arg Arg Gln Lys His Arg Leu Thr
1               5                   10                  15

<210> SEQ ID NO 23
<211> LENGTH: 9
<212> TYPE: PRT
<213> ORGANISM: Artificial Sequence
<220> FEATURE:
<223> OTHER INFORMATION: core amino acid sequence of 2P2 binding epitope

<400> SEQUENCE: 23

Ser Thr Asn Ala Gly Arg Arg Gln Lys
1               5

<210> SEQ ID NO 24
<211> LENGTH: 25
<212> TYPE: PRT
<213> ORGANISM: Artificial Sequence
<220> FEATURE:
<223> OTHER INFORMATION: amino acid sequence of FR1 of VH of h2P2 using
      IMGT numbering scheme

<400> SEQUENCE: 24

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 25
<211> LENGTH: 17
<212> TYPE: PRT
<213> ORGANISM: Artificial Sequence
<220> FEATURE:
<223> OTHER INFORMATION: amino acid sequence of FR2 of VH of h2P2 using
      IMGT numbering scheme

<400> SEQUENCE: 25

Ile His Trp Val Arg Gln Ala Pro Gly Gln Gly Leu Glu Leu Ile Gly
1               5                   10                  15

Trp

<210> SEQ ID NO 26
<211> LENGTH: 38
<212> TYPE: PRT
<213> ORGANISM: Artificial Sequence
<220> FEATURE:
<223> OTHER INFORMATION: amino acid sequence of FR3 of VH of h2P2 using
      IMGT numbering scheme
```

```
<400> SEQUENCE: 26

Asn Tyr Ala Gln Lys Phe Gln Val Lys Ala Thr Met Thr Arg Asp Thr
1               5                   10                  15

Ser Ile Ser Thr Ala Tyr Met Glu Leu Ser Arg Leu Arg Ser Asp Asp
            20                  25                  30

Thr Ala Val Tyr Tyr Cys
        35

<210> SEQ ID NO 27
<211> LENGTH: 11
<212> TYPE: PRT
<213> ORGANISM: Artificial Sequence
<220> FEATURE:
<223> OTHER INFORMATION: amino acid sequence of FR4 of VH of h2P2 using
      IMGT numbering scheme

<400> SEQUENCE: 27

Trp Gly Gln Gly Thr Thr Val Thr Val Ser Ser
1               5                   10

<210> SEQ ID NO 28
<211> LENGTH: 26
<212> TYPE: PRT
<213> ORGANISM: Artificial Sequence
<220> FEATURE:
<223> OTHER INFORMATION: amino acid sequence of FR1 of VL of h2P2 using
      IMGT numbering scheme

<400> SEQUENCE: 28

Asp Val Val Met Thr Gln Ser Pro Leu Ser Leu Pro Val Thr Leu Gly
1               5                   10                  15

Gln Pro Ala Ser Ile Ser Cys Lys Ser Ser
            20                  25

<210> SEQ ID NO 29
<211> LENGTH: 17
<212> TYPE: PRT
<213> ORGANISM: Artificial Sequence
<220> FEATURE:
<223> OTHER INFORMATION: amino acid sequence of FR2 of VL of h2P2 using
      IMGT numbering scheme

<400> SEQUENCE: 29

Leu Asn Trp Leu Gln Gln Arg Pro Gly Gln Ser Pro Arg Arg Leu Ile
1               5                   10                  15

Ser

<210> SEQ ID NO 30
<211> LENGTH: 36
<212> TYPE: PRT
<213> ORGANISM: Artificial Sequence
<220> FEATURE:
<223> OTHER INFORMATION: amino acid sequence of FR3 of VL of h2P2 using
      IMGT numbering scheme

<400> SEQUENCE: 30

Lys Leu Asp Ser Gly Val Pro Asp Arg Phe Ser Gly Ser Gly Ser Gly
1               5                   10                  15

Thr Asp Phe Thr Leu Lys Ile Ser Arg Val Glu Ala Glu Asp Val Gly
            20                  25                  30

Val Tyr Tyr Cys
        35
```

<210> SEQ ID NO 31
<211> LENGTH: 10
<212> TYPE: PRT
<213> ORGANISM: Artificial Sequence
<220> FEATURE:
<223> OTHER INFORMATION: amino acid sequence of FR4 of VL of h2P2 using
      IMGT numbering scheme

<400> SEQUENCE: 31

Phe Gly Gln Gly Thr Lys Leu Glu Ile Lys
1               5                   10

<210> SEQ ID NO 32
<211> LENGTH: 30
<212> TYPE: PRT
<213> ORGANISM: Artificial Sequence
<220> FEATURE:
<223> OTHER INFORMATION: amino acid sequence of FR1 of VH of h2P2 using
      Kabat numbering scheme

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys
            20                  25                  30

<210> SEQ ID NO 33
<211> LENGTH: 14
<212> TYPE: PRT
<213> ORGANISM: Artificial Sequence
<220> FEATURE:
<223> OTHER INFORMATION: amino acid sequence of FR2 of VH of h2P2 using
      Kabat numbering scheme

<400> SEQUENCE: 33

Trp Val Arg Gln Ala Pro Gly Gln Gly Leu Glu Leu Ile Gly
1               5                   10

<210> SEQ ID NO 34
<211> LENGTH: 32
<212> TYPE: PRT
<213> ORGANISM: Artificial Sequence
<220> FEATURE:
<223> OTHER INFORMATION: amino acid sequence of FR3 of VH of h2P2 using
      Kabat numbering scheme

<400> SEQUENCE: 34

Lys Ala Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Asn Asp
            20                  25                  30

<210> SEQ ID NO 35
<211> LENGTH: 11
<212> TYPE: PRT
<213> ORGANISM: Artificial Sequence
<220> FEATURE:
<223> OTHER INFORMATION: amino acid sequence of FR4 of VH of h2P2 using
      Kabat numbering scheme

<400> SEQUENCE: 35

Trp Gly Gln Gly Thr Thr Val Thr Val Ser Ser
1               5                   10

<210> SEQ ID NO 36
<211> LENGTH: 23

```
<212> TYPE: PRT
<213> ORGANISM: Artificial Sequence
<220> FEATURE:
<223> OTHER INFORMATION: amino acid sequence of FR1 of VL of h2P2 using
      Kabat numbering scheme

<400> SEQUENCE: 36

Asp Val Val Met Thr Gln Ser Pro Leu Ser Leu Pro Val Thr Leu Gly
1               5                   10                  15

Gln Pro Ala Ser Ile Ser Cys
            20

<210> SEQ ID NO 37
<211> LENGTH: 15
<212> TYPE: PRT
<213> ORGANISM: Artificial Sequence
<220> FEATURE:
<223> OTHER INFORMATION: amino acid sequence of FR2 of VL of h2P2 using
      Kabat numbering scheme

<400> SEQUENCE: 37

Trp Leu Gln Gln Arg Pro Gly Gln Ser Pro Arg Arg Leu Ile Ser
1               5                   10                  15

<210> SEQ ID NO 38
<211> LENGTH: 32
<212> TYPE: PRT
<213> ORGANISM: Artificial Sequence
<220> FEATURE:
<223> OTHER INFORMATION: amino acid sequence of FR3 of VL of h2P2 using
      Kabat numbering scheme

<400> SEQUENCE: 38

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 39
<211> LENGTH: 10
<212> TYPE: PRT
<213> ORGANISM: Artificial Sequence
<220> FEATURE:
<223> OTHER INFORMATION: amino acid sequence of FR4 of VL of h2P2 when
      CDRs as per Kabat

<400> SEQUENCE: 39

Phe Gly Gln Gly Thr Lys Leu Glu Ile Lys
1               5                   10

<210> SEQ ID NO 40
<211> LENGTH: 113
<212> TYPE: PRT
<213> ORGANISM: Artificial Sequence
<220> FEATURE:
<223> OTHER INFORMATION: amino acid sequence of VH of h2P2

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Ile His Trp Val Arg Gln Ala Pro Gly Gln Gly Leu Glu Leu Ile
        35                  40                  45

Gly Trp Ile Asp Pro Glu Ser Gly Asp Thr Asn Tyr Ala Gln Lys Phe
```

```
                    50                  55                  60
Gln Val Lys Ala Thr Met Thr Arg Asp Thr Ser Ile Ser Thr Ala Tyr
 65                  70                  75                  80

Met Glu Leu Ser Arg Leu Arg Ser Asp Thr Ala Val Tyr Tyr Cys
                 85                  90                  95

Asn Asp Gly Ser Gly Tyr Trp Gly Gln Gly Thr Thr Val Thr Val Ser
                100                 105                 110

Ser

<210> SEQ ID NO 41
<211> LENGTH: 112
<212> TYPE: PRT
<213> ORGANISM: Artificial Sequence
<220> FEATURE:
<223> OTHER INFORMATION: amino acid sequence of VL of h2P2

<400> SEQUENCE: 41

Asp Val Val Met Thr Gln Ser Pro Leu Ser Leu Pro Val Thr Leu Gly
 1               5                  10                  15

Gln Pro Ala Ser Ile Ser Cys Lys Ser Ser Gln Ser Leu Leu Asp Ser
                20                  25                  30

Asp Gly Glu Thr Tyr Leu Asn Trp Leu Gln Gln Arg Pro Gly Gln Ser
             35                  40                  45

Pro Arg Arg Leu Ile Ser Leu Val Ser Lys Leu Asp Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Tyr Thr Phe Gly Gln Gly Thr Lys Leu Glu Ile Lys
                100                 105                 110

<210> SEQ ID NO 42
<211> LENGTH: 17
<212> TYPE: PRT
<213> ORGANISM: Artificial Sequence
<220> FEATURE:
<223> OTHER INFORMATION: amino acid sequence of CDR2 of VH chain of
      antibody h2P2 using Kabat numbering scheme

<400> SEQUENCE: 42

Trp Ile Asp Pro Glu Ser Gly Asp Thr Asn Tyr Ala Gln Lys Phe Gln
 1               5                  10                  15

Val
```

IL-21 AGONIST ANTIBODIES AND METHODS OF TREATMENT USING SAME

RELATED APPLICATION

This application claims priority from Australian provisional patent application no. 2014905159, the entire contents of which are incorporated herein by reference.

FIELD OF THE INVENTION

The invention relates to IL-21, to antibodies and related fragments thereof for binding to IL-21, to production of said antibodies and fragments and to use of said antibodies and fragments for detection and therapy of various conditions, in particular inflammation, infection and oncology.

SEQUENCE LISTING

The present application is filed with a sequence listing in electronic form. The entire contents of the sequence listing are herein incorporated and constitute part of the specification.

BACKGROUND OF THE INVENTION

Cytokines generally stimulate proliferation or differentiation of cells of the hematopoietic lineage or participate in the immune and inflammatory response mechanisms of the body. The interleukins are a family of cytokines that mediate immunological responses. Central to an immune response is the T cell, which produces many cytokines and effects adaptive immunity to antigens. Cytokines produced by the T cell have been classified as TH1 and TH2. Type 1 cytokines include IL-2, IFN-γ, LT-α, and are involved in inflammatory responses, viral immunity, intracellular parasite immunity and allograft rejection. Type 2 cytokines include IL-4, IL-5, IL-6, IL-10 and IL-13, and are involved in humoral responses, helminth immunity and allergic response. Shared cytokines between Type 1 and 2 include IL-3, GM-CSF and TNF-α. There is some evidence to suggest that Type 1 and Type 2 producing T cell populations preferentially migrate into different types of inflamed tissue.

Natural killer (NK) cells have a common progenitor cell with T cells and B cells, and play a role in immune surveillance. NK cells, which comprise up to 15% of blood lymphocytes, do not express antigen receptors, and are a component of innate immunity. NK cells are involved in the recognition and killing of tumor cells and virally infected cells. In vivo, NK cells are believed to require activation, however, in vitro, NK cells have been shown to kill some types of tumor cells without activation.

IL-21 has been shown to be a potent modulator of cytotoxic T cells and NK cells. IL-21 has been shown to co-stimulate the expansion of NK cells, and it has been demonstrated to enhance the effector functions of these cells. T cell responses include enhancement of primary antigen response as modulation of memory T cell functions.

It has been shown that IL-21R knock-out mice express higher levels of IgE and lower levels of IgG1 than normal mice after antigen exposure. IgE levels decreased after mice were injected with IL-21. This has implications for the role of IL-21 in controlling allergic responses because of the role of IgE in hypersensitivity type 1 responses.

IL-21 has been tried as therapy for alleviating allergic responses. It was shown to be successful in decreasing pro-inflammatory cytokines produced by T cells in addition to decreasing IgE levels in a mouse model for rhinitis (nasal passage inflammation). This has strong implications for the pharmacological development of IL-21 for controlling both localized and systemic allergies.

A role for IL-21 in modulating the differentiation programming of human T cells was first reported by Li et al (Journal of immunology 175 (4): 2261-9 (2005)), where it was shown to enrich for a population of central memory-type CTL with a unique CD28+CD127hi CD45RO+ phenotype with IL-2 producing capacity. Tumor-reactive antigen-specific CTL generated by priming in the presence of IL-21 led to a stable, 'helper-independent' phenotype.

IL-21 was approved for Phase 1 clinical trials in metastatic melanoma (MM) and renal cell carcinoma (RCC) patients. It was shown to be safe for administration with flu-like symptoms as side effects. Dose-limiting toxicities included low lymphocyte, neutrophil, and thrombocyte count as well as hepatotoxicity. According to the Response Evaluation Criteria in Solid Tumors (RECIST) response scale, 2 out of 47 MM patients and 4 out of 19 RCC patients showed complete and partial responses, respectively. In addition, there was an increase of perforin, granzyme B, IFN-γ, and CXCR3 mRNA in peripheral NK cells and CD8+ T cells. This suggested that IL-21 enhances the CD8+ effector functions thus leading to anti-tumor response. IL-21 proceeded to Phase 2 clinical trials where it was administered alone or coupled with drugs as sorafinib and rituximab.

IL-21 may also be a critical factor in the control of persistent viral infections. IL-21 (or IL-21R) knock-out mice infected with chronic LCMV (lymphocytic choriomeningitis virus) were not able to overcome chronic infection compared to normal mice. Besides, these mice with impaired IL-21 signaling had more dramatic exhaustion of LCMV-specific CD8+ T cells, suggesting that IL-21 produced by CD4+ T cells is required for sustained CD8+ T cell effector activity and then, for maintaining immunity to resolve persistent viral infection. Thus, IL-21 may contribute to the mechanism by which CD4+T helper cells orchestrate the immune system response to viral infections.

In HIV infected subjects, IL-21 has been reported to critically improve the HIV-specific cytotoxic T cell responses and NK cell functions. It has also been shown that HIV-specific CD4 T cells from "HIV controllers" (rare individuals who don't progress to AIDS by controlling the virus replication without treatment) are able to produce significantly more IL-21 than those of progressors. In addition, IL-21 producing virus specific CD8 T cells were also preferentially found in HIV controllers These data and the fact that IL-21 stimulated CD8 or NK cells are able to inhibit HIV viral replication in vitro show that this cytokine could potentially be useful for anti-HIV therapeutics.

Monoclonal antibodies directed against IL-21 have been developed, however these antibodies have been shown to antagonize or inhibit the function of IL-21. These antagonistic antibodies are useful in suppressing inflammatory disorders. There have been no publications to date of the development of antibodies which agonize or enhance IL-21 activity.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The invention provides an antigen binding site that binds to or specifically binds to IL-21 and enhances IL-21 activity, wherein the antigen binding site comprises one or more sequences at least about 80%, at least 85%, at least 90%, at least 92%, at least 95%, at least 97%, at least 99% identical to a sequence selected from the group consisting of SEQ ID NO: 24 to 39.

The invention also provides an antigen binding site that binds to or specifically binds to IL-21 and enhances IL-21 activity, wherein the antigen binding site comprises one or more sequences selected from the group consisting of SEQ ID NO: 24 to 39.

The invention also provides an antigen binding site that enhances IL-21-mediated proliferation of B cells in vitro or in vivo, wherein the antigen binding site comprises one or more sequences at least about 80%, at least 85%, at least 90%, at least 92%, at least 95%, at least 97%, at least 99%, or 100% identical to a sequence selected from the group consisting of SEQ ID NO: 24 to 39.

The invention also provides an antigen binding site that enhances IL-21-mediated cytotoxicity of CD8+ T cells in vitro or in vivo, wherein the antigen binding site comprises one or more sequences at least about 80%, at least 85%, at least 90%, at least 92%, at least 95%, at least 97%, at least 99%, or 100% identical to a sequence selected from the group consisting of SEQ ID NO: 24 to 39.

The invention also provides an antigen binding site that enhances IL-21-mediated proliferation of NK cells, wherein the antigen binding comprises one ore more sequences at least about 80%, at least 85%, at least 90%, at least 92%, at least 95%, at least 97%, at least 99%, or 100% identical to a sequence selected from the group consisting of SEQ ID NO: 24 to 39.

The invention also provides an antigen binding site that is an IL-21 agonist, wherein the antigen binding site comprises one or more sequences at least about 80%, at least 85%, at least 90%, at least 92%, at least 95%, at least 97%, at least 99%, or 100% identical to a sequence selected from the group consisting of SEQ ID NO: 24 to 39.

The invention also provides an antigen binding site that enhances IL-21 half-life in vivo, wherein the antigen binding site comprises one or more sequences at least about 80%, at least 85%, at least 90%, at least 92%, at least 95%, at least 97%, at least 99%, or 100% identical to a sequence selected from the group consisting of SEQ ID NO: 24 to 39. For example, the antigen binding site may enhance IL-21 half-life in vivo from hours to days. In one example, the antigen binding site enhances IL-21 half-life in vivo for at least 24 hours.

In any aspect or embodiment of the invention, the antigen binding site may enhance the activity of IL-21 by at least five-fold compared to IL-21 activity in the absence of the antigen binding site.

The invention also provides an antigen binding site that binds to or specifically binds to IL-21 and enhances IL-21 activity, wherein the antigen binding site comprises:

(a) a framework region (FR) 1 comprising a sequence at least about 65%, at least 70%, at least 75%, at least 80% identical to a sequence set forth in SEQ ID NO: 24, a FR2 comprising a sequence at least about 80% identical to a sequence set forth in SEQ ID NO: 25, a FR3 comprising a sequence at least about 70%, at least 75%, at least 80% identical to a sequence set forth in SEQ ID NO: 26, and a FR4 comprising a sequence at least about 80% identical to a sequence set forth in SEQ ID NO: 27;

(b) a FR1 comprising a sequence at least about 80% identical to a sequence set forth in SEQ ID NO: 28, a FR2 comprising a sequence at least about 80% identical to a sequence set forth in SEQ ID NO: 29, a FR3 comprising a sequence at least about 80% identical to a sequence set forth in SEQ ID NO: 30, and a FR4 comprising a sequence at least about 80% identical to a sequence set forth in SEQ ID NO: 31;

(c) a FR1 comprising a sequence at least about 65%, at least 70%, at least 75%, at least 80% identical to a sequence set forth in SEQ ID NO: 32, a FR2 comprising a sequence at least about 80% identical to a sequence set forth in SEQ ID NO: 33, a FR3 comprising a sequence at least about 70%, at least 75%, at least 80% identical to a sequence set forth in SEQ ID NO: 34, and a FR4 comprising a sequence at least about 80% identical to a sequence set forth in SEQ ID NO: 35;

(d) a FR1 comprising a sequence at least about 80% identical to a sequence set forth in SEQ ID NO: 36, a FR2 comprising a sequence at least about 80% identical to a sequence set forth in SEQ ID NO: 37, a FR3 comprising a sequence at least about 80% identical to a sequence set forth in SEQ ID NO: 38, and a FR4 comprising sequence at least about 80% identical to a sequence set forth in SEQ ID NO: 39;

(e) each of (a) and (b); or (f) each of (c) and (d).

The present invention also provides an antigen binding site that binds to or specifically binds to an epitope of IL-21 comprising the sequence STNAGRRQK (SEQ ID NO: 23), wherein the antigen binding site comprises (a) at least one framework region comprising a sequence at least about 65%, at least 70%, at least 75%, at least 80%, at least 85%, at least 90%, at least 92%, at least 95%, at least 97%, at least 99%, or 100% identical to a sequence selected from the group consisting of SEQ ID NO: 24 to 39;

(b) framework regions comprising each of the sequences 24 to 27;

(c) framework regions comprising each of the sequences 28 to 31;

(d) frameworks regions comprising each of the sequences 32 to 35;

(e) framework regions comprising each of the sequences 36 to 39; or (f) each of (b), (c), (d) and (e).

Preferably, the antigen binding site binds to or specifically binds to an epitope comprising the sequence PPSTNAGRRQKHRLT as set forth in SEQ ID NO: 19. Preferably, the antigen binding site binds to or specifically binds to an epitope of IL-21 comprising the sequence PPSTNAGRRQKHRLTCPSCDSYE as set forth in SEQ ID NO: 20. Preferably, the antigen binding site binds to, or specifically binds to an epitope of IL-21 comprising the sequence IKKLKRKPPSTNAGRRQKHRLTCPSCDSYE set forth in SEQ ID NO:4.

The present invention also provides an antigen binding site that binds to or specifically binds to an epitope of IL-21 and wherein the antigen binding site competitively inhibits binding of antibody 2P2 (comprising a VH comprising a sequence set forth in SEQ ID NO: 2 and a VL comprising a sequence set forth in SEQ ID NO: 3) to IL-21, wherein the antigen binding site includes at least one framework region comprising a sequence at least about 65%, at least 70%, at least 80%, at least 85%, at least 90%, at least 92%, at least 95%, at least 97%, at least 99%, or 100% identical to a sequence selected from the group consisting of SEQ ID NO: 24 to 39.

In any embodiment, the antigen binding site competitively inhibits binding of antibody 2P2 to an epitope sequence set forth in SEQ ID NO: 19, 20 or 4.

Preferably, the antigen binding site binds to, or specifically binds to mammalian IL-21 (hIL-21). Even more preferably, the antigen binding site binds to, or specifically binds to human IL-21. Alternatively, the antigen binding site binds to, or specifically binds to cat or dog IL-21. The antigen binding site may not detectably bind to mouse IL-21.

The antigen binding site may have an affinity constant (KD) for mammalian IL-21 or hIL-21 of about $9\times10^{-9}$M or less. For example, the KD is about $8\times10^{-9}$M or less or about $7\times10^{-9}$M or less or about $6\times10^{-9}$M or less or about $5\times10^{-9}$M or less. In one example, the KD is about $4.8\times10^{-9}$M or less. In another example, the antigen binding site has an affinity constant (KD) for mammalian IL-21 or hIL-21 of about $2\times10^{-9}$M or less. For example, the KD is about $1\times10^{-9}$M or less or about $9\times10^{-10}$M or less or about $8\times10^{-10}$M or less or about $7\times10^{-10}$M or less. In one example, the KD is about $5\times10^{-10}$M or less. In one example, the KD is about $4\times10^{-10}$M or less. In one example, the KD is about $3\times10^{-10}$M or less. In one example, the KD is about $2\times10^{-10}$M or less. In one example, the KD is about $1.5\times10^{-10}$M or less. In one example, relating to each of the foregoing examples, the KD can be $0.1\times10^{-12}$M or more or $1\times10^{-12}$M or more. Typically, the KD is assessed using a biosensor, e.g., by surface plasmon resonance. For example, the antigen binding site is immobilized and the level of binding to hIL-21 or mammalian IL-21 is determined.

The present invention provides an antigen binding site that binds to or specifically binds to IL-21 and enhances IL-21 activity, the antigen binding site comprising:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
any one of the framework regions comprises a sequence at least about 80%, at least 85%, at least 90%, at least 92%, at least 95%, at least 97%, at least 99% or 100% identical to a sequence set forth in SEQ ID NO: 32 to 35; and
wherein:
CDR1 has a sequence of: DYYIH (SEQ ID NO: 11),
CDR2 has a sequence of: WIDPESGDTEYAPKFQV (SEQ ID NO: 12) or WIDPESGDTNYAQKFQV (SEQ ID NO: 42),
CDR3 has a sequence of: GSGY (SEQ ID NO: 13).

The present invention provides an antigen binding site that binds to or specifically binds to IL-21 and enhances IL-21 activity, the antigen binding site comprising:

FR1a-CDR1a-FR2a-CDR2a-FR3a-CDR3a-FR4a wherein:
FR1a, FR2a, FR3a and FR4a are each framework regions;
CDR1a, CDR2a and CDR3a are each complementarity determining regions;
wherein:
any one of the framework regions comprises a sequence at least about 80%, at least 85%, at least 90%, at least 92%, at least 95%, at least 97%, at least 99% or 100% identical to a sequence set forth in SEQ ID NO: 36 to 39; and
wherein:
CDR1a has a sequence of: KSSQSLLDSDGETYLN (SEQ ID NO: 14),
CDR2a has a sequence of: LVSKLDS (SEQ ID NO: 15),
CDR3a has a sequence of: WQGTHFPYT (SEQ ID NO: 16).

The present invention provides an antigen binding site that binds to or specifically binds to IL-21 and enhances IL-21 activity, the antigen binding site comprising:

FR1-CDR1-FR2-CDR2-FR3-CDR3-FR4-linker-FR1a-CDR1a-FR2a-CDR2a-FR3a-CDR3a-FR4a wherein:
FR1, FR2, FR3 and FR4 are each framework regions;
CDR1, CDR2 and CDR3 are each complementarity determining regions;
FR1a, FR2a, FR3a and FR4a are each framework regions;
CDR1a, CDR2a and CDR3a are each complementarity determining regions;
wherein:
FR1, FR2, FR3 and FR4 has a sequence at least about 80%, at least 85%, at least 90%, at least 92%, at least 95%, at least 97%, at least 99% or 100% identical to a sequence set forth in SEQ ID NO: 32 to 35,
FR1a, FR2a, FR3a and FR4a has a sequence at least about 80%, at least 85%, at least 90%, at least 92%, at least 95%, at least 97%, at least 99% or 100% identical to a sequence set forth in SEQ ID NO: 36 to 39, and
wherein:
CDR1 has a sequence of: DYYIH (SEQ ID NO: 11),
CDR2 has a sequence of: WIDPESGDTEYAPKFQV (SEQ ID NO: 12) or WIDPESGDTNYAQKFQV (SEQ ID NO: 42),
CDR3 has a sequence of: GSGY (SEQ ID NO: 13),
CDR1a has a sequence of: KSSQSLLDSDGETYLN (SEQ ID NO: 14),
CDR2a has a sequence of: LVSKLDS (SEQ ID NO: 15),
CDR3a has a sequence of: WQGTHFPYT (SEQ ID NO: 16).

The present invention provides an antigen binding site that binds to or specifically binds to IL-21 and enhances IL-21 activity, the antigen binding site comprising:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
any one of the framework regions comprises a sequence at least about 80%, at least 85%, at least 90%, at least 92%, at least 95%, at least 97%, at least 99% or 100% identical to a sequence set forth in SEQ ID NO: 24 to 27; and
wherein:
CDR1 has a sequence of: GFNIKDYY (SEQ ID NO: 5),
CDR2 has a sequence of: IDPESGDT (SEQ ID NO: 6),
CDR3 has a sequence of: NDGSGY (SEQ ID NO: 7).

The present invention provides an antigen binding site that binds to or specifically binds to IL-21 and enhances IL-21 activity, the antigen binding site comprising:

FR1a-CDR1a-FR2a-CDR2a-FR3a-CDR3a-FR4a wherein:
FR1a, FR2a, FR3a and FR4a are each framework regions;
CDR1a, CDR2a and CDR3a are each complementarity determining regions;
wherein:
any one of the framework regions comprises a sequence at least about 80%, at least 85%, at least 90%, at least 92%, at least 95%, at least 97%, at least 99% or 100% identical to a sequence set forth in SEQ ID NO: 28 to 31; and wherein:
CDR1a has a sequence of: QSLLDSDGETY (SEQ ID NO: 8),
CDR2a has a sequence of: LVS (SEQ ID NO: 9),
CDR3a has a sequence of: WQGTHFPYT (SEQ ID NO: 10).

The present invention provides an antigen binding site that binds to or specifically binds to IL-21 and enhances IL-21 activity, the antigen binding site comprising:

FR1-CDR1-FR2-CDR2-FR3-CDR3-FR4-linker-
FR1a-CDR1a-FR2a-CDR2a-FR3a-CDR3a-FR4a wherein:
FR1, FR2, FR3 and FR4 are each framework regions;
CDR1, CDR2 and CDR3 are each complementarity determining regions;
FR1a, FR2a, FR3a and FR4a are each framework regions;
CDR1a, CDR2a and CDR3a are each complementarity determining regions;
wherein:
FR1, FR2, FR3 and FR4 has a sequence at least about 80%, at least 85%, at least 90%, at least 92%, at least 95%, at least 97%, at least 99% or 100% identical to a sequence set forth in SEQ ID NO: 24 to 27,
FR1a, FR2a, FR3a and FR4a has a sequence at least about 80%, at least 85%, at least 90%, at least 92%, at least 95%, at least 97%, at least 99% or 100% identical to a sequence set forth in SEQ ID NO: 28 to 31, and; and
wherein:
CDR1 has a sequence of: GFNIKDYY (SEQ ID NO: 5),
CDR2 has a sequence of: IDPESGDT (SEQ ID NO: 6),
CDR3 has a sequence of: NDGSGY (SEQ ID NO; 7),
CDR1a has a sequence of: QSLLDSDGETY (SEQ ID NO: 8),
CDR2a has a sequence of: LVS (SEQ ID NO: 9),
CDR3a has a sequence of: WQGTHFPYT (SEQ ID NO: 10).

The present invention provides an antigen binding site that binds to or specifically binds to IL-21 and enhances IL-21 activity, the antigen binding site comprising:

FR1-CDR1-FR2-CDR2-FR3-CDR3-FR4 wherein:
FR1, FR2, FR3 and FR4 are each framework regions;
CDR1, CDR2 and CDR3 are each complementarity determining regions;
wherein:
CDR1 has a sequence of: DYYIH (SEQ ID NO: 11),
CDR2 has a sequence of: or WIDPESGDTNYAQKFQV (SEQ ID NO: 42),
CDR3 has a sequence of: GSGY (SEQ ID NO: 13).

The present invention provides an antigen binding site that binds to or specifically binds to IL-21 and enhances IL-21 activity, the antigen binding site comprising:

FR1-CDR1-FR2-CDR2-FR3-CDR3-FR4-linker-
FR1a-CDR1a-FR2a-CDR2a-FR3a-CDR3a-FR4a wherein:
FR1, FR2, FR3 and FR4 are each framework regions;
CDR1, CDR2 and CDR3 are each complementarity determining regions;
FR1a, FR2a, FR3a and FR4a are each framework regions;
CDR1a, CDR2a and CDR3a are each complementarity determining regions;
wherein:
CDR1 has a sequence of: DYYIH (SEQ ID NO: 11),
CDR2 has a sequence of: WIDPESGDTNYAQKFQV (SEQ ID NO: 42),
CDR3 has a sequence of: GSGY (SEQ ID NO: 13),
CDR1a has a sequence of: KSSQSLLDSDGETYLN (SEQ ID NO: 14),
CDR2a has a sequence of: LVSKLDS (SEQ ID NO: 15),
CDR3a has a sequence of: WQGTHFPYT (SEQ ID NO: 16).

In any aspect of the present invention described above, the antigen binding site may comprise the framework regions and complementarity determining regions in the following arrangement: FR1a-CDR1a-FR2a-CDR2a-FR3a-CDR3a-FR4a-linker-FR1-CDR1-FR2-CDR2-FR3-CDR3

The present invention provides an antigen binding site that binds to or specifically binds to IL-21 and enhances IL-21 activity, the antigen binding site includes at least one of:

(i) a VH comprising a complementarity determining region (CDR) 1 comprising a sequence at least about 80%, at least 85%, at least 90%, at least 92%, at least 95%, at least 97%, at least 99% identical to a sequence set forth in SEQ ID NO:5, a CDR2 comprising a sequence at least about 80%, at least 85%, at least 90%, at least 92%, at least 95%, at least 97%, at least 99% identical to a sequence set in SEQ ID NO:6; a CDR3 comprising a sequence at least about 80%, at least 85%, at least 90%, at least 92%, at least 95%, at least 97%, at least 99% identical to a sequence set forth in SEQ ID NO: 7, and at least one framework region comprising a sequence at least about 65%, at least 70%, at least 80%, at least 85%, at least 90%, at least 92%, at least 95%, at least 97%, at least 99% identical to a sequence set forth in SEQ ID NO: 24 to 27;

(ii) a VH comprising a complementarity determining region (CDR) 1 comprising a sequence at least about 80%, at least 85%, at least 90%, at least 92%, at least 95%, at least 97%, at least 99% identical to a sequence set forth in SEQ ID NO:11, a CDR2 comprising a sequence at least about 80%, at least 85%, at least 90%, at least 92%, at least 95%, at least 97%, at least 99% identical to a sequence set in SEQ ID NO:12 or 42; a CDR3 comprising a sequence at least about 80%, at least 85%, at least 90%, at least 92%, at least 95%, at least 97%, at least 99% identical to a sequence set forth in SEQ ID NO: 13, and at least one framework region comprising a sequence at least about 65%, at least 70%, at least 80%, at least 85%, at least 90%, at least 92%, at least 95%, at least 97%, at least 99% identical to a sequence set forth in SEQ ID NO: 32 to 35;

(iii) a VH comprising a complementarity determining region (CDR) 1 comprising a sequence at least about 80%, at least 85%, at least 90%, at least 92%, at least 95%, at least 97%, at least 99% identical to a sequence set forth in SEQ ID NO:11, a CDR2 comprising a sequence at least about 80%, at least 85%, at least 90%, at least 92%, at least 95%, at least 97%, at least 99% identical to a sequence set in SEQ ID NO: 42; a CDR3 comprising a sequence at least about 65%, at least 70%, at least 80%, at least 85%, at least 90%, at least 92%, at least 95%, at least 97%, at least 99% identical to a sequence set forth in SEQ ID NO: 13, (iv) a VH comprising a sequence at least about 95% or 96% or 97% or 98% or 99% identical to a sequence set forth in SEQ ID NO: 40;

(v) a VL comprising a CDR1 comprising a sequence at least about 80%, at least 85%, at least 90%, at least 92%, at least 95%, at least 97%, at least 99% identical to a sequence set forth in SEQ ID NO: 8, a CDR2 comprising a sequence at least about 80%, at least 85%, at least 90%, at least 92%, at least 95%, at least 97%, at least 99% identical to a sequence set forth in SEQ ID NO: 9, a CDR3 comprising a sequence at least about 80%, at least 85%, at least 90%, at least 92%, at least 95%, at least 97%, at least 99% identical to a sequence set forth in SEQ ID NO: 10, and at least one framework region comprising a sequence at least about 80%, at least 85%, at least 90%, at least 92%, at least 95%, at least 97%, at least 99% identical to a sequence set forth in SEQ ID NO: 28 to 31;

(vi) a VL comprising a CDR1 comprising a sequence at least about 80%, at least 85%, at least 90%, at least 92%, at least 95%, at least 97%, at least 99% identical to a sequence set forth in SEQ ID NO: 14, a CDR2 comprising a sequence at least about 80%, at least 85%, at least 90%, at least 92%, at least 95%, at least 97%, at least 99% identical to a sequence set forth in SEQ ID NO: 15, a CDR3 comprising a sequence at least about 80%, at least 85%, at least 90%, at least 92%, at least 95%, at least 97%, at least 99% identical to a sequence set forth in SEQ ID NO: 16, and at least one framework region comprising a sequence at least about 80%, at least 85%, at least 90%, at least 92%, at least 95%, at least 97%, at least 99% identical to a sequence set forth in SEQ ID NO: 36 to 39;

(vii) a VL comprising a sequence at least about 95% or 96% or 97% or 98% or 99% identical to a sequence set forth in SEQ ID NO: 41;

(viii) a VH comprising a CDR1 comprising a sequence set forth in SEQ ID NO: 5, a CDR2 comprising a sequence set forth between in SEQ ID NO: 6, a CDR3 comprising a sequence set forth in SEQ ID NO: 7, and at least one framework region comprising a sequence set forth in SEQ ID NO: 24 to 27;

(ix) a VH comprising a CDR1 comprising a sequence set forth in SEQ ID NO: 11, a CDR2 comprising a sequence set forth between in SEQ ID NO: 12 or 42, a CDR3 comprising a sequence set forth in SEQ ID NO: 13, and at least one framework region comprising a sequence set forth in SEQ ID NO: 32 to 35;

(x) a VH comprising a CDR1 comprising a sequence set forth in SEQ ID NO: 11, a CDR2 comprising a sequence set forth between in SEQ ID NO: 42, a CDR3 comprising a sequence set forth in SEQ ID NO: 13, (xi) a VH comprising a sequence set forth in SEQ ID NO: 40;

(x) a VL comprising a CDR1 comprising a sequence set SEQ ID NO: 8, a CDR2 comprising a sequence set forth in SEQ ID NO: 9 and a CDR3 comprising a sequence set forth in SEQ ID NO: 10, and at least one framework region comprising a sequence set forth in SEQ ID NO: 28 to 31;

(xii) a VL comprising a CDR1 comprising a sequence set SEQ ID NO: 14, a CDR2 comprising a sequence set forth in SEQ ID NO: 15 and a CDR3 comprising a sequence set forth in SEQ ID NO: 16, and at least one framework region comprising a sequence set forth in SEQ ID NO: 36 to 39;

(xiii) a VL comprising a sequence set forth in SEQ ID NO: 41;

(xiv) a VH comprising a CDR1 comprising a sequence set forth in SEQ ID NO: 5, a CDR2 comprising a sequence set forth between in SEQ ID NO: 6 and a CDR3 comprising a sequence set forth in SEQ ID NO: 7; and a VL comprising a CDR1 comprising a sequence set SEQ ID NO: 8, a CDR2 comprising a sequence set forth in SEQ ID NO: 9 and a CDR3 comprising a sequence set forth in SEQ ID NO: 10; and at least one framework region comprising a sequence set forth in SEQ ID NO: 24 to 31;

(xv) a VH comprising a CDR1 comprising a sequence set forth in SEQ ID NO: 11, a CDR2 comprising a sequence set forth between in SEQ ID NO: 12 or 42 and a CDR3 comprising a sequence set forth in SEQ ID NO: 13; and a VL comprising a CDR1 comprising a sequence set SEQ ID NO: 14, a CDR2 comprising a sequence set forth in SEQ ID NO: 15 and a CDR3 comprising a sequence set forth in SEQ ID NO: 16; and at least one framework region comprising a sequence set forth in SEQ ID NO: 32 to 39;

(xvi) a VH comprising a CDR1 comprising a sequence set forth in SEQ ID NO: 11, a CDR2 comprising a sequence set forth between in SEQ ID NO: 42 and a CDR3 comprising a sequence set forth in SEQ ID NO: 13; and a VL comprising a CDR1 comprising a sequence set SEQ ID NO: 14, a CDR2 comprising a sequence set forth in SEQ ID NO: 15 and a CDR3 comprising a sequence set forth in SEQ ID NO: 16, and (xvii) a VH comprising a sequence set forth in SEQ ID NO: 40 and a VL comprising a sequence set forth in SEQ ID NO: 41.

The present invention also include any antigen binding site described above that that includes one or more conservative substitutions of the amino acids that are different in SEQ ID NO: 40 compared to SEQ ID NO: 2, and/or SEQ ID NO: 41 compared to SEQ ID NO: 3. For example, there is a difference at position 1 in SEQ ID NO:40 compared to SEQ ID NO: 3, a Gln instead of a Glu, and contemplated herein is an antigen binding site as described herein having a conservative substitution for Gln at that position.

As described herein, the antigen binding site may be in the form of:
(i) a single chain Fv fragment (scFv);
(ii) a dimeric scFv (di-scFv);
(iii) one of (i) or (ii) linked to a constant region of an antibody, Fc or a heavy chain constant domain (CH) 2 and/or CH3; or
(iv) one of (i) or (ii) linked to a protein that binds to an immune effector cell.

Further, as described herein, the antigen binding site may be in the form of:
(i) a diabody;
(ii) a triabody;
(iii) a tetrabody;
(iv) a Fab;
(v) a F(ab')$_2$;
(vi) a Fv;
(vii) one of (i) to (vi) linked to a constant region of an antibody, Fc or a heavy chain constant domain (CH) 2 and/or CH3;
(viii) one of (i) to (vi) linked to a protein that binds to an immune effector cell.

The foregoing proteins can also be referred to as antigen binding domains of antibodies. Typically, the protein is an antibody, for example, a monoclonal antibody.

As used herein the antigen binding site may be a variable domain.

In any aspect or embodiment, the antibody is a naked antibody. Specifically, the antibody is in a non-conjugated form and is not adapted to form a conjugate. In one embodiment, the antibody is not conjugated to, or adapted to be conjugated to, biotin or phycoerythrin.

In one example, the complementarity determining region sequences (CDRs) are defined according to the Kabat numbering system.

In another example, the CDRs are defined according to the IMGT numbering system.

Reference herein to a protein or antibody that "binds to" IL-21 provides literal support for a protein or antibody that "binds specifically to" or "specifically binds to" IL-21.

The present invention also provides antigen binding domains or antigen binding fragments of the foregoing antibodies.

The present invention provides an antigen binding site, antigen binding domain or antigen binding fragment thereof as described herein, wherein the antigen binding site, antigen binding domain or antigen binding fragment thereof binds to IL-21, enhances the activity of IL-21, or enhances IL-21 half-life in vivo to at least 70%, 75%, 80%, 85%, 90%, 91%, 92%, 93%, 94%, 95%, 96%, 97%, 98%, 99% the level of 2P2 (also referred to herein as m2P2) as described herein. Preferably, binds to IL-21 includes any one or more of on-rate, off-rate or binding constant. Enhancing the IL-21 activity includes any one of more of the functions described or assayed for herein, for example, IL-21-mediated proliferation of B cells in vitro or in vivo, IL-21-mediated cytotoxicity of CD8+ T cells in vitro or in vivo, IL-21-mediated proliferation of NK cells.

The invention provides a fusion protein comprising an antigen binding site, immunoglobulin variable domain, antibody, dab, di-scFv, scFv, Fab, Fab', F(ab')2, Fv fragment, diabody, triabody, tetrabody, linear antibody, single-chain antibody molecule, or multispecific antibody as described herein.

The invention provides a conjugate in the form of an antigen binding site, immunoglobulin variable domain, antibody, dab, di-scFv, scFv, Fab, Fab', F(ab')2, Fv fragment, diabody, triabody, tetrabody, linear antibody, single-chain antibody molecule, or multispecific antibody or fusion protein as described herein conjugated to a label or a cytotoxic agent. Preferably, the conjugate is not biotin or phycoerythrin.

The invention provides an antibody for binding to an antigen binding site, immunoglobulin variable domain, antibody, dab, di-scFv, scFv, Fab, Fab', F(ab')2, Fv fragment, diabody, triabody, tetrabody, linear antibody, single-chain antibody molecule, or multispecific antibody, fusion protein, or conjugate as described herein.

The invention provides a nucleic acid encoding an antigen binding site, immunoglobulin variable domain, antibody, dab, di-scFv, scFv, Fab, Fab', F(ab')2, Fv fragment, diabody, triabody, tetrabody, linear antibody, single-chain antibody molecule, or multispecific antibody, fusion protein or conjugate as described herein. Preferably, the nucleic acid has a nucleotide sequence that encodes any one or more of the amino acid sequences corresponding to SEQ ID NO: 5 to 16 and one or more sequences corresponding to SEQ ID NO: 24 to 39. Preferably, the nucleic acid as a nucleotide sequence that encodes the amino acid sequence corresponding to SEQ ID NO: 40 and/or SEQ ID NO: 41.

In one example, such a nucleic acid is included in an expression construct in which the nucleic acid is operably linked to a promoter. Such an expression construct can be in a vector, e.g., a plasmid.

In examples of the invention directed to single polypeptide chain Antigen binding sites, the expression construct may comprise a promoter linked to a nucleic acid encoding that polypeptide chain.

In examples directed to multiple polypeptide chains that form an antigen binding site, an expression construct comprises a nucleic acid ejcoding a polypeptide comprising, e.g., a VH operably linked to a promoter and a nucleic acid encoding a polypeptide comprising, e.g., a VL operably linked to a promoter.

In another example, the expression construct is a bicistronic expression construct, e.g., comprising the following operably linked components in 5' to 3' order:
(i) a promoter
(ii) a nucleic acid encoding a first polypeptide;
(iii) an internal ribosome entry site; and
(iv) a nucleic acid encoding a second polypeptide, wherein the first polypeptide comprises a VH and the second polypeptide comprises a VL, or vice versa.

The present invention also contemplates separate expression constructs one of which encodes a first polypeptide comprising a VH and another of which encodes a second polypeptide comprising a VL. For example, the present invention also provides a composition comprising:
(i) a first expression construct comprising a nucleic acid encoding a polypeptide comprising a VH operably linked to a promoter; and
(ii) a second expression construct comprising a nucleic acid encoding a polypeptide comprising a VL operably linked to a promoter.

The invention provides a cell comprising a vector or nucleic acid described herein. Preferably, the cell is isolated, substantially purified or recombinant. In one example, the cell comprises the expression construct of the invention or:
(i) a first expression construct comprising a nucleic acid encoding a polypeptide comprising a VH operably linked to a promoter; and
(ii) a second expression construct comprising a nucleic acid encoding a polypeptide comprising a VL operably linked to a promoter,
wherein the first and second polypeptides associate to form an Antigen binding site of the present invention.

Examples of cells of the present invention include bacterial cells, yeast cells, insect cells or mammalian cells.

The invention provides a pharmaceutical composition comprising an antigen binding site, or comprising a CDR and/or FR sequence as described herein, or an immunoglobulin variable domain, antibody, dab, di-scFv, scFv, Fab, Fab', F(ab')2, Fv fragment, diabody, triabody, tetrabody, linear antibody, single-chain antibody molecule, or multispecific antibody, fusion protein, or conjugate as described herein and a pharmaceutically acceptable carrier, diluent or excipient.

The invention provides a diagnostic composition comprising an antigen binding site, or comprising a CDR and/or FR sequence as described herein, or antigen binding site, immunoglobulin variable domain, antibody, dab, di-scFv, scFv, Fab, Fab', F(ab')2, Fv fragment, diabody, triabody, tetrabody, linear antibody, single-chain antibody molecule, or multispecific antibody, fusion protein or conjugate as described herein, a diluent and optionally a label.

The invention provides a kit or article of manufacture comprising an antigen binding site, or comprising a CDR and/or FR sequence as described herein or an immunoglobulin variable domain, antibody, dab, di-scFv, scFv, Fab, Fab', F(ab')2, Fv fragment, diabody, triabody, tetrabody, linear antibody, single-chain antibody molecule, or multispecific antibody, fusion protein or conjugate as described herein.

The invention provides use of a sequence according to one or more of CDR1, CDR2, FR1, FR2, FR3 and FR4 as described herein to produce an antigen binding site for binding to IL-21.

The invention provides use of an antigen binding site or a CDR and/or FR sequence as described herein to produce an anti-IL-21 antigen binding site having increased affinity for IL-21.

The invention provides a library of nucleic acid molecules produced from the mutation of an antigen binding site or a CDR and/or FR sequence as described herein, wherein at least one nucleic acid molecule in said library encodes an antigen binding site for binding to an IL-21.

An antigen binding site, a protein or antibody as described herein may comprise a human constant region, e.g., an IgG constant region, such as an IgG1, IgG2, IgG3 or IgG4 constant region or mixtures thereof. In the case of an antibody or protein comprising a VH and a VL, the VH can be linked to a heavy chain constant region and the VL can be linked to a light chain constant region.

The C-terminal lysine of the heavy chain constant region of a whole antibody (or an Antigen binding site comprising a constant region or a CH3) of the invention may be removed, for example, during production or purification of the antibody or protein, or by recombinantly engineering the nucleic acid encoding a heavy chain of the antibody. Accordingly, whole antibodies (or Antigen binding sites) may comprise populations with all C-terminal lysine residues removed, populations with no C-terminal lysine residues removed, and/or populations having a mixture of protein with and without the C-terminal lysine residue. In some examples, the populations may additionally comprise protein in which the C-terminal lysine residue is removed in one of the heavy chain constant regions. Similarly, a composition of whole antibodies may comprise the same or a similar mix of antibody populations with or without the C-terminal lysine residue.

In one example, a protein or antibody as described herein comprises a constant region of an IgG4 antibody or a stabilized constant region of an IgG4 antibody. In one example, the protein or antibody comprises an IgG4 constant region with a proline at position 241 (according to the numbering system of Kabat (Kabat et al., Sequences of Proteins of Immunological Interest Washington D.C. United States Department of Health and Human Services, 1987 and/or 1991)).

In one example a protein or antibody as described herein or a composition of a protein or antibody as described herein, comprises a heavy chain constant region, comprising a stabilized heavy chain constant region, comprising a mixture of sequences fully or partially with or without the C-terminal lysine residue.

In one example, an antibody of the invention comprises a VH disclosed herein linked or fused to an IgG4 constant region or stabilized IgG4 constant region (e.g., as discussed above) and the VL is linked to or fused to a kappa light chain constant region.

The functional characteristics of an antigen binding site of the invention will be taken to apply mutatis mutandis to an antibody of the invention.

In one example, an antigen binding site or antibody as described herein is isolated, substantially purified and/or recombinant.

In one example, an antigen binding site or antibody of the invention is conjugated to another compound, for example, a detectable label or a compound that extends the half-life of the protein or antibody, such as polyethylene glycol or an albumin binding protein. Other suitable compounds are described herein.

The present invention also provides a nucleic acid encoding the antigen binding site or antibody of the present invention or a polypeptide thereof.

The present invention additionally provides methods for producing an antigen binding site or antibody of the invention. For example, such a method involves maintaining the expression construct(s) of the invention under conditions sufficient for the antigen binding site or antibody to be produced.

In one example, a method for producing an antigen binding site or antibody of the invention comprises culturing the cell of the invention under conditions sufficient for the antigen binding site or antibody to be produced and, optionally, secreted.

In one example, the method for producing an antigen binding site or antibody of the invention additionally comprises isolating the protein or antibody and, optionally, formulating the antigen binding site or antibody into a pharmaceutical composition.

The present invention additionally provides a composition comprising an antigen binding site or antibody as described herein and a pharmaceutically acceptable carrier.

In some examples, the composition comprises:
(i) an antibody of the invention comprising a C-terminal lysine residue from the heavy chain;
(ii) an antibody of the invention lacking a C-terminal lysine residue from the heavy chain; and/or
(iii) an antibody of the invention comprising a C-terminal lysine residue on one heavy chain and lacking a C-terminal lysine residue on another (or the other) heavy chain,
and, optionally, a pharmaceutically acceptable carrier.

The present invention also provides a complex comprising an antigen binding site of the invention and IL-21. In one example, the IL-21 is recombinant IL-21. Examples of recombinant IL-21 are known in the art.

The present invention also provides a method for treating or preventing an infection or infectious disease, an allergic immune response or cancer in a subject, the method comprising administering an antigen binding site or complex of the invention. In this regard, an antigen binding site or complex can be used to prevent a relapse of a condition, and this is considered preventing the condition.

In one example, the infection is a chronic infection. In another example, the infection is a viral infection, such as HIV infection.

In one example, the infectious disease is hepatitis B or C.

Exemplary cancers include hematologic cancers, cancers of epithelial origin, liver cancer, pancreatic cancer, gastric cancer, osteosarcoma, endometrial cancer and ovarian cancer.

The present invention also provides a method for enhancing IL-21 activity in a subject, the method comprising administering the antigen binding site, or complex of the invention. Preferably, the IL-21 activity is proliferation of B cells, cytotoxicity of CD8+ T cells and/or proliferation of NK cells.

In one example, a method described herein comprises administering between about 0.05 mg/kg and 30 mg/kg of the antigen binding site or complex. For example, the method comprises administering between 0.1 mg/kg and 10 mg/kg or between 0.2 mg/kg and 5 mg/kg of the antigen binding site or complex. In one example, the method comprises administering about 0.5-2.0 mg/kg of the antigen binding site or complex.

The present invention also provides for use of an antigen binding site or complex as described herein in medicine.

The present invention also provides for use of an antigen binding site or complex as described herein according to any example in the manufacture of a medicament to treat an infection, an allergic immune response or cancer.

The present invention also provides a method for localizing and/or detecting and/or diagnosing and/or prognosing an IL-21-mediated condition associated with a cell expressing IL-21, the method comprising detecting in vivo an antigen binding site or antibody as described herein bound to the IL-21 expressing cell, if present, wherein the antigen binding site or antibody is conjugated to a detectable tag.

In one example, the method additionally comprises administering the antigen binding site to the subject.

The present invention also provides a method of culturing expanding a population of cells comprising, immune system precursor cells, the method comprising culturing the population of cells in vitro or ex vivo in the presence of an antigen binding site or complex of the present invention.

It will be appreciated that culturing the cells in the presence of an antigen binding site or complex of the present invention will enhance proliferation and differentiation of mature immune system cells such as NK cells, B cells and T cells.

In one embodiment, the method of culturing further comprises the addition of exogenous IL-21 to the cell population.

Cell populations comprising immune system precursor cells may be isolated from a biological sample taken from a mammalian subject. The sample may originate from a number of sources, including, but not limited to peripheral blood, leukapheresis blood product, apheresis blood product, bone marrow, thymus, tissue biopsy, tumor, lymph node tissue, gut associated lymphoid tissue, mucosa associated lymphoid tissue, liver, sites of immunologic lesions (e.g., synovial fluid), pancreas, and cerebrospinal fluid. The donor subject is preferably human, and can be fetal, neonatal, child, adult, and may be normal, diseased, or susceptible to a disease of interest.

In some embodiments, the cell sample comprises peripheral blood mononuclear cells (PBMCs) from a blood sample. By "peripheral blood mononuclear cells" or "PBMCs" is meant lymphocytes (including T-cells, B-cells, NK cells, etc.) and monocytes. In general, PBMCs are isolated from a patient using standard techniques. In some embodiments, only PBMCs are taken, either leaving or returning substantially all of the red blood cells and polymorphonuclear leukocytes to the donor. PBMCs may be isolated using methods known in the art, such as leukophoresis. In general, a 5 to 7 liter leukophoresis step is performed, which essentially removes PBMCs from a patient, returning the remaining blood components. Collection of the sample is preferably performed in the presence of an anticoagulant (e.g., heparin).

It will be appreciated that in vitro and ex vivo cell culture, as described herein, can be used for the expansion of NK cells, B cells and T cells.

It will be appreciated that the present invention also provides a method for treating or preventing an infection or infectious disease, an allergic immune response or cancer in a subject, by administering the cells which have been expanded in vitro or ex vivo, in accordance with the method described above.

The in vitro or ex vivo expanded cell population obtained by the method disclosed above, alone or in combination with an antigen binding site or complex of the present invention, can be used to prevent a relapse of a condition, and this is considered preventing the condition. Exemplary infections include HIV, hepatitis B or Hepatitis C. Exemplary cancers include hematologic cancers, cancers of epithelial origin, liver cancer, pancreatic cancer, gastric cancer, osteosarcoma, endometrial cancer and ovarian cancer.

The present invention also provides a method for detecting IL-21 or a cell expressing same in a sample, the method comprising contacting the sample with a protein or antibody as described herein according to any example such that a complex forms and detecting the complex, wherein detection of the complex is indicative of IL-21 or a cell expressing same in the sample. In one example, the method is performed ex vivo or in vitro.

The present invention also provides a kit (e.g., a package or article of manufacture) comprising an antigen binding site or complex as described herein according to any example, optionally, packaged with instructions for use in a method as described herein.

As used herein, except where the context requires otherwise, the term "comprise" and variations of the term, such as "comprising", "comprises" and "comprised", are not intended to exclude further additives, components, integers or steps. As used herein, except where the context requires otherwise, "comprise" and "include", or variations of the term such as "including" can be used interchangeably.

Further aspects of the present invention and further embodiments of the aspects described in the preceding paragraphs will become apparent from the following description, given by way of example and with reference to the accompanying drawings.

BRIEF DESCRIPTION OF THE SEQUENCE LISTING

SEQ ID NO 1: amino acid sequence of *Homo sapiens* IL-21

SEQ ID NO 2: amino acid sequence of VH chain of antibody 2P2

SEQ ID NO 3: amino acid sequence of VL chain of antibody 2P2

SEQ ID NO 4: amino acid sequence of 2P2 binding epitope

SEQ ID NO 5: amino acid sequence of CDR1 of VH chain of antibody 2P2 using IMGT numbering scheme SEQ ID NO 6: amino acid sequence of CDR2 of VH chain of antibody 2P2 using IMGT numbering scheme SEQ ID NO 7: amino acid sequence of CDR3 of VH chain of antibody 2P2 using IMGT numbering scheme SEQ ID NO 8: amino acid sequence of CDR1 of VL chain of antibody 2P2 using IMGT numbering scheme SEQ ID NO 9: amino acid sequence of CDR2 of VL chain of antibody 2P2 using IMGT numbering scheme SEQ ID NO 10: amino acid sequence of CDR3 of VL chain of antibody 2P2 using IMGT numbering scheme SEQ ID NO 11: amino acid sequence of CDR1 of VH chain of antibody 2P2 using Kabat numbering scheme SEQ ID NO 12: amino acid sequence of CDR2 of VH chain of antibody 2P2 using Kabat numbering scheme SEQ ID NO 13: amino acid sequence of CDR3 of VH chain of antibody 2P2 using Kabat numbering scheme SEQ ID NO 14: amino acid sequence of CDR1 of VL chain of antibody 2P2 using Kabat numbering scheme SEQ ID NO 15: amino acid sequence of CDR2 of VL chain of antibody 2P2 using Kabat numbering scheme SEQ ID NO 16: amino acid sequence of CDR3 of VL chain of antibody 2P2 using Kabat numbering scheme SEQ ID NO 17: nucleotide sequence encoding the VH chain of antibody 2P2

SEQ ID NO 18: nucleotide sequence encoding the VL chain of antibody 2P2

SEQ ID NO:19: amino acid sequence of 2P2 binding epitope

SEQ ID NO:20: amino acid sequence of 2P2 binding epitope

SEQ ID NO:21: amino acid sequence of 2P2 binding epitope

SEQ ID NO:22: amino acid sequence of 2P2 binding epitope

SEQ ID NO:23: core amino acid sequence of 2P2 binding epitope

SEQ ID NO: 24: amino acid sequence of FR1 of VH of h2P2 when CDRs as per IMGT

SEQ ID NO: 25: amino acid sequence of FR2 of VH of h2P2 when CDRs as per IMGT

SEQ ID NO: 26: amino acid sequence of FR3 of VH of h2P2 when CDRs as per IMGT

SEQ ID NO: 27: amino acid sequence of FR4 of VH of h2P2 when CDRs as per IMGT

SEQ ID NO: 28: amino acid sequence of FR1 of VL of h2P2 when CDRs as per IMGT

SEQ ID NO: 29: amino acid sequence of FR2 of VL of h2P2 when CDRs as per IMGT

SEQ ID NO: 30: amino acid sequence of FR3 of VL of h2P2 when CDRs as per IMGT

SEQ ID NO: 31: amino acid sequence of FR4 of VL of h2P2 when CDRs as per IMGT

SEQ ID NO: 32: amino acid sequence of FR1 of VH of h2P2 when CDRs as per Kabat

SEQ ID NO: 33: amino acid sequence of FR2 of VH of h2P2 when CDRs as per Kabat

SEQ ID NO: 34: amino acid sequence of FR3 of VH of h2P2 when CDRs as per Kabat

SEQ ID NO: 35: amino acid sequence of FR4 of VH of h2P2 when CDRs as per Kabat

SEQ ID NO: 36: amino acid sequence of FR1 of VL of h2P2 when CDRs as per Kabat

SEQ ID NO: 37: amino acid sequence of FR2 of VL of h2P2 when CDRs as per Kabat

SEQ ID NO: 38: amino acid sequence of FR3 of VL of h2P2 when CDRs as per Kabat

SEQ ID NO: 39: amino acid sequence of FR4 of VL of h2P2 when CDRs as per Kabat

SEQ ID NO: 40: amino acid sequence of VH of h2P2

SEQ ID NO: 41: amino acid sequence of VL of h2P2

SEQ ID NO: 42: amino acid sequence of CDR2 of VH chain of antibody h2P2 using Kabat numbering scheme

BRIEF DESCRIPTION OF THE DRAWINGS

FIG. 2 is a diagrammatic representation showing the CDRs of the $V_H$ and $V_L$ of antibody 2P2 determined by the IMGT numbering scheme.

FIG. 9 shows residues of human IL-21 (indicated in bold) which according to structural simulation are thought to be involved in binding by 2P2. Residues located in IL-21 Helix regions are underlined.

DETAILED DESCRIPTION OF THE EMBODIMENTS

Figure 1:
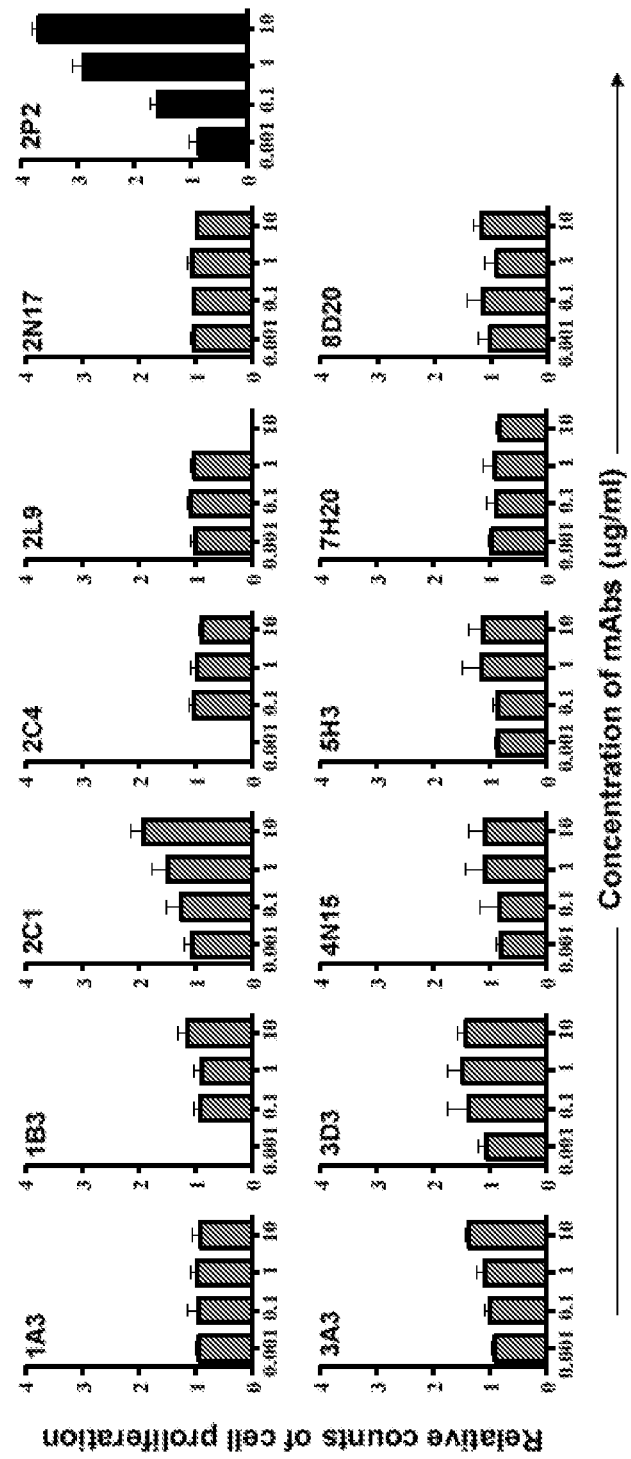
FIG. 1 shows that mAB 2P2 in the presence of 2 ng/nl of hIL-21 increased the proliferation of Ba/F3 cells expressing human IL-21 receptor (BaF3-hIL-21R) in a dose dependent manner (n=3±SEM).

It will be understood that the invention disclosed and defined in this specification extends to all alternative combinations of two or more of the individual features mentioned or evident from the text or drawings. All of these different combinations constitute various alternative aspects of the invention.

Further aspects of the present invention and further embodiments of the aspects described in the preceding paragraphs will become apparent from the following description, given by way of example and with reference to the accompanying drawings.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

All of the patents and publications referred to herein are incorporated by reference in their entirety.

For purposes of interpreting this specification, terms used in the singular will also include the plural and vice versa.

The present inventors have developed antigen binding sites, for example antibodies, that bind to and enhance the activity of IL-21. The inventors have also developed antibodies that bind to and enhance the activity of IL-21 but that have reduced immunogenicity in humans due to modification of framework regions. Specifically, the framework regions have been modified, or humanised, to reduce the likelihood that a human subject will raise an immune response against the antibody.

General

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter. Thus, as used herein, the singular forms "a", "an" and "the" include plural aspects unless the context clearly dictates otherwise. For example, reference to "a" includes a single as well as two or more; reference to "an" includes a single as well as two or more; reference to "the" includes a single as well as two or more and so forth.

Those skilled in the art will appreciate that the present invention is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific examples described herein, which are intended for the purpose of exemplification only. Functionally-equivalent products, compositions and methods are clearly within the scope of the present invention.

Any example of the present invention herein shall be taken to apply mutatis mutandis to any other example of the invention unless specifically stated otherwise.

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

The description and definitions of variable regions and parts thereof, immunoglobulins, antibodies and fragments thereof herein may be further clarified by the discussion in Kabat *Sequences of Proteins of Immunological Interest*, National Institutes of Health, Bethesda, Md., 1987 and 1991, Bork et al., *J Mol. Biol.* 242, 309-320, 1994, Chothia and Lesk *J. Mol Biol.* 196:901-917, 1987, Chothia et al. *Nature* 342, 877-883, 1989 and/or or Al-Lazikani et al., *J Mol Biol* 273, 927-948, 1997.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As used herein the term "derived from" shall be taken to indicate that a specified integer may be obtained from a particular source albeit not necessarily directly from that source.

Reference herein to a range of, e.g., residues, will be understood to be inclusive. For example, reference to "a region comprising amino acids 56 to 65" will be understood in an inclusive manner, i.e., the region comprises a sequence of amino acids as numbered 56, 57, 58, 59, 60, 61, 62, 63, 64 and 65 in a specified sequence.

Selected Definitions

For the purposes of nomenclature only and not limitation an exemplary sequence of a human IL-21 is set out in SEQ ID NO: 1.

The phrase "enhances IL-21 activity" is understood to mean that the antigen binding site of the present invention enhances any one or more activities of naturally occurring IL-21, including but not limited to stimulating proliferation, cytotoxicity or maturation of NK cells, stimulating proliferation or differentiation of B cells and T cells; stimulating antibody production and affinity maturation in B cells; stimulating cytotoxicity of CD8+ T cells; stimulating interferon gamma production in T-cells and NK-cells; inhibiting dendridic cell (DC) activation and maturation; inhibiting release of inflammatory mediators from mast cells, enhancing phagocytosis of macrophages, inhibiting generation or survival of $T_{Reg}$ cells, and stimulating the proliferation of bone marrow progenitor cells.

The term "isolated protein" or "isolated polypeptide" is a protein or polypeptide that by virtue of its origin or source of derivation is not associated with naturally-associated components that accompany it in its native state; is substantially free of other proteins from the same source. A protein may be rendered substantially free of naturally associated components or substantially purified by isolation, using protein purification techniques known in the art. By "substantially purified" is meant the protein is substantially free of contaminating agents, e.g., at least about 70% or 75% or 80% or 85% or 90% or 95% or 96% or 97% or 98% or 99% free of contaminating agents.

The term "recombinant" shall be understood to mean the product of artificial genetic recombination. Accordingly, in the context of a recombinant protein comprising an antibody antigen binding domain, this term does not encompass an antibody naturally-occurring within a subject's body that is the product of natural recombination that occurs during B cell maturation. However, if such an antibody is isolated, it is to be considered an isolated protein comprising an antibody antigen binding domain. Similarly, if nucleic acid encoding the protein is isolated and expressed using recombinant means, the resulting protein is a recombinant protein comprising an antibody antigen binding domain. A recombinant protein also encompasses a protein expressed by artificial recombinant means when it is within a cell, tissue or subject, e.g., in which it is expressed.

The term "protein" shall be taken to include a single polypeptide chain, i.e., a series of contiguous amino acids linked by peptide bonds or a series of polypeptide chains covalently or non-covalently linked to one another (i.e., a polypeptide complex). For example, the series of polypeptide chains can be covalently linked using a suitable chemical or a disulphide bond. Examples of non-covalent bonds include hydrogen bonds, ionic bonds, Van der Waals forces, and hydrophobic interactions.

The term "polypeptide" or "polypeptide chain" will be understood from the foregoing paragraph to mean a series of contiguous amino acids linked by peptide bonds.

As used herein, the term "antigen binding site" is used interchangeably with "antigen binding domain" and shall be taken to mean a region of an antibody that is capable of specifically binding to an antigen, i.e., a $V_H$ or a $V_L$ or an Fv comprising both a $V_H$ and a $V_L$. The antigen binding domain need not be in the context of an entire antibody, e.g., it can be in isolation (e.g., a domain antibody) or in another form, e.g., as described herein, such as a scFv.

For the purposes for the present disclosure, the term "antibody" includes a protein capable of specifically binding to one or a few closely related antigens (e.g., IL-21) by virtue of an antigen binding domain contained within a Fv. This term includes four chain antibodies (e.g., two light chains and two heavy chains), recombinant or modified antibodies (e.g., chimeric antibodies, humanized antibodies, human antibodies, CDR-grafted antibodies, primatized antibodies, de-immunized antibodies, synhumanized antibodies, half-antibodies, bispecific antibodies). An antibody generally comprises constant domains, which can be arranged into a constant region or constant fragment or fragment crystallizable (Fc). Exemplary forms of antibodies comprise a four-chain structure as their basic unit. Full-length antibodies comprise two heavy chains (~50 to 70 kD) covalently linked and two light chains (~23 kDa each). A light chain generally comprises a variable region (if present) and a constant domain and in mammals is either a κ light chain or a λ light chain. A heavy chain generally comprises a variable region and one or two constant domain(s) linked by a hinge region to additional constant domain(s). Heavy chains of mammals are of one of the following types α, δ, ε, γ, or μ. Each light chain is also covalently linked to one of the heavy chains. For example, the two heavy chains and the heavy and light chains are held together by inter-chain disulfide bonds and by non-covalent interactions. The number of inter-chain disulfide bonds can vary among different types of antibodies. Each chain has an N-terminal variable region ($V_H$ or $V_L$ wherein each are ~110 amino acids in length) and one or more constant domains at the C-terminus. The constant domain of the light chain ($C_L$ which is ~110 amino acids in length) is aligned with and disulfide bonded to the first constant domain of the heavy chain ($C_H1$ which is 330 to 440 amino acids in length). The light chain variable region is aligned with the variable region of the heavy chain. The antibody heavy chain can comprise 2 or more additional $C_H$ domains (such as, $C_H2$, $C_H3$ and the like) and can comprise a hinge region between the $C_H1$ and $C_H2$ constant domains. Antibodies can be of any type (e.g., IgG, IgE, IgM, IgD, IgA, and IgY), class (e.g., $IgG_1$, $IgG_2$, $IgG_3$, $IgA_1$, IgA, and $IgA_2$) or subclass. In one example, the antibody is a murine (mouse or rat) antibody or a primate (such as, human) antibody. In one example the antibody heavy chain is missing a C-terminal lysine residue. In one example, the antibody is humanized, synhumanized, chimeric, CDR-grafted or deimmunized.

The terms "full-length antibody," "intact antibody" or "whole antibody" are used interchangeably to refer to an antibody in its substantially intact form, as opposed to an antigen binding fragment of an antibody. Specifically, whole antibodies include those with heavy and light chains including an Fc region. The constant domains may be wild-type sequence constant domains (e.g., human wild-type sequence constant domains) or amino acid sequence variants thereof.

As used herein, "variable region" refers to the portions of the light and/or heavy chains of an antibody as defined herein that is capable of specifically binding to an antigen and, includes amino acid sequences of complementarity determining regions (CDRs); i.e., CDR1, CDR2, and CDR3, and framework regions (FRs). For example, the variable region comprises three or four FRs (e.g., FR1, FR2, FR3 and optionally FR4) together with three CDRs. $V_H$ refers to the variable region of the heavy chain. $V_L$ refers to the variable region of the light chain.

As used herein, the term "complementarity determining regions" (syn. CDRs; i.e., CDR1, CDR2, and CDR3) refers to the amino acid residues of an antibody variable region the presence of which are major contributors to specific antigen binding. Each variable region domain ($V_H$ or $V_L$) typically has three CDRs identified as CDR1, CDR2 and CDR3. In one example, the amino acid positions assigned to CDRs and FRs are defined according to Kabat *Sequences of Proteins of Immunological Interest*, National Institutes of Health, Bethesda, Md., 1987 and 1991 (also referred to herein as "the Kabat numbering system"). In another example, the amino acid positions assigned to CDRs and FRs are defined according to the Enhanced Chothia Numbering Scheme (http://www.bioinfo.org.uk/mdex.html). According to the numbering system of Kabat, $V_H$ FRs and CDRs are positioned as follows: residues 1 to 30 (FR1), 31 to 35 (CDR1), 36 to 49 (FR2), 50 to 65 (CDR2), 66 to 94 (FR3), 95 to 102 (CDR3) and 103 to 113 (FR4). According to the numbering system of Kabat, $V_L$ FRs and CDRs are positioned as follows: residues 1 to 23 (FRI), 24 to 34 (CDR1), 35 to 49 (FR2), 50 to 56 (CDR2), 57 to 88 (FR3), 89 to 97 (CDR3) and 98 to 107 (FR4). The present invention is not limited to FRs and CDRs as defined by the Kabat numbering system, but includes all numbering systems, including the canonical numbering system or of Chothia and Lesk *J. Mol. Biol.* 196: 901-917, 1987; Chothia et al., *Nature* 342: 877-883, 1989; and/or Al-Lazikani et al., *J. Mol. Biol.* 273: 927-948, 1997; the numbering system of Honnegher and Plükthun *J. Mol. Biol.* 309: 657-670, 2001; or the IMGT system discussed in Giudicelli et al., *Nucleic Acids Res.* 25: 206-211 1997. In one example, the CDRs are defined according to the Kabat numbering system. Optionally, heavy chain CDR2 according to the Kabat numbering system does not comprise the five C-terminal amino acids listed herein or any one or more of those amino acids are substituted with another naturally-occurring amino acid. In this regard, Padlan et al., *FASEB J.*, 9: 133-139, 1995 established that the five C-terminal amino acids of heavy chain CDR2 are not generally involved in antigen binding.

"Framework regions" (FRs) are those variable region residues other than the CDR residues.

As used herein, the term "Fv" shall be taken to mean any protein, whether comprised of multiple polypeptides or a single polypeptide, in which a $V_L$ and a $V_H$ associate and form a complex having an antigen binding domain, i.e., capable of specifically binding to an antigen. The $V_H$ and the $V_L$ which form the antigen binding domain can be in a single polypeptide chain or in different polypeptide chains. Furthermore, an Fv of the invention (as well as any protein of the invention) may have multiple antigen binding domains which may or may not bind the same antigen. This term shall be understood to encompass fragments directly derived from an antibody as well as proteins corresponding to such a fragment produced using recombinant means. In some examples, the $V_H$ is not linked to a heavy chain constant domain ($C_H$) 1 and/or the $V_L$ is not linked to a light chain constant domain ($C_L$). Exemplary Fv containing polypeptides or proteins include a Fab fragment, a Fab' fragment, a F(ab') fragment, a scFv, a diabody, a triabody, a tetrabody or higher order complex, or any of the foregoing linked to a constant region or domain thereof, e.g., $C_H2$ or $C_H3$ domain, e.g., a minibody. A "Fab fragment" consists of a monovalent antigen-binding fragment of an immunoglobulin, and can be produced by digestion of a whole antibody with the enzyme papain, to yield a fragment consisting of an intact light chain and a portion of a heavy chain or can be produced using recombinant means. A "Fab' fragment" of an antibody can be obtained by treating a whole antibody with pepsin, followed by reduction, to yield a molecule consisting of an intact light chain and a portion of a heavy chain comprising a $V_H$ and a single constant domain. Two Fab' fragments are obtained per antibody treated in this manner. A Fab' fragment can also be produced by recombinant means. A "F(ab')2 fragment" of an antibody consists of a dimer of two Fab' fragments held together by two disulfide bonds, and is obtained by treating a whole antibody molecule with the enzyme pepsin, without subsequent reduction. A "Fab$_2$" fragment is a recombinant fragment comprising two Fab fragments linked using, for example a leucine zipper or a $C_H3$ domain. A "single chain Fv" or "scFv" is a recombinant molecule containing the variable region fragment (Fv) of an antibody in which the variable region of the light chain and the variable region of the heavy chain are covalently linked by a suitable, flexible polypeptide linker.

As used herein, the term "binds" in reference to the interaction of an antigen binding site or an antigen binding domain thereof with an antigen means that the interaction is dependent upon the presence of a particular structure (e.g., an antigenic determinant or epitope) on the antigen. For example, an antibody recognizes and binds to a specific protein structure rather than to proteins generally. If an antibody binds to epitope "A", the presence of a molecule containing epitope "A" (or free, unlabeled "A"), in a reaction containing labeled "A" and the protein, will reduce the amount of labeled "A" bound to the antibody.

As used herein, the term "specifically binds" or "binds specifically" shall be taken to mean that an antigen binding site of the invention reacts or associates more frequently, more rapidly, with greater duration and/or with greater affinity with a particular antigen or cell expressing same than it does with alternative antigens or cells. For example, an antigen binding site binds to IL-21 (e.g., hIL-21) with materially greater affinity (e.g., 1.5 fold or 2 fold or 5 fold or 10 fold or 20 fold or 40 fold or 60 fold or 80 fold to 100 fold or 150 fold or 200 fold) than it does to other interleukins or to antigens commonly recognized by polyreactive natural antibodies (i.e., by naturally occurring antibodies known to bind a variety of antigens naturally found in humans). In an example of the present invention, an antigen binding site that "specifically binds" to hIL-21 with an affinity at least 1.5 fold or 2 fold or greater (e.g., 5 fold or 10 fold or 20 fold r 50 fold or 100 fold or 200 fold) than it does to another interleukin. Generally, but not necessarily, reference to binding means specific binding, and each term shall be understood to provide explicit support for the other term.

As used herein, the term "does not detectably bind" shall be understood to mean that an antigen binding site, e.g., an antibody, binds to a candidate antigen at a level less than 10%, or 8% or 6% or 5% above background. The background can be the level of binding signal detected in the absence of the protein and/or in the presence of a negative control protein (e.g., an isotype control antibody) and/or the level of binding detected in the presence of a negative control antigen. The level of binding is detected using biosensor analysis (e.g. Biacore) in which the antigen binding site is immobilized and contacted with an antigen.

As used herein, the term "does not significantly bind" shall be understood to mean that the level of binding of an antigen binding site of the invention to a polypeptide is not statistically significantly higher than background, e.g., the level of binding signal detected in the absence of the antigen binding site and/or in the presence of a negative control protein (e.g., an isotype control antibody) and/or the level of binding detected in the presence of a negative control polypeptide. The level of binding is detected using biosensor analysis (e.g. Biacore) in which the IL-21 binding protein is immobilized and contacted with an antigen.

For the purposes of clarification and as will be apparent to the skilled artisan based on the exemplified subject matter herein, reference to "affinity" in this specification is a reference to $K_D$ of a protein or antibody.

For the purposes of clarification and as will be apparent to the skilled artisan based on the description herein, reference to an "affinity of at least about" will be understood to mean that the affinity (or $K_D$) is equal to the recited value or higher (i.e., the value recited as the affinity is lower), i.e., an affinity of 2 nM is greater than an affinity of 3 nM. Stated another way, this term could be "an affinity of X or less", wherein X is a value recited herein.

As used herein, the term "epitope" (syn. "antigenic determinant") shall be understood to mean a region of IL-21 to which an antigen binding site comprising an antigen binding domain of an antibody binds. This term is not necessarily limited to the specific residues or structure to which the antigen binding site makes contact. For example, this term includes the region spanning amino acids contacted by the antigen binding site and 5-10 (or more) or 2-5 or 1-3 amino acids outside of this region. In some examples, the epitope comprises a series of discontinuous amino acids that are positioned close to one another when antigen binding site is folded, i.e., a "conformational epitope". The skilled artisan will also be aware that the term "epitope" is not limited to peptides or polypeptides. For example, the term "epitope" includes chemically active surface groupings of molecules such as sugar side chains, phosphoryl side chains, or sulfonyl side chains, and, in certain examples, may have specific three dimensional structural characteristics, and/or specific charge characteristics.

The term "competitively inhibits" shall be understood to mean that an antigen binding site of the invention (or an antigen binding domain thereof) reduces or prevents binding of a recited antibody or antigen binding site to IL-21, e.g., to hIL-21. This may be due to the antigen binding site (or antigen binding domain) and antibody binding to the same or an overlapping epitope. It will be apparent from the foregoing that the antigen binding site need not completely inhibit binding of the antibody, rather it need only reduce binding by a statistically significant amount, for example, by at least about 10% or 20% or 30% or 40% or 50% or 60% or 70% or 80% or 90% or 95%. Preferably, the antigen binding site reduces binding of the antibody by at least about 30%, more preferably by at least about 50%, more preferably, by at least about 70%, still more preferably by at least about 75%, even more preferably, by at least about 80% or 85% and even more preferably, by at least about 90%. Methods for determining competitive inhibition of binding are known in the art and/or described herein. For example, the antibody is exposed to IL-21 either in the presence or absence of the antigen binding site. If less antibody binds in the presence of the antigen binding site than in the absence of the antigen binding site, the protein is considered to competitively inhibit binding of the antibody. In one example, the competitive inhibition is not due to steric hindrance.

"Overlapping" in the context of two epitopes shall be taken to mean that two epitopes share a sufficient number of amino acid residues to permit an antigen binding site (or antigen binding domain thereof) that binds to one epitope to competitively inhibit the binding of an antigen binding site (or antigen binding domain) that binds to the other epitope. For example, the "overlapping" epitopes share at least 1 or 2 or 3 or 4 or 5 or 6 or 7 or 8 or 9 or 20 amino acids.

As used herein, the term "agonize" shall be taken to mean that a protein is capable of enhancing IL-21-mediated signaling in a cell. Methods for determining enhanced activity are known in the art and/or described herein.

As used herein, the term "condition" refers to a disruption of or interference with normal function, and is not to be limited to any specific condition, and will include diseases or disorders.

As used herein, the terms "preventing", "prevent" or "prevention" include administering an antigen binding site of the invention to thereby stop or hinder the development of at least one symptom of a condition. This term also encompasses treatment of a subject in remission to prevent or hinder relapse.

As used herein, the terms "treating", "treat" or "treatment" include administering an antigen binding site described herein to thereby reduce or eliminate at least one symptom of a specified disease or condition.

As used herein, the term "subject" shall be taken to mean any animal including humans, for example a mammal. Exemplary subjects include but are not limited to humans and non-human primates. For example, the subject is a human.

Antibodies

In one example, an antigen binding site or IL-21-binding protein as described herein according to any example is an antibody.

Methods for generating antibodies are known in the art and/or described in Harlow and Lane (editors) Antibodies: A Laboratory Manual, Cold Spring Harbor Laboratory, (1988). Generally, in such methods IL-21 (e.g., hIL-21) or a region thereof (e.g., an extracellular region) or immunogenic fragment or epitope thereof or a cell expressing and displaying same (i.e., an immunogen), optionally formulated with any suitable or desired carrier, adjuvant, or pharmaceutically acceptable excipient, is administered to a non-human animal, for example, a mouse, chicken, rat, rabbit, guinea pig, dog, horse, cow, goat or pig. The immunogen may be administered intranasally, intramuscularly, sub-cutaneously, intravenously, intradermally, intraperitoneally, or by other known route.

The production of polyclonal antibodies may be monitored by sampling blood of the immunized animal at various points following immunization. One or more further immunizations may be given, if required to achieve a desired antibody titer. The process of boosting and titering is repeated until a suitable titer is achieved. When a desired level of immunogenicity is obtained, the immunized animal is bled and the serum isolated and stored, and/or the animal is used to generate monoclonal antibodies (mAbs).

Monoclonal antibodies are one exemplary form of antibody contemplated by the present invention. The term "monoclonal antibody" or "mAb" refers to a homogeneous antibody population capable of binding to the same antigen(s), for example, to the same epitope within the antigen. This term is not intended to be limited with regard to the source of the antibody or the manner in which it is made.

For the production of mAbs any one of a number of known techniques may be used, such as, for example, the procedure exemplified in U.S. Pat. No. 4,196,265 or Harlow and Lane (1988), supra.

For example, a suitable animal is immunized with an immunogen under conditions sufficient to stimulate antibody producing cells. Rodents such as rabbits, mice and rats are exemplary animals. Mice genetically-engineered to express human antibodies, for example, which do not express murine antibodies, can also be used to generate an antibody of the present invention (e.g., as described in WO2002/066630).

Following immunization, somatic cells with the potential for producing antibodies, specifically B lymphocytes (B cells), are selected for use in the mAb generating protocol. These cells may be obtained from biopsies of spleens, tonsils or lymph nodes, or from a peripheral blood sample. The B cells from the immunized animal are then fused with cells of an immortal myeloma cell, generally derived from the same species as the animal that was immunized with the immunogen.

Hybrids are amplified by culture in a selective medium comprising an agent that blocks the de novo synthesis of nucleotides in the tissue culture media. Exemplary agents are aminopterin, methotrexate and azaserine.

The amplified hybridomas are subjected to a functional selection for antibody specificity and/or titer, such as, for example, by flow cytometry and/or immunohistochemstry and/or immunoassay (e.g. radioimmunoassay, enzyme immunoassay, cytotoxicity assay, plaque assay, dot immunoassay, and the like).

Alternatively, ABL-MYC technology (NeoClone, Madison Wis. 53713, USA) is used to produce cell lines secreting MAbs (e.g., as described in Largaespada et al, *J. Immunol. Methods.* 197: 85-95, 1996).

Antibodies can also be produced or isolated by screening a display library, e.g., a phage display library, e.g., as described in U.S. Pat. No. 6,300,064 and/or U.S. Pat. No. 5,885,793. For example, the present inventors have isolated fully human antibodies from a phage display library.

The antibody of the present invention may be a synthetic antibody. For example, the antibody is a chimeric antibody, a humanized antibody, a human antibody synhumanized antibody, primatized antibody or a de-immunized antibody.

The amino acid sequence of the VH of h2P2 is:

Gln Val Gln Leu Val Gln Ser Gly Ala Glu Val Lys

Lys Pro Gly Ala Ser Val Lys Val Ser Cys Lys Ala

Ser Gly Phe Asn Ile Lys Asp Tyr Tyr Ile His Trp

Val Arg Gln Ala Pro Gly Gln Gly Leu Glu Leu Ile

```
Gly Trp Ile Asp Pro Glu Ser Gly Asp Thr Asn Tyr

Ala Gln Lys Phe Gln Val Lys Ala Thr Met Thr Arg

Asp Thr Ser Ile Ser Thr Ala Tyr Met Glu Leu Ser

Arg Leu Arg Ser Asp Asp Thr Ala Val Tyr Tyr Cys

Asn Asp Gly Ser Gly Tyr Trp Gly Gln Gly Thr Thr

Val Thr Val Ser Ser
```

The amino acid sequence of the VL of h2P2 is:

```
Asp Val Val Met Thr Gln Ser Pro Leu Ser Leu Pro

Val Thr Leu Gly Gln Pro Ala Ser Ile Ser Cys Lys

Ser Ser Gln Ser Leu Leu Asp Ser Asp Gly Glu Thr

Tyr Leu Asn Trp Leu Gln Gln Arg Pro Gly Gln Ser

Pro Arg Arg Leu Ile Ser Leu Val Ser Lys Leu Asp

Ser Gly Val Pro Asp Arg Phe Ser Gly Ser Gly Ser

Gly Thr Asp Phe Thr Leu Lys Ile Ser Arg Val Glu

Ala Glu Asp Val Gly Val Tyr Tyr Cys Trp Gln Gly

Thr His Phe Pro Tyr Thr Phe Gly Gln Gly Thr Lys

Leu Glu Ile Lys
```

Deimmunized, Chimeric, CDR Grafted, Humanized, Synhumanized, Primatized, Human and Composite IL-21-Binding Proteins The antigen binding sites of the present invention may be CDR grafted proteins which include CDRs from an antibody from a non-human species (e.g., mouse or rat or non-human primate) grafted onto or inserted into FRs from a human antibody or which include CDRs from an antibody from one type of antibody (e.g., one type of human antibody) grafted onto or inserted into FRs from another type of antibody (e.g., another type of human antibody). This term also encompasses a composite antigen binding site comprising, for example, one or more CDR grafted variable regions and one or more, e.g., human variable regions, chimeric variable regions, synhumanized variable regions or primatized variable regions.

The antigen binding sites of the present invention may be a humanized protein.

The term "humanized protein" shall be understood to refer to a protein comprising a human-like variable region, which includes CDRs from an antibody from a non-human species (e.g., mouse or rat or non-human primate) grafted onto or inserted into FRs from a human antibody (this type of antibody is falls within the class of "CDR-grafted antibody"). Humanized antigen binding sites also include proteins in which one or more residues of the human protein are modified by one or more amino acid substitutions and/or one or more FR residues of the human protein are replaced by corresponding non-human residues. Humanized proteins may also comprise residues which are found in neither the human antibody or in the non-human antibody. Any additional regions of the protein (e.g., Fc region) are generally human. Humanization can be performed using a method known in the art, e.g., U.S. Pat. Nos. 5,225,539, 6,054,297, 7,566,771 or U.S. Pat. No. 5,585,089. The term "humanized protein" also encompasses a super-humanized protein, e.g., as described in U.S. Pat. No. 7,732,578. This term also encompasses a composite protein comprising, for example, one or more humanized variable regions and one or more, e.g., human variable regions, chimeric variable regions, synhumanized variable regions or primatized variable regions.

The antigen binding sites of the present invention may be human antigen binding sites. The term "human protein" as used herein refers to proteins having variable and, optionally, constant antibody regions found in humans, e.g. in the human germline or somatic cells or from libraries produced using such regions. The "human" proteins can include amino acid residues not encoded by human sequences, e.g. mutations introduced by random or site directed mutations in vitro (in particular mutations which involve conservative substitutions or mutations in a small number of residues of the protein, e.g. in 1, 2, 3, 4 or 5 of the residues of the protein). These "human proteins" do not necessarily need to be generated as a result of an immune response of a human, rather, they can be generated using recombinant means (e.g., screening a phage display library) and/or by a transgenic animal (e.g., a mouse) comprising nucleic acid encoding human antibody constant and/or variable regions and/or using guided selection (e.g., as described in U.S. Pat. No. 5,565,332). This term also encompasses affinity matured forms of such antibodies. For the purposes of the present disclosure, a human protein will also be considered to include a protein comprising FRs from a human antibody or FRs comprising sequences from a consensus sequence of human FRs and in which one or more of the CDRs are random or semi-random, e.g., as described in U.S. Pat. No. 6,300,064 and/or U.S. Pat. No. 6,248,516.

Optionally, the $V_H$ is linked to a heavy chain constant region, e.g., an IgG4 heavy chain constant region. In one example, the heavy chain constant region lacks the C-terminal lysine residue.

Optionally, the $V_L$ is linked to a light chain constant region.

The antigen binding sites of the present invention may be synhumanized proteins. The term "synhumanized protein" refers to a protein prepared by a method described in WO2007/019620. A synhumanized antigen binding site includes a variable region of an antibody, wherein the variable region comprises FRs from a New World primate antibody variable region and CDRs from a non-New World primate antibody variable region. For example, a synhumanized antigen binding site includes a variable region of an antibody, wherein the variable region comprises FRs from a New World primate antibody variable region and CDRs from a mouse or rat antibody. In one example, the synhumanized antigen binding site is a IL-21-binding antibody in which one or both of the variable regions are synhumanized. This term also encompasses a composite protein comprising, for example, one or more synhumanized variable regions and one or more, e.g., human variable regions or humanized variable regions or chimeric variable regions.

The antigen binding sites of the present invention may be primatized proteins. A "primatized protein" comprises variable region(s) from an antibody generated following immunization of a non-human primate (e.g., a cynomolgus macaque). Optionally, the variable regions of the non-human primate antibody are linked to human constant regions to produce a primatized antibody. Exemplary methods for producing primatized antibodies are described in U.S. Pat. No. 6,113,898. This term also encompasses a composite protein comprising, for example, one or more primatized variable regions and one or more, e.g., human variable regions or humanized variable regions or chimeric variable regions.

In one example an antigen binding site of the invention is a chimeric protein. The term "chimeric proteins" refers to proteins in which an antigen binding domain is from a particular species (e.g., murine, such as mouse or rat) or belonging to a particular antibody class or subclass, while the remainder of the protein is from a protein derived from another species (such as, for example, human or non-human primate) or belonging to another antibody class or subclass. In one example, a chimeric protein is a chimeric antibody comprising a $V_H$ and/or a $V_L$ from a non-human antibody (e.g., a murine antibody) and the remaining regions of the antibody are from a human antibody. The production of such chimeric proteins is known in the art, and may be achieved by standard means (as described, e.g., in U.S. Pat. Nos. 6,331,415; 5,807,715; 4,816,567 and 4,816,397). This term also encompasses a composite protein comprising, for example, one or more chimeric variable regions and one or more, e.g., human variable regions or humanized variable regions or chimeric variable regions.

The present invention also contemplates a deimmunized antigen binding site, e.g., as described in WO2000/34317 and WO2004/108158. De-immunized antibodies and proteins have one or more epitopes, e.g., B cell epitopes or T cell epitopes removed (i.e., mutated) to thereby reduce the likelihood that a subject will raise an immune response against the antibody or protein. For example, an antigen binding site of the invention is analyzed to identify one or more B or T cell epitopes and one or more amino acid residues within the epitope is mutated to thereby reduce the immunogenicity of the antigen binding site.

It will be apparent to the skilled artisan from the foregoing disclosure that a "composite" protein comprises one form of $V_H$ (e.g., human) and another form of $V_L$ (e.g., humanized). The present invention explicitly encompasses all combinations of forms of $V_H$ and $V_L$.

Determination of Complementarity Determining Regions

The complementarity determining regions (CDRs) disclosed herein are based, in one example, on the numbering system of Lefranc and colleagues, referred to as the ImMunoGeneTics (IMGT) numbering system (Lefranc, Marie-Paule et al (1999) Nucl. Acids. Res. 27(1):209-212) which is a unified numbering system for immunoglobulin variable domain germ line sequences including antibody lambda and kappa light and heavy chain variable domains as well as T-cell receptor alpha, beta, gamma and delta chain variable domains.

Persons skilled in the art will appreciate that CDRs can also be determined using the numbering system of Kabat et al. (Kabat et al., Sequences of Proteins of Immunological Interest Washington D.C. United States Department of Health and Human Services, 1987 and/or 1991). Accordingly, the present invention also encompasses antigen binding sites comprising an antigen binding domain of an antibody wherein the antigen-binding domain comprises heavy and light chain complementarity determining region sequences as described above according to the Kabat numbering system.

Antibody Binding Domain Containing Proteins

Single-Domain Antibodies

In some examples, a protein of the invention is or comprises a single-domain antibody (which is used interchangeably with the term "domain antibody" or "dAb"). A single-domain antibody is a single polypeptide chain comprising all or a portion of the heavy chain variable region of an antibody. In certain examples, a single-domain antibody is a human single-domain antibody (Domantis, Inc., Waltham, Mass.; see, e.g., U.S. Pat. No. 6,248,516).

Diabodies, Triabodies, Tetrabodies

In some examples, a protein of the invention is or comprises a diabody, triabody, tetrabody or higher order protein complex such as those described in WO98/044001 and/or WO94/007921.

For example, a diabody is a protein comprising two associated polypeptide chains, each polypeptide chain comprising the structure $V_L$-X-$V_H$ or $V_H$-X-$V_L$, wherein $V_L$ is an antibody light chain variable region, $V_H$ is an antibody heavy chain variable region, X is a linker comprising insufficient residues to permit the $V_H$ and $V_L$ in a single polypeptide chain to associate (or form an Fv) or is absent, and wherein the $V_H$ of one polypeptide chain binds to a $V_L$ of the other polypeptide chain to form an antigen binding domain, i.e., to form a Fv molecule capable of specifically binding to one or more antigens. The $V_L$ and $V_H$ can be the same in each polypeptide chain or the $V_L$ and $V_H$ can be different in each polypeptide chain so as to form a bispecific diabody (i.e., comprising two Fvs having different specificity).

Single Chain Fv (scFv)

The skilled artisan will be aware that scFvs comprise $V_H$ and $V_L$ regions in a single polypeptide chain and a polypeptide linker between the $V_H$ and $V_L$ which enables the scFv to form the desired structure for antigen binding (i.e., for the $V_H$ and $V_L$ of the single polypeptide chain to associate with one another to form a Fv). For example, the linker comprises in excess of 12 amino acid residues with $(Gly_4Ser)_3$ being one of the more favored linkers for a scFv.

The present invention also contemplates a disulfide stabilized Fv (or diFv or dsFv), in which a single cysteine residue is introduced into a FR of $V_H$ and a FR of $V_L$ and the cysteine residues linked by a disulfide bond to yield a stable Fv.

Alternatively, or in addition, the present invention encompasses a dimeric scFv, i.e., a protein comprising two scFv molecules linked by a non-covalent or covalent linkage, e.g., by a leucine zipper domain (e.g., derived from Fos or Jun). Alternatively, two scFvs are linked by a peptide linker of sufficient length to permit both scFvs to form and to bind to an antigen, e.g., as described in US20060263367.

Heavy Chain Antibodies

Heavy chain antibodies differ structurally from many other forms of antibodies, in so far as they comprise a heavy chain, but do not comprise a light chain. Accordingly, these antibodies are also referred to as "heavy chain only antibodies". Heavy chain antibodies are found in, for example, camelids and cartilaginous fish (also called IgNAR).

The variable regions present in naturally occurring heavy chain antibodies are generally referred to as "$V_{HH}$ domains" in camelid antibodies and V-NAR in IgNAR, in order to distinguish them from the heavy chain variable regions that are present in conventional 4-chain antibodies (which are referred to as "$V_H$ domains") and from the light chain variable regions that are present in conventional 4-chain antibodies (which are referred to as "$V_L$ domains").

A general description of heavy chain antibodies from camelids and the variable regions thereof and methods for their production and/or isolation and/or use is found inter alia in the following references WO94/04678, WO97/49805 and WO 97/49805.

A general description of heavy chain antibodies from cartilaginous fish and the variable regions thereof and methods for their production and/or isolation and/or use is found inter alia in WO2005/118629.

Other Antibodies and Proteins Comprising Antigen Binding Domains Thereof

The present invention also contemplates other antibodies and proteins comprising antigen-binding domains thereof, such as:

(i) "key and hole" bispecific proteins as described in U.S. Pat. No. 5,731,168;

(ii) heteroconjugate proteins, e.g., as described in U.S. Pat. No. 4,676,980;

(iii) heteroconjugate proteins produced using a chemical cross-linker, e.g., as described in U.S. Pat. No. 4,676,980; and (iv) $Fab_3$ (e.g., as described in EP19930302894).

Mutations to Proteins

The present invention also provides an antigen binding site or a nucleic acid encoding same having at least 80% identity to a sequence disclosed herein. In one example, a antigen binding site or nucleic acid of the invention comprises sequence at least about 85% or 90% or 95% or 97% or 98% or 99% identical to a sequence disclosed herein.

Alternatively, or additionally, the antigen binding site comprises a CDR (e.g., three CDRs) at least about 80% or 85% or 90% or 95% or 97% or 98% or 99% identical to CDR(s) of a $V_H$ or $V_L$ as described herein according to any example.

In another example, a nucleic acid of the invention comprises a sequence at least about 80% or 85% or 90% or 95% or 97% or 98% or 99% identical to a sequence encoding an antigen binding site having a function as described herein according to any example. The present invention also encompasses nucleic acids encoding an antigen binding site of the invention, which differs from a sequence exemplified herein as a result of degeneracy of the genetic code.

The % identity of a nucleic acid or polypeptide is determined by GAP (Needleman and Wunsch. *Mol. Biol.* 48, 443-453, 1970) analysis (GCG program) with a gap creation penalty=5, and a gap extension penalty=0.3. The query sequence is at least 50 residues in length, and the GAP analysis aligns the two sequences over a region of at least 50 residues. For example, the query sequence is at least 100 residues in length and the GAP analysis aligns the two sequences over a region of at least 100 residues. For example, the two sequences are aligned over their entire length.

The present invention also contemplates a nucleic acid that hybridizes under stringent hybridization conditions to a nucleic acid encoding an antigen binding site described herein. A "moderate stringency" is defined herein as being a hybridization and/or washing carried out in 2×SSC buffer, 0.1% (w/v) SDS at a temperature in the range 45° C. to 65° C., or equivalent conditions. A "high stringency" is defined herein as being a hybridization and/or wash carried out in 0.1×SSC buffer, 0.1% (w/v) SDS, or lower salt concentration, and at a temperature of at least 65° C., or equivalent conditions. Reference herein to a particular level of stringency encompasses equivalent conditions using wash/hybridization solutions other than SSC known to those skilled in the art. For example, methods for calculating the temperature at which the strands of a double stranded nucleic acid will dissociate (also known as melting temperature, or Tm) are known in the art. A temperature that is similar to (e.g., within 5° C. or within 10° C.) or equal to the Tm of a nucleic acid is considered to be high stringency. Medium stringency is to be considered to be within 10° C. to 20° C. or 10° C. to 15° C. of the calculated Tm of the nucleic acid.

The present invention also contemplates mutant forms of an antigen binding site of the invention comprising one or more conservative amino acid substitutions compared to a sequence set forth herein. In some examples, the antigen binding site comprises 10 or fewer, e.g., 9 or 8 or 7 or 6 or 5 or 4 or 3 or 2 or 1 conservative amino acid substitutions. A "conservative amino acid substitution" is one in which the amino acid residue is replaced with an amino acid residue having a similar side chain and/or hydropathicity and/or hydrophilicity.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Hydropathic indices are described, for example in Kyte and Doolittle *J. Mol. Biol.*, 157: 105-132, 1982 and hydrophylic indices are described in, e.g., U.S. Pat. No. 4,554,101.

The present invention also contemplates non-conservative amino acid changes. For example, of particular interest are substitutions of charged amino acids with another charged amino acid and with neutral or positively charged amino acids. In some examples, the antigen binding site comprises 10 or fewer, e.g., 9 or 8 or 7 or 6 or 5 or 4 or 3 or 2 or 1 non-conservative amino acid substitutions.

In one example, the mutation(s) occur within a FR of an antigen binding domain of an antigen binding site of the invention. In another example, the mutation(s) occur within a CDR of an antigen binding site of the invention.

Exemplary methods for producing mutant forms of an antigen binding site include:

mutagenesis of DNA (Thie et al., *Methods Mol. Biol.* 525: 309-322, 2009) or RNA (Kopsidas et al., *Immunol. Lett.* 107:163-168, 2006; Kopsidas et al. *BMC Biotechnology*, 7: 18, 2007; and WO1999/058661);

introducing a nucleic acid encoding the polypeptide into a mutator cell, e.g., XL-1Red, XL-mutS and XL-mutS-Kanr bacterial cells (Stratagene);

DNA shuffling, e.g., as disclosed in Stemmer, *Nature* 370: 389-91, 1994; and site directed mutagenesis, e.g., as described in Dieffenbach (ed) and Dveksler (ed) (In: PCR Primer: A Laboratory Manual, Cold Spring Harbor Laboratories, N Y, 1995).

Exemplary methods for determining biological activity of the mutant antigen binding sites of the invention will be apparent to the skilled artisan and/or described herein, e.g., antigen binding. For example, methods for determining antigen binding, competitive inhibition of binding, affinity, association, dissociation and therapeutic efficacy are described herein.

Constant Regions

The present invention encompasses antigen binding sites and/or antibodies described herein comprising a constant region of an antibody. This includes antigen binding fragments of an antibody fused to an Fc.

Sequences of constant regions useful for producing the proteins of the present invention may be obtained from a number of different sources. In some examples, the constant region or portion thereof of the protein is derived from a human antibody. The constant region or portion thereof may be derived from any antibody class, including IgM, IgG, IgD, IgA and IgE, and any antibody isotype, including IgG1, IgG2, IgG3 and IgG4. In one example, the constant region is human isotype IgG4 or a stabilized IgG4 constant region.

In one example, the Fc region of the constant region has a reduced ability to induce effector function, e.g., compared to a native or wild-type human IgG1 or IgG3 Fc region. In one example, the effector function is antibody-dependent cell-mediated cytotoxicity (ADCC) and/or antibody-dependent cell-mediated phagocytosis (ADCP) and/or complement-dependent cytotoxicity (CDC). Methods for assessing the level of effector function of an Fc region containing protein are known in the art and/or described herein.

In one example, the Fc region is an IgG4 Fc region (i.e., from an IgG4 constant region), e.g., a human IgG4 Fc region. Sequences of suitable IgG4 Fc regions will be apparent to the skilled person and/or available in publically available databases (e.g., available from National Center for Biotechnology Information).

In one example, the constant region is a stabilized IgG4 constant region. The term "stabilized IgG4 constant region" will be understood to mean an IgG4 constant region that has been modified to reduce Fab arm exchange or the propensity to undergo Fab arm exchange or formation of a half-antibody or a propensity to form a half antibody. "Fab arm exchange" refers to a type of protein modification for human IgG4, in which an IgG4 heavy chain and attached light chain (half-molecule) is swapped for a heavy-light chain pair from another IgG4 molecule. Thus, IgG4 molecules may acquire two distinct Fab arms recognizing two distinct antigens (resulting in bispecific molecules). Fab arm exchange occurs naturally in vivo and can be induced in vitro by purified blood cells or reducing agents such as reduced glutathione. A "half antibody" forms when an IgG4 antibody dissociates to form two molecules each containing a single heavy chain and a single light chain.

In one example, a stabilized IgG4 constant region comprises a proline at position 241 of the hinge region according to the system of Kabat (Kabat et al., Sequences of Proteins of Immunological Interest Washington D.C. United States Department of Health and Human Services, 1987 and/or 1991). This position corresponds to position 228 of the hinge region according to the EU numbering system (Kabat et al., Sequences of Proteins of Immunological Interest Washington D.C. United States Department of Health and Human Services, 2001 and Edelman et al., Proc. Natl. Acad. USA, 63, 78-85, 1969). In human IgG4, this residue is generally a serine. Following substitution of the serine for proline, the IgG4 hinge region comprises a sequence CPPC. In this regard, the skilled person will be aware that the "hinge region" is a proline-rich portion of an antibody heavy chain constant region that links the Fc and Fab regions that confers mobility on the two Fab arms of an antibody. The hinge region includes cysteine residues which are involved in inter-heavy chain disulfide bonds. It is generally defined as stretching from Glu226 to Pro243 of human IgG1 according to the numbering system of Kabat. Hinge regions of other IgG isotypes may be aligned with the IgG1 sequence by placing the first and last cysteine residues forming inter-heavy chain disulphide (S—S) bonds in the same positions (see for example WO2010/080538).

Additional examples of stabilized IgG4 antibodies are antibodies in which arginine at position 409 in a heavy chain constant region of human IgG4 (according to the EU numbering system) is substituted with lysine, threonine, methionine, or leucine (e.g., as described in WO2006/033386). The Fc region of the constant region may additionally or alternatively comprise a residue selected from the group consisting of: alanine, valine, glycine, isoleucine and leucine at the position corresponding to 405 (according to the EU numbering system). Optionally, the hinge region comprises a proline at position 241 (i.e., a CPPC sequence) (as described above).

In another example, the Fc region is a region modified to have reduced effector function, i.e., a "non-immunostimulatory Fc region". For example, the Fc region is an IgG1 Fc region comprising a substitution at one or more positions selected from the group consisting of 268, 309, 330 and 331. In another example, the Fc region is an IgG1 Fc region comprising one or more of the following changes E233P, L234V, L235A and deletion of G236 and/or one or more of the following changes A327G, A330S and P331S (Armour et al., Eur J Immunol. 29:2613-2624, 1999; Shields et al., J Biol Chem. 276(9):6591-604, 2001). Additional examples of non-immunostimulatory Fc regions are described, for example, in Dall'Acqua et al., J Immunol. 177: 1129-1138 2006; and/or Hezareh J Virol; 75: 12161-12168, 2001).

In another example, the Fc region is a chimeric Fc region, e.g., comprising at least one $C_H2$ domain from an IgG4 antibody and at least one $C_H3$ domain from an IgG1 antibody, wherein the Fc region comprises a substitution at one or more amino acid positions selected from the group consisting of 240, 262, 264, 266, 297, 299, 307, 309, 323, 399, 409 and 427 (EU numbering) (e.g., as described in WO2010/085682). Exemplary substitutions include 240F, 262L, 264T, 266F, 297Q, 299A, 299K, 307P, 309K, 309M, 309P, 323F, 399S, and 427F.

Additional Modifications

The present invention also contemplates additional modifications to an antibody or antigen binding site comprising an Fc region or constant region.

For example, the antibody comprises one or more amino acid substitutions that increase the half-life of the protein. For example, the antibody comprises a Fc region comprising one or more amino acid substitutions that increase the affinity of the Fc region for the neonatal Fc region (FcRn). For example, the Fc region has increased affinity for FcRn at lower pH, e.g., about pH 6.0, to facilitate Fc/FcRn binding in an endosome. In one example, the Fc region has increased affinity for FcRn at about pH 6 compared to its affinity at about pH 7.4, which facilitates the re-release of Fc into blood following cellular recycling. These amino acid substitutions are useful for extending the half life of a protein, by reducing clearance from the blood.

Exemplary amino acid substitutions include T250Q and/or M428L or T252A, T254S and T266F or M252Y, S254T and T256E or H433K and N434F according to the EU numbering system. Additional or alternative amino acid substitutions are described, for example, in US20070135620 or U.S. Pat. No. 7,083,784.

Protein Production

In one example, an antigen binding site described herein according to any example is produced by culturing a hybridoma under conditions sufficient to produce the protein, e.g., as described herein and/or as is known in the art.

Recombinant Expression

In another example, an antigen binding site described herein according to any example is recombinant.

In the case of a recombinant protein, nucleic acid encoding same can be cloned into expression constructs or vectors, which are then transfected into host cells, such as E. coli cells, yeast cells, insect cells, or mammalian cells, such as simian COS cells, Chinese Hamster Ovary (CHO) cells, human embryonic kidney (HEK) cells, or myeloma cells that do not otherwise produce the protein. Exemplary cells used for expressing a protein are CHO cells, myeloma cells or HEK cells. Molecular cloning techniques to achieve these ends are known in the art and described, for example in Ausubel et al., (editors), Current Protocols in Molecular Biology, Greene Pub. Associates and Wiley-Interscience (1988, including all updates until present) or Sambrook et al., Molecular Cloning: A Laboratory Manual, Cold Spring Harbor Laboratory Press (1989). A wide variety of cloning and in vitro amplification methods are suitable for the construction of recombinant nucleic acids. Methods of producing recombinant antibodies are also known in the art, see, e.g., U.S. Pat. No. 4,816,567 or U.S. Pat. No. 5,530,101.

Following isolation, the nucleic acid is inserted operably linked to a promoter in an expression construct or expression vector for further cloning (amplification of the DNA) or for expression in a cell-free system or in cells.

As used herein, the term "promoter" is to be taken in its broadest context and includes the transcriptional regulatory sequences of a genomic gene, including the TATA box or initiator element, which is required for accurate transcription initiation, with or without additional regulatory elements (e.g., upstream activating sequences, transcription factor binding sites, enhancers and silencers) that alter expression of a nucleic acid, e.g., in response to a developmental and/or external stimulus, or in a tissue specific manner. In the present context, the term "promoter" is also used to describe a recombinant, synthetic or fusion nucleic acid, or derivative which confers, activates or enhances the expression of a nucleic acid to which it is operably linked. Exemplary promoters can contain additional copies of one or more specific regulatory elements to further enhance expression and/or alter the spatial expression and/or temporal expression of said nucleic acid.

As used herein, the term "operably linked to" means positioning a promoter relative to a nucleic acid such that expression of the nucleic acid is controlled by the promoter.

Many vectors for expression in cells are available. The vector components generally include, but are not limited to, one or more of the following: a signal sequence, a sequence encoding a protein (e.g., derived from the information provided herein), an enhancer element, a promoter, and a transcription termination sequence. The skilled artisan will be aware of suitable sequences for expression of a protein. Exemplary signal sequences include prokaryotic secretion signals (e.g., pelB, alkaline phosphatase, penicillinase, Ipp, or heat-stable enterotoxin II), yeast secretion signals (e.g., invertase leader, α factor leader, or acid phosphatase leader) or mammalian secretion signals (e.g., herpes simplex gD signal).

Exemplary promoters active in mammalian cells include cytomegalovirus immediate early promoter (CMV-IE), human elongation factor 1-α promoter (EF1), small nuclear RNA promoters (U1a and U1b), α-myosin heavy chain promoter, Simian virus 40 promoter (SV40), Rous sarcoma virus promoter (RSV), Adenovirus major late promoter, β-actin promoter; hybrid regulatory element comprising a CMV enhancer/β-actin promoter or an immunoglobulin promoter or active fragment thereof. Examples of useful mammalian host cell lines are monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); or Chinese hamster ovary cells (CHO).

Typical promoters suitable for expression in yeast cells such as for example a yeast cell selected from the group comprising *Pichia pastoris, Saccharomyces cerevisiae* and *S. pombe*, include, but are not limited to, the ADH1 promoter, the GAL1 promoter, the GAL4 promoter, the CUP1 promoter, the PHOS promoter, the nmt promoter, the RPR1 promoter, or the TEF1 promoter.

Means for introducing the isolated nucleic acid or expression construct comprising same into a cell for expression are known to those skilled in the art. The technique used for a given cell depends on the known successful techniques. Means for introducing recombinant DNA into cells include microinjection, transfection mediated by DEAE-dextran, transfection mediated by liposomes such as by using lipofectamine (Gibco, MD, USA) and/or cellfectin (Gibco, MD, USA), PEG-mediated DNA uptake, electroporation and microparticle bombardment such as by using DNA-coated tungsten or gold particles (Agracetus Inc., WI, USA) amongst others.

The host cells used to produce the protein may be cultured in a variety of media, depending on the cell type used. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing mammalian cells. Media for culturing other cell types discussed herein are known in the art.

Isolation of Proteins

Methods for isolating a protein are known in the art and/or described herein.

Where an antigen binding site is secreted into culture medium, supernatants from such expression systems can be first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. Alternatively, or additionally, supernatants can be filtered and/or separated from cells expressing the protein, e.g., using continuous centrifugation.

The antigen binding site prepared from the cells can be purified using, for example, ion exchange, hydroxyapatite chromatography, hydrophobic interaction chromatography, gel electrophoresis, dialysis, affinity chromatography (e.g., protein A affinity chromatography or protein G chromatography), or any combination of the foregoing. These methods are known in the art and described, for example in WO99/57134 or Ed Harlow and David Lane (editors) Antibodies: A Laboratory Manual, Cold Spring Harbor Laboratory, (1988).

The skilled artisan will also be aware that a protein can be modified to include a tag to facilitate purification or detection, e.g., a poly-histidine tag, e.g., a hexa-histidine tag, or a influenza virus hemagglutinin (HA) tag, or a Simian Virus 5 (V5) tag, or a FLAG tag, or a glutathione S-transferase (GST) tag. The resulting protein is then purified using methods known in the art, such as, affinity purification. For example, a protein comprising a hexa-his tag is purified by contacting a sample comprising the protein with nickel-nitrilotriacetic acid (Ni-NTA) that specifically binds a hexa-his tag immobilized on a solid or semi-solid support, washing the sample to remove unbound protein, and subsequently eluting the bound protein. Alternatively, or in addition a ligand or antibody that binds to a tag is used in an affinity purification method.

Conjugates

In one example, an antigen binding site of the present invention is conjugated to a compound. For example, the compound is selected from the group consisting of a radioisotope, a detectable label, a therapeutic compound, a colloid, a toxin, a nucleic acid, a peptide, a protein, a compound that increases the half life of the antigen binding site in a subject and mixtures thereof.

The other compound can be directly or indirectly bound to the antigen binding site (e.g., can comprise a linker in the case of indirect binding). Examples of compounds include, a radioisotope (e.g., iodine-131, yttrium-90 or indium-111), a detectable label (e.g., a fluorophore or a fluorescent nanocrystal or quantum dot), a therapeutic compound (e.g., a chemotherapeutic or an anti-inflammatory), a colloid (e.g., gold), a toxin (e.g., ricin or tetanus toxoid), a nucleic acid, a peptide (e.g., a serum albumin binding peptide), a protein (e.g., a protein comprising an antigen binding domain of an antibody or serum albumin), a compound that increases the half life of the antigen binding site in a subject (e.g., polyethylene glycol or other water soluble polymer having this activity) and mixtures thereof. Exemplary compounds that can be conjugated to a antigen binding site of the invention and methods for such conjugation are known in the art and described, for example, in WO2010/059821.

The antigen binding site may be conjugated to nanoparticles (for example as reviewed in Kogan et al., *Nanomedicine (Lond)*. 2: 287-306, 2007). The nanoparticles may be metallic nanoparticles.

The antigen binding site may be comprised in antibody-targeted bacterial minicells (for example as described in PCT/IB2005/000204).

Some exemplary compounds that can be conjugated to a antigen binding site of the present invention are listed in Table 1.

TABLE 1

Compounds useful in conjugation.

| Group | Detail |
|---|---|
| Radioisotopes (either directly or indirectly) | $^{123}$I, $^{125}$I, $^{130}$I, $^{131}$I, $^{135}$I, $^{47}$Sc, $^{72}$As, $^{72}$Sc, $^{90}$Y, $^{88}$Y, $^{97}$Ru, $^{100}$Pd, $^{101m}$Rh, $^{101m}$Rh, $^{119}$Sb, $^{128}$Ba, $^{197}$Hg, $^{211}$At, $^{212}$Bi, $^{153}$Sm, $^{169}$Eu, $^{212}$Pb, $^{109}$Pd, $^{111}$In, $^{67}$Gu, $^{68}$Gu, $^{67}$Cu, $^{75}$Br, $^{76}$Br, $^{77}$Br, $^{99m}$Tc, $^{11}$C, $^{13}$N, $^{15}$O, $^{18}$I, $^{188}$Rc, $^{203}$Pb, $^{64}$Cu, $^{105}$Rh, $^{198}$Au, $^{199}$Ag or $^{177}$Lu |
| Half life extenders | Polyethylene glycol<br>Glycerol<br>Glucose |
| Fluorescent probes | Phycoerythrin (PE)<br>Allophycocyanin (APC)<br>Alexa Fluor 488<br>Cy5.5 |
| Biologics | fluorescent proteins such as Renilla luciferase, GFP<br>immune modulators or proteins, such as cytokines, e.g., an interferon<br>toxins<br>an immunoglobulin or antibody or antibody variable region<br>half life extenders such as albumin or antibody variable regions or peptides that bind to albumin |
| Chemotherapeutics | Taxol<br>5-FU<br>Doxorubicin<br>Idarubicin |

Assaying Activity of an IL-21-Binding Protein

Binding to IL-21 and Mutants Thereof

It will be apparent to the skilled artisan from the disclosure herein that some antigen binding sites of the present invention bind to the hIL-21 and to specific mutant forms of hIL-21. Methods for assessing binding to a protein are known in the art, e.g., as described in Scopes (In: Protein purification: principles and practice, Third Edition, Springer Verlag, 1994). Such a method generally involves immobilizing the antigen binding site and contacting it with labeled antigen. Following washing to remove non-specific bound protein, the amount of label and, as a consequence, bound antigen is detected. Of course, the antigen binding site can be labeled and the antigen immobilized. Panning-type assays can also be used. Alternatively, or additionally, surface plasmon resonance assays can be used.

Optionally, the dissociation constant (Kd), association constant (Ka) and/or affinity constant ($K_D$) of an immobilized antigen binding site for IL-21 or an epitope thereof is determined. The "Kd" or "Ka" or "$K_D$" for an 21-binding protein is in one example measured by a radiolabeled or fluorescently-labeled IL-21 binding assay. In the case of a "Kd", this assay equilibrates the antigen binding site with a minimal concentration of labeled IL-21 in the presence of a titration series of unlabeled IL-21. Following washing to remove unbound IL-21, the amount of label is determined, which is indicative of the Kd of the protein.

According to another example the Kd, Ka or $K_D$ is measured by using surface plasmon resonance assays, e.g., using BIAcore surface plasmon resonance (BIAcore, Inc., Piscataway, N.J.) with immobilized IL-21 or a region thereof or immobilized antigen binding site.

In some examples, the antigen binding site has a similar $K_D$ or an improved $K_D$ (i.e., a $K_D$ value lower than) than antibody 8E2, because they are likely to compete for binding to IL-21.

Determining Competitive Binding

Assays for determining a protein that competitively inhibits binding of antibody 2P2 will be apparent to the skilled artisan. One such method is exemplified herein.

For example, the antibody is conjugated to a detectable label, e.g., a fluorescent label or a radioactive label. The labeled antibody and the test antigen binding site are then mixed and contacted with IL-21 or a region thereof or a cell expressing same. The level of labeled antibody is then determined and compared to the level determined when the labeled antibody is contacted with the IL-21, region or cells in the absence of the antigen binding site. If the level of labeled antibody is reduced in the presence of the test antigen binding site compared to the absence of the antigen binding site, the antigen binding site is considered to competitively inhibit binding of the antibody to IL-21.

Optionally, the test antigen binding site is conjugated to different label to the antibody. This alternate labeling permits detection of the level of binding of the test antigen binding site to IL-21 or the region thereof or the cell.

Determining Agonist Activity

In some examples of the present invention, a protein is capable of enhancing IL-21 activity.

Various assays are known in the art for assessing the ability of a protein to enhance signaling of a ligand through a receptor.

In one example, the antigen binding site enhances proliferation of cells (e.g., BaF3 cells) expressing IL-21R and gp130 (e.g., cells modified to express the both proteins) which are cultured in the presence of IL-21. Cells (e.g., about $1\times10^4$ cell) are cultured in the presence of IL-21 (e.g., between about 0.5 ng/mL to about 5 ng/mL (such as 0.5 ng/mL or 5 ng/mL) for hIL-21 and the presence or absence of a test antigen binding site. Methods for assessing cell proliferation are known in the art and include, for example, MTT reduction and/or thymidine incorporation. An antigen binding site that enhances the level of proliferation compared to the level observed in the absence of the antigen binding site is considered to enhance or agonize IL-21 signaling.

A similar assay to that described in the foregoing paragraph can be performed with B9 cells or T10 cells (Dams-Kozlowska et al., *BMC Biotechnol*, 12: 8, 2012; and Yokote et al., *JAOAC*, 83: 1053-1057, 2000). In the case of an assay making use of T10 cells, proliferation can be measured by colorimetrically detecting reduction of the tetrazolium compound, 4-[3-(4-iodophenyl)-2-(4-nitrophenyl)-2H-5-tetrazolio]-1,3-benzene disulfonate (WST-1).

Other methods for assessing enhancement of IL-21 signaling are contemplated by the present disclosure.

Determining Half Life of IL-21

The half-life of IL-21 can be measured, for example, by pharmacokinetic studies, e.g., according to the method described by Kim et al, *Eur J of Immunol* 24:542, 1994. According to this method radiolabeled IL-21 is injected intravenously into mice and its plasma concentration is periodically measured as a function of time, for example at 3 minutes to 72 hours after the injection. The clearance curve thus obtained should be biphasic, that is, an alpha phase and beta phase. For the determination of the in vivo half-life of the protein, the clearance rate in beta-phase is calculated and compared with that of the wild type or unmodified protein.

Assessing Therapeutic Efficacy

Assays for assessing therapeutic efficacy are described hereinabove in relation to determining neutralization by an antigen binding site.

In another example, the efficacy of a protein to treat a condition is assessed using an in vivo assay.

For example, the antigen binding site can be tested in a model of cancer, e.g., gastric cancer. For example, mice homologous for the Y757F mutant of gp130 (gp130$^{Y757F/Y757F}$) develop gastric tumors Jenkins et al, *Blood* 109: 2380-2388, 2007). Mice (e.g., eight week old mice) are treated with an antigen binding site and the number and/or weight of gastric polyps assessed. An antigen binding site that reduces polyp size and/or weight is considered useful for treating cancer. A similar assay can be used to test for an effect on colon cancer, in which gp130$^{Y757F/Y757F}$ mice are treated with azoxymethane (AOM) followed by dextran sodium sulfate (DSS) essentially as described in Greten (et al, *Cell*, 118: 285-296, 2004) to induce colon cancer prior to treatment with the antigen binding site.

The antigen binding site can additionally or alternatively be tested in a model of cancer metastasis or cancer-related bone disease, e.g., as described in Li et al., *Oncol. Lett.* 3: 802-806, 2012.

Conditions to be Treated

IL-21 is a CD4$^+$ T cell-derived cytokine that is important for optimal CD8$^+$ T cell mediated immunity, NK activation and optimal humoral responses such as antibody production and B cell maturation. IL-21 has been shown to induce a number of proinflammatory cytokines such as IL18, IL-15, IL-5, IL-6, IL-7A, IL-17F, TNFRII, sCD25 and RANTES.

The antigen binding sites of the present invention are useful in the treatment of cancers. Exemplary cancers include cystic and solid tumors, bone and soft tissue tumors, including tumors in anal tissue, bile duct, bladder, blood cells, cone, bowel, brain, breast, carcinoid, cervix, eye, esophagus, head and neck, kidney, larynx, leukemia, liver, lung, lymph nodes, lymphoma, melanoma, mesothelioma, myeloma, ovary, pancreas, penis, prostate, skin, sarcomas, stomach, testes, thyroid, vagina, vulva. Soft tissue tumors include Benign schwannoma Monosomy, Desmoid tumor, lipo-blastoma, lipoma, uterine leiomyoma, clear cell sarcoma, dermatofibrosarcoma, Ewing sarcoma, extraskeletal myxoid chondrosarcoma, liposarcooma myxoid, Alveolar rhabdomyosarcoma and synovial sarcoma. Specific bone tumors include nonossifying fibroma, unicameral bone cyst, enchon-droma, aneurismal bone cyst, osteoblastoma, chondroblastoma, chondromyxofibroma, ossifying fibroma and adamantinoma, Giant cell tumor, fibrous dysplasia, Ewing's sarcoma eosinophilic granuloma, osteosarcoma, chondroma, chondrosarcoma, malignant fibrous histiocytoma and metastatic carcinoma. Leukemias include acute lymphoblastic, acute myeloblastic, chronic lymphocytic and chronic myeloid.

The antigen binding sites of the present invention are useful in the treatment and prevention of human viral infections. Examples of viral infections include infections caused by DNA viruses (e.g., Herpes Viruses such as Herpes Simplex viruses. Epstein-Barn virus. Cytomegalovirus; Pox viruses such as Variola (small pox) virus; Hepadnaviruses (e.g., Hepatitis B virus); Papilloma viruses; Adenoviruses); RNA Viruses (e.g., HIV I, II; HTLV I, II; Poliovirus; Hepatitis A; coronoviruses, such as sudden acute respiratory syndrome (SARS); Orthomyxoviruses (e.g., Influenza viruses); Paramyxoviruses (e.g., Measles virus); Rabies virus: Hepatitis C virus), Flaviviruses, Influenza viruses; caliciviruses; rabies viruses, rinderpest viruses, Arena virus, and the like. Moreover, examples of the types of virus-related diseases for which IL-21 could be used include, but are not limited to: Acquired immunodeficiency; Hepatitis; Gastroenteritis; Hemorrhagic diseases; Enteritis; Carditis; Encephalitis; Paralysis; Brochiolitis; Upper and lower respiratory disease; Respiratory Papillomatosis; Arthritis; Disseminated disease, Meningitis. Mononucleosis.

The antigen binding sites of the present invention are also useful in the treatment of microbial infections including chlamydiae, listeriae, *Helicobacter pylori, Mycobacterium, Mycoplasma, Bacillus anthracis, Salmonella*, and *Shigella*.

The antigen binding sites of the present invention are also useful as a monotherapy for acute and chronic viral infections and for immunocompromised patients. Methods that enhance immunity can accelerate the recovery time in patients with unresolved infections. Immunotherapies can have an even greater impact on subsets of immunocompromised patients such as the very young or elderly as well as patients that suffer immunodeficiencies acquired through infection, or induced following medical interventions such as chemotherapy or bone marrow ablation. Examples of the types of indications being treated via immune-modulation include; the use of IFN-α for chronic hepatitis, the use of IL-2 following HIV infection, and the use of either interferon for treating Epstein Barr Virus infections following transplantation.

The antigen binding sites of the present invention are also useful as an allergy immunotherapy for the treatment of for example, allergic rhinitis, hay fever and bronchial asthma.

Compositions

In some examples, an antigen binding site as described herein can be administered orally, parenterally, by inhalation spray, adsorption, absorption, topically, rectally, nasally, bucally, vaginally, intraventricularly, via an implanted reservoir in dosage formulations containing conventional non-toxic pharmaceutically-acceptable carriers, or by any other convenient dosage form. The term "parenteral" as used herein includes subcutaneous, intravenous, intramuscular, intraperitoneal, intrathecal, intraventricular, intrasternal, and intracranial injection or infusion techniques.

Methods for preparing an antigen binding site into a suitable form for administration to a subject (e.g. a pharmaceutical composition) are known in the art and include, for example, methods as described in Remington's Pharmaceutical Sciences (18th ed., Mack Publishing Co., Easton, Pa., 1990) and U.S. Pharmacopeia: National Formulary (Mack Publishing Company, Easton, Pa., 1984).

The pharmaceutical compositions of this invention are particularly useful for parenteral administration, such as intravenous administration or administration into a body cavity or lumen of an organ or joint. The compositions for administration will commonly comprise a solution of an antigen binding site dissolved in a pharmaceutically acceptable carrier, for example an aqueous carrier. A variety of aqueous carriers can be used, e.g., buffered saline and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of an antigen binding site of the present invention in these formulations can vary widely, and will be selected primarily based on fluid volumes, viscosities, body weight and the like in accordance with the particular mode of administration selected and the patient's needs. Exemplary carriers include water, saline, Ringer's solution, dextrose solution, and 5% human serum albumin. Nonaqueous vehicles such as mixed oils and ethyl oleate may also be used. Liposomes may also be used as carriers. The vehicles may contain minor amounts of additives that enhance isotonicity and chemical stability, e.g., buffers and preservatives.

Upon formulation, an antigen binding site of the present invention will be administered in a manner compatible with the dosage formulation and in such amount as is therapeutically/prophylactically effective. Formulations are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, liposomal forms and the like. Pharmaceutical "slow release" capsules or compositions may also be used. Slow release formulations are generally designed to give a constant drug level over an extended period and may be used to deliver an antigen binding site of the present invention.

WO2002/080967 describes compositions and methods for administering aerosolized compositions comprising antibodies for the treatment of, e.g., asthma, which are also suitable for administration of an antigen binding site of the present invention.

Combination Therapies

In one example, an antigen binding site of the present invention is administered in combination with one or more other compound useful for treating a condition described herein, either as combined or additional treatment steps or as additional components of a therapeutic formulation.

In another example, the other compound is a chemotherapy drug or other drug used for treating cancer.

In another example, the protein described herein is administered before or after radiotherapy for the treatment of cancer.

In another example, the antigen binding site of the present invention is administered in combination with an immunotherapy.

Suitable immunotherapies include but are not limited to: checkpoint inhibitors; tyrosine kinase inhibitors, cytokines or interleukins; interferons; granulocyte macrophage colony stimulating factor; vaccines (cancer vaccine or infectious disease); antiviral drugs; oncolytic viruses; polysaccharides such as beta glucan (Lentinan); and adoptive cell therapies (ACT) such as ex vivo cultured T cells to a cytotoxic T lymphocyte fate in a T helper cell independent manner or T cells genetically modified to express chimeric antigen receptors (CARs).

Suitable immunotherapies may be targeted to, but not limited to targeting the following: Programmed death 1 (PD1), Programmed death ligand 1 (PDL1) or Programmed death ligand 2 (PDL2), Cluster of Differentiation 80 (CD80), Cluster of Differentiation 80 (CD86), B7-related protein 1 (B7RP1), Cluster of Differentiation 276 (CD276), Cluster of Differentiation 274 (CD274), Herpesvirus entry mediator (HVEM), Cluster of Differentiation Ligand (CD137L), Tumor Necrosis Factor Receptor Superfamily Member 4 Ligand (OX40L), Cluster of Differentiation (CD70), Cluster of Differentiation (CD40), Galectin 9 (GAL9), Cluster of Differentiation 28 (CD28), Cyotoxic T-lymphocyte activator-4 (CTLA4), Inducible T-cell costimulator (ICOS), B and T lymphocyte attenuator (BTLA), Killer cell immunoglobulin-like receptor (KIR), TCR, Lymphocyte-activation gene 3 (LAG3), Cluster of Differentiation 137 (CD137), Tumor Necrosis Factor Receptor Superfamily Member 42 (OX40), Cluster of Differentiation 27 (CD27), Cluster of Differentiation 40 Ligand (CD40L), adenosine A2a receptor (AZaR) and TIM3 (T-cell immunoglobulin-3).

Suitable checkpoint inhibitors include: the PD-1 inhibitors Nivolumab (Bristol-Myers Squibb/Ono Pharmaceutical), Lambrolizumab (MK-3475; Merck), Pidilizunab (CureTech/Teva) and AMP-224 (Amplimmune/ GlaxoSmithKline); the PD-L1 inhibitors RG-7446 (Roche) and MEDI-4736 (AstraZeneca); and the CTLA-4 inhibitor Ipilimumab. Suitable tyrosine kinase inhibitors include Sorafinib, Imatinib, Gefinitib, Palladia, Erlotinib, Lapatinib, Sunitinib, Nilotinib, Suitable cytokines or interleukins include IL-2, IL-7, IL-12. Suitable interferons include IFN-alpha, IFN-beta and IFN-gamma. A suitable Granulocyte Macrophage Colony Stimulating Factor includes Sargramostin. Suitable vaccines include Sipuleucel-T and suitable oncolytic viruses include Talimogene laherparepvec.

In another example, the antigen binding site of the present invention is administered in combination with an immunomodulating drug.

Suitable immunomodulating drugs include Thalidomice (Thalomid), lenalidomide (Revlimid) and pomalidomide (Pomalyst).

Dosages and Timing of Administration

Suitable dosages of an antigen binding site of the present invention will vary depending on the specific an antigen binding site, the condition to be treated and/or the subject being treated. It is within the ability of a skilled physician to determine a suitable dosage, e.g., by commencing with a sub-optimal dosage and incrementally modifying the dosage to determine an optimal or useful dosage. Alternatively, to determine an appropriate dosage for treatment/prophylaxis, data from the cell culture assays or animal studies are used, wherein a suitable dose is within a range of circulating concentrations that include the $ED_{50}$ of the active compound with little or no toxicity. The dosage may vary within this range depending upon the dosage form employed and the route of administration utilized. A therapeutically/prophylactically effective dose can be estimated initially from cell culture assays. A dose may be formulated in animal models to achieve a circulating plasma concentration range that includes the $IC_{50}$ (i.e., the concentration or amount of the compound which achieves a half-maximal inhibition of symptoms) as determined in cell culture. Such information can be used to more accurately determine useful doses in humans. Levels in plasma maybe measured, for example, by high performance liquid chromatography.

In some examples, a method of the present invention comprises administering a prophylactically or therapeutically effective amount of a protein described herein.

The term "therapeutically effective amount" is the quantity which, when administered to a subject in need of treatment, improves the prognosis and/or state of the subject and/or that reduces or inhibits one or more symptoms of a clinical condition described herein to a level that is below that observed and accepted as clinically diagnostic or clinically characteristic of that condition. The amount to be administered to a subject will depend on the particular characteristics of the condition to be treated, the type and stage of condition being treated, the mode of administration, and the characteristics of the subject, such as general health, other diseases, age, sex, genotype, and body weight. A person skilled in the art will be able to determine appropriate dosages depending on these and other factors. Accordingly, this term is not to be construed to limit the present invention to a specific quantity, e.g., weight or amount of protein(s), rather the present invention encompasses any amount of the antigen binding site(s) sufficient to achieve the stated result in a subject.

As used herein, the term "prophylactically effective amount" shall be taken to mean a sufficient quantity of a protein to prevent or inhibit or delay the onset of one or more detectable symptoms of a clinical condition. The skilled artisan will be aware that such an amount will vary depending on, for example, the specific antigen binding site(s) administered and/or the particular subject and/or the type or severity or level of condition and/or predisposition (genetic or otherwise) to the condition. Accordingly, this term is not to be construed to limit the present invention to a specific quantity, e.g., weight or amount of antigen binding site(s), rather the present invention encompasses any amount of the antigen binding site(s) sufficient to achieve the stated result in a subject.

For in vivo administration of the antigen binding site described herein, normal dosage amounts may vary from about 10 ng/kg up to about 100 mg/kg of an individual's body weight or more per day. For repeated administrations over several days or longer, depending on the severity of the disease or disorder to be treated, the treatment can be sustained until a desired suppression of symptoms is achieved.

In some examples, the antigen binding site is administered at an initial (or loading) dose of between about 1 mg/kg to about 30 mg/kg, such as from about 1 mg/kg to about 10 mg/kg, or about 1 mg/kg or about 2 mg/kg or 5 mg/kg. The antigen binding site can then be administered at a lower maintenance dose of between about 0.01 mg/kg to about 2 mg/kg, such as from about 0.05 mg/kg to about 1 mg/kg, for example, from about 0.1 mg/kg to about 1 mg/kg, such as about 0.1 mg/kg or 0.5 mg/kg or 1 mg/kg. The maintenance doses may be administered every 7-30 days, such as, every 10-15 days, for example, every 10 or 11 or 12 or 13 or 14 or 15 days.

In some examples, the antigen binding site is administered at a dose of between about 0.01 mg/kg to about 50 mg/kg, such as between about 0.05 mg/kg to about 30 mg/kg, for example, between about 0.1 mg/kg to about 20 mg/kg, for example, between about 0.1 mg/kg to about 10 mg/kg, such as between about 0.1 mg/kg to about 2 mg/kg. For example, the antigen binding site is administered at a dose of between about 0.01 mg/kg to about 5 mg/kg, such as from about 0.1 mg/kg to about 2 mg/kg, such as about 0.2 mg/kg or 0.3 mg/kg or 0.5 mg/kg or 1 mg/kg or 1.5 mg/kg (e.g., without a higher loading dose or a lower maintenance dose). In some examples, numerous doses are administered, e.g., every 7-30 days, such as, every 10-22 days, for example, every 10-15 days, for example, every 10 or 11 or 12 or 13 or 14 or 15 or 16 or 17 or 18 or 19 or 20 or 21 or 22 days. For example, the antigen binding site is administered every 7 days or every 14 days or every 21 days.

In some examples, at the time of commencing therapy, the mammal is administered the antigen binding site on no more than 7 consecutive days or 6 consecutive days or 5 consecutive days or 4 consecutive days.

In the case of a mammal that is not adequately responding to treatment, multiple doses in a week may be administered. Alternatively, or in addition, increasing doses may be administered.

In another example, for mammals experiencing an adverse reaction, the initial (or loading) dose may be split over numerous days in one week or over numerous consecutive days.

Administration of an antigen binding site according to the methods of the present invention can be continuous or intermittent, depending, for example, on the recipient's physiological condition, whether the purpose of the administration is therapeutic or prophylactic, and other factors known to skilled practitioners. The administration of an antigen binding site may be essentially continuous over a preselected period of time or may be in a series of spaced doses, e.g., either during or after development of a condition.

Kits

The present invention additionally comprises a kit comprising one or more of the following:

(i) an antigen binding site of the invention or expression construct(s) encoding same;

(ii) a cell of the invention;

(iii) a complex of the invention; or (iii) a pharmaceutical composition of the invention.

In the case of a kit for detecting IL-21, the kit can additionally comprise a detection means, e.g., linked to a antigen binding site of the invention.

In the case of a kit for therapeutic/prophylactic use, the kit can additionally comprise a pharmaceutically acceptable carrier.

Optionally a kit of the invention is packaged with instructions for use in a method described herein according to any example.

The present invention includes the following non-limiting Examples.

It will be understood that the invention disclosed and defined in this specification extends to all alternative combinations of two or more of the individual features mentioned or evident from the text or drawings. All of these different combinations constitute various alternative aspects of the invention.

EXAMPLES

Methods

Human B-Cell Proliferation Assay

Peripheral blood mononuclear cells (PBMC) were isolated from healthy human donors according to standard techniques and the PBMCs were stained with CFSE and then sorted into CD19+ CD27− IgD+ naïve B cells and CD19+ CD27+ IgD− memory B cells. Sorted cells were seeded into culture plate. Cells were then stimulated with 0.5-50 ng/ml of human IL-21 with or without 2P2. After 5 days cellular proliferation was determined via CFSE dilution or 3H thymidine proliferation assay.

In Vivo Half-Life ELISA Assay

To detect in vivo half-life of hIL-21/2P2 complex, mice were injected I.V. or S.C. with hIL-21/2P2 or hIL-21 alone, where 2P2 in the complex has been biotinylated using a commercial biotinylation kit. After 1 hr, 3 hr, 8 hr and 24 hrs post injection, mice were bled and levels of hIL-21 in serum were measure by ELISA. ELISA was done by coating plate with unconjugated 3A3, followed by blocking and incubation with serum. Plate was subsequently incubated with biotinylated 2P2 and detected with Streptavidin-HRP and TMB substrates.

ELISA Assay

To detect epitopes of 2P2 and 3A3, peptides consisting of different regions of hIL-21 were synthesized commercially and coated on an ELISA plate, followed by blocking of non-specific binding sites with 3% BSA in PBS. Biotinylated 2P2 or 3A3 were then added to the wells and developed with Streptavidin-HRP and TMB substrates.

Epitopes identified from previous experiments were then tested for the ability to block the binding of 2P2 or 3A3 to full length hIL-21. Full length hIL-21 was coated on EIA plate followed by blocking of non-specific binding sites with BSA. Biotinylated 2P2 or 3A3 were then spiked with the corresponding peptides and incubated on plate followed by detection with TMB substrates.

Example 1 Screening of the Anti-IL-21 Antibodies

A library of monoclonal antibodies to human IL-21 (hIL-21) was generated by the inventors. The clones were screened for their ability to enhance proliferation of cells of primary human B cells (BaF3 cells) expressing the human IL-21 receptor (BaF3-hIL-21R cells; Parrish-Novak J et al. (2000) Nature 408:57-63). Each monoclonal antibody was serially diluted 10-fold as shown in FIG. 1 and mixed with 2 ng/ml of hIL-21 and incubated with the BaF3-hIL-21R cells cultured in RPMI-1640 media respectively in a humidified chamber with 5% $CO_2$ at 37 C. For [$^3$H]-labelled thymidine incorporation assay to measure the cell proliferation, BaF3-huIL-21R cells were starved in the cultured media without cytokine for 18 h and then were incubated for 72 h with the addition of 1 µCi/well [$^3$H]-thymidine (Perkin Elmer, Waltham, Mass., USA) for the last 18 h of culture in the presence of cytokine. Cells were harvested onto filter mats (Perkin Elmer) and incorporated radioactive nucleic acids counted using a Top Count NXT Scintillation Counter (Packard Biosciences, Meriden, Conn., USA). Results were expressed as mean count per minute (CPM) for triplicate cultures. As demonstrated in FIG. 1, monoclonal antibody 2P2 increased the proliferation of BaF3-hIL-21R cells in a dose dependent manner. Accordingly, antibody 2P2 demonstrated an enhancing capability on cellular proliferation in the presence of the IL-21 cytokine suggesting that the antibody may function as an agonist of human IL-21. The Heavy and light CDRs of the VH and VL and are shown in FIG. 2. The CDR sequences as determined by IMGT numbering scheme are underlined.

Example 2 mAB 2P2 Potentiates hIL-21 Through the IL-21 Receptor

The inventors next determined whether the enhancing capability of the 2P2 monoclonal antibody was specific to the human IL-21 receptor. Primary human BaF3 cells, BaF3 cells expressing a murine IL-21 receptor (BaF3-mIL-21R) and BaF3 cells expressing a human IL-21 receptor (BaF3-hIL-21R) were plated in the presence of 0.1, 1.0 and 10.0 µg/ml of 2P2 antibody (FIG. 3A) and 2 ng/ml human IL-21. Coding sequences for human IL-21R (huIL-21R) and mouse IL-21R (msIL-21R) were cloned by PCR from human or mouse cDNA libraries respectively, sequenced to match NM_021798 and NM_021887. For [$^3$H]-labelled thymidine incorporation assay to measure the cell proliferation, Ba/F3-huIL-21R or Ba/F3-mIL-21R cells were starved in the cultured media without cytokine for 18 h and then were incubated for 72 h with the addition of 1 µCi/well [$^3$H]-thymidine (Perkin Elmer, Waltham, Mass., USA) for the last 18 h of culture in the presence of cytokines with indicated concentrations. Cells were harvested onto filter mats (Perkin Elmer) and incorporated radioactive nucleic acids counted using a Top Count NXT Scintillation Counter (Packard Biosciences, Meriden, Conn., USA). Results were expressed as mean count per minute (CPM) for triplicate cultures.

Figure 3:
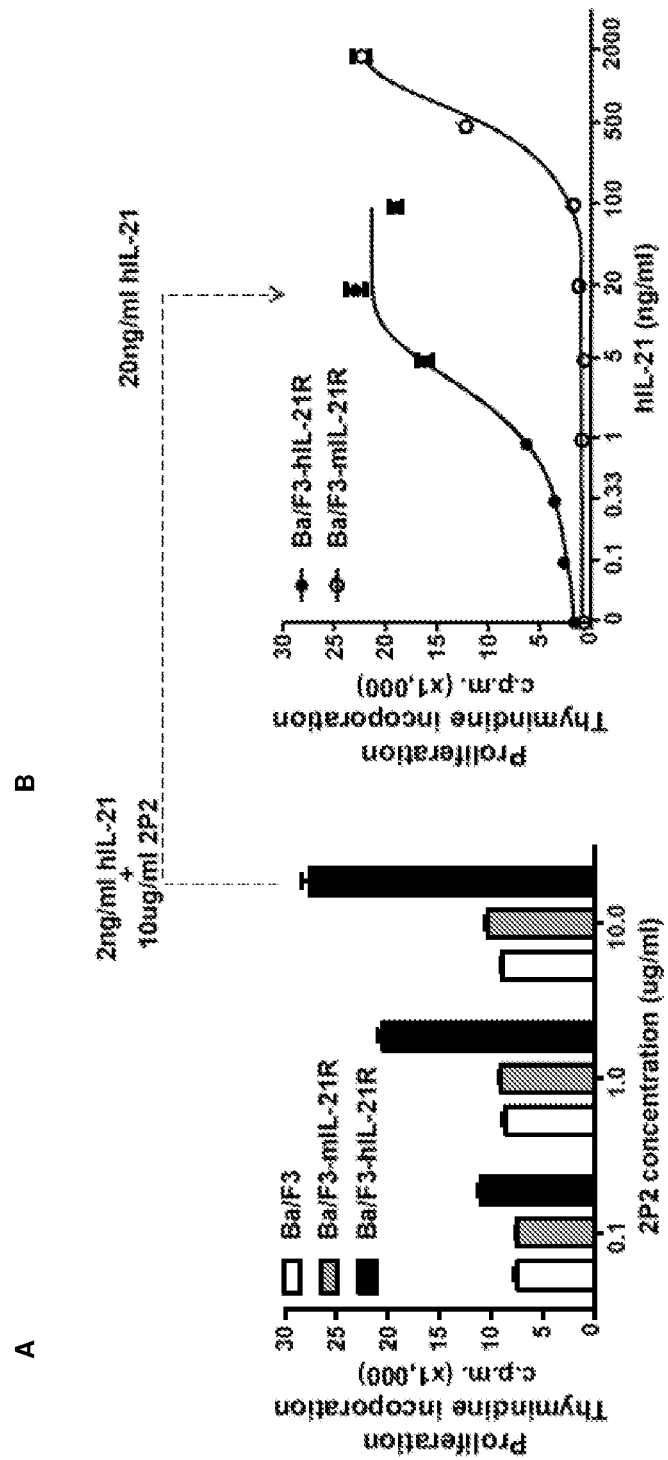
FIG. 3 shows that mAb 2P2 increased the proliferation of Ba/F3-hIL-21R cells but not Ba/F3-mIL-21R cells (A) and that mAb 2P2 increased hIL-21 bioactivity by more than 10 fold (B) (n=3±SEM).

The results demonstrated that 2P2 specifically increased proliferation of Ba/F3-hIL-21R cells but not Ba/F3-mIL-21R or Ba/F3 cells indicating that the activity of the 2P2 antibody was specific to human IL-21 since it did not enhance the function of murine IL-21. FIG. 3B shows the effect on cellular proliferation of Ba/F3-hIL-21R cells (closed circles) and BaF3-mIL-21R cells (open circles) by 2P2 plotted against human IL-12 (ng/ml). At a concentration of 10 µg/ml 2P2, the bioactivity of human IL-21 was increased greater than 10-fold. However, there was no effect on the bioactivity of human IL-21 in the presence of cells expressing the murine IL-21 receptor.

Example 3 2P2 Potentiates hIL-21 Mediated Human B Cell Proliferation

Figure 4:
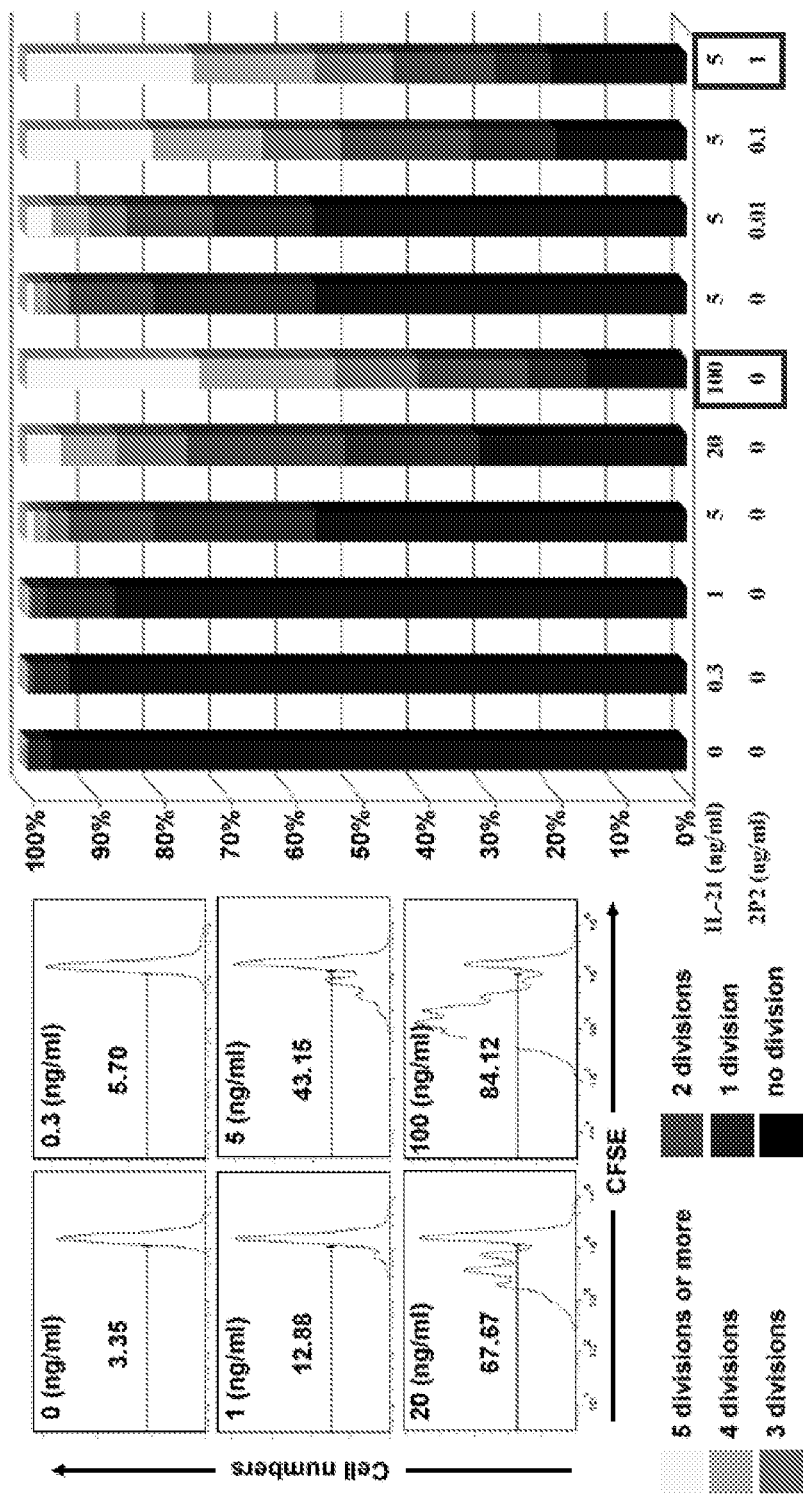
FIG. 4 shows that mAb 2P2 increased hIL-21-mediated proliferation of human B cells; and that 5 ng/ml of hIL-21 plus 1 ug/ml of mAb 2P2 demonstrated a similar bioactivity to 100 ng/ml of hIL-21, indicating about a 20-fold increase of hIL-21 biotactity by mAb 2P2.

Human B cells were enriched from peripheral blood mononuclear cells of healthy donors using the markers CD19, CD27, CD4 and CD45. B cell proliferation was measured using flow cytometry according to standard methods. Cells were labelled with carboxyfluorescein succinimidyl ester (CFSE) and incubated in the presence of 0, 0.3, 1, 5, 20 and 100 ng/ml of human IL-21. The percentage of cells that had undergone at least one division was determined by flow cytometry. As shown in FIG. 4A for example, at 20 ng/ml human IL-21, about 67% of the human B cells proliferated. In FIG. 4B, the flow cytometry data is reproduced as the first six bars. The remaining four bars show percentage of proliferated B cells in the presence of 5 ng/ml of IL-21 and 0, 0.01, 01 and 1 µg/ml of 2P2 antibody. 5 ng/ml of hIL-21 plus 1 µg/ml of mAb 2P2 demonstrated a similar bioactivity to 100 ng/ml of hIL-21 in the absence of 2P2 antibody thus demonstrating that mAb 2P2 increased the bioactivity of hIL-21 by approximately 20-fold suggesting it was a potent agonist of IL-21 activity.

Example 4 2P2 Potentiates hIL-21 Mediated Human CD8 T Cell Activation

Figure 5:
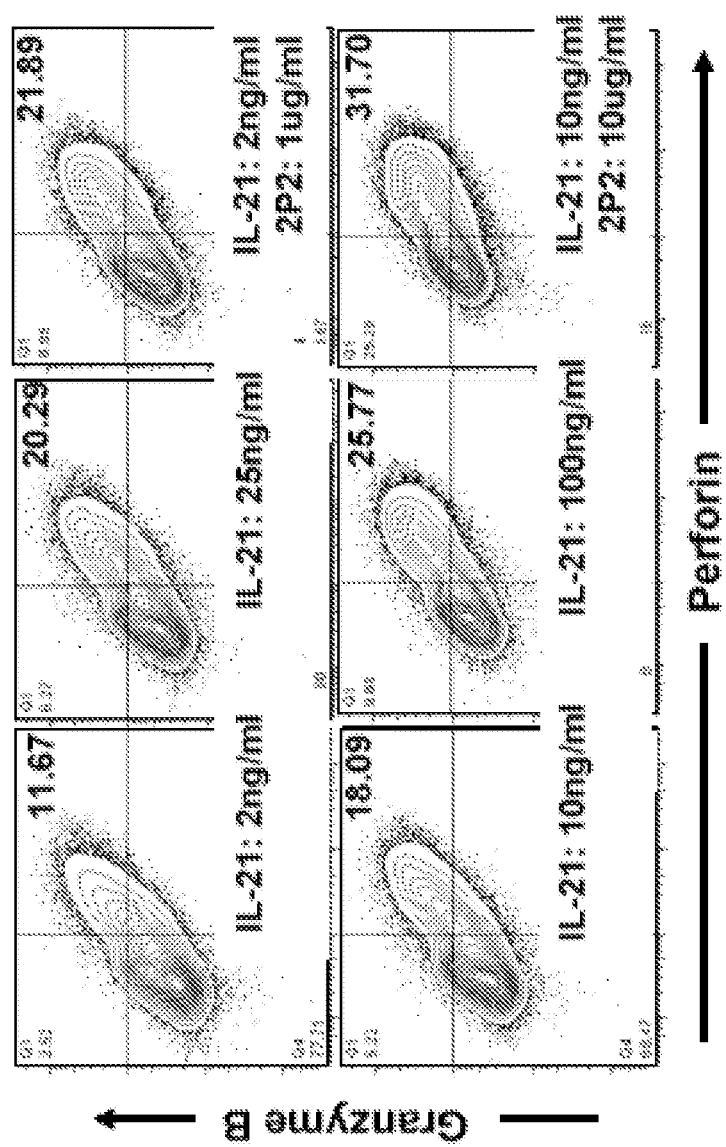
FIG. 5 shows that mAb 2P2 increased hIL-21-mediated activation of human CD8 T cells to express cytotoxic molecules including Granzyme B and Perforin, which are important for anti-virus and anti-tumour immunity.

Human CD8 T cells were incubated in the presence of IL-21 at the various concentrations shown in FIG. 5. In the first three panels, cells were incubated in the presence of IL-21 alone (2 ng/ml and 25 ng/ml) and IL-21 plus 2P2 (2 ng/ml and 1 µg/ml respectively). In the second panel the cells were incubated in the presence of IL-21 alone (10 ng/ml and 100 ng/ml) and IL-21 plus 2P2 (10 ng/ml and 10 µg/ml respectively). The cells were stained for granzyme B and perforin which were indicative of activation of the CD8 T cells since expression of these cytotoxic molecules is important for anti-virus and anti-tumour immunity. The percentage of granzyme B/perforin double positive cells is shown in the upper right hand quadrant. FIG. 5 shows that the 2 ng/ml of hIL-21 plus 1 µg/ml of mAb 2P2 demonstrated a better bioactivity on T cells than that of 25 ng/ml of hIL-21 alone (21.89% positive versus 20.29% positive) and 10 ng/ml of hIL-21 plus 10 µg/ml of mAb 2P2 demonstrated a better bioactivity than that of 10 ng/ml of hIL-21 alone (31.70% versus 25.77% positive), indicating over a 10-fold increase of hIL-21 bioactivity by mAb 2P2.

Example 5 Monoclonal Antibody 2P2 Prolongs hIL-21 Half-Life In Vivo

Figure 6:
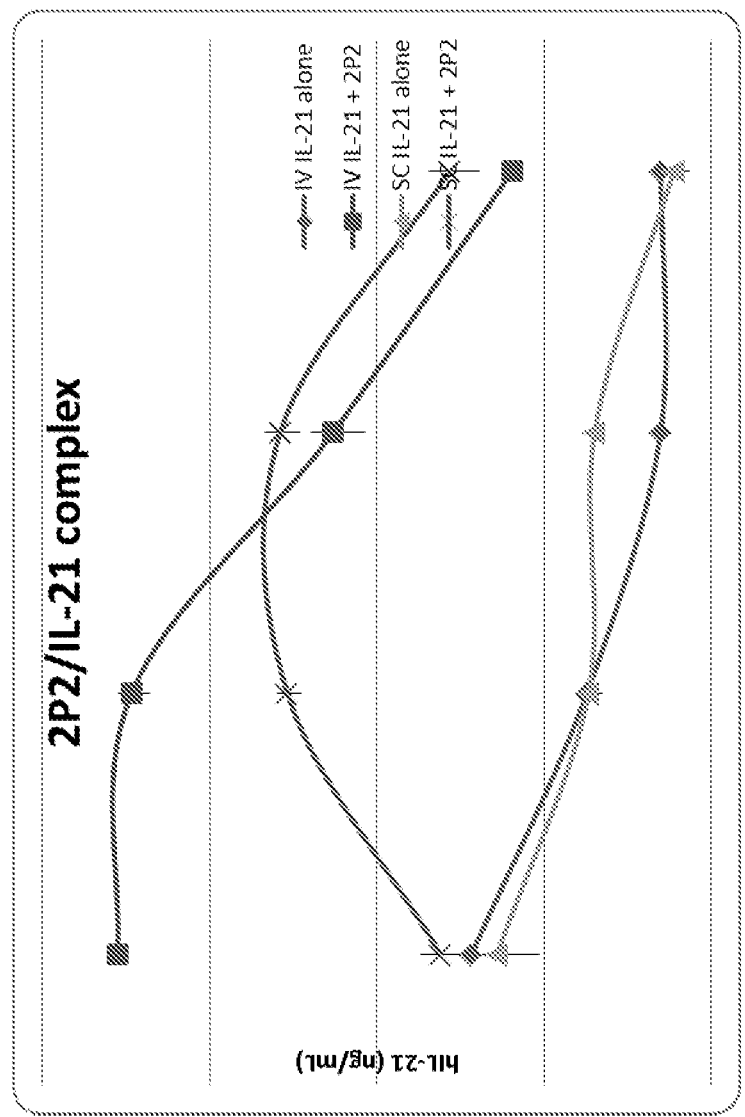
FIG. 6 shows the results of half-life determination of IL-21/2P2 complexes or IL-21 alone, administered either intravenously (IV) or Subcutaneously (SC) (n=3±SEM).

Serum half-life of hIL-21/2P2 and hIL-21/3A3 complexes was determined in vivo according to an ELISA assay. Wild-type mice were injected intravenously with either 25 µg hIL-21; 25 µg hIL-21 and 125 µg 2P2-biotin; or 25 µg hIL-21 and 125 µg 3A3-biotin. Mice were bled from the cheek at 1, 3, 8 and 24 hrs and 100 µl of blood obtained. The blood was then incubated for 30 mins at room temperature to obtain serum. Measurement of the level of hIL-21 in the serum was determined by ELISA. The detection limit of the assay is 1 ng/ml. FIG. 6 shows detection of hIL-21/2P2 complexes administered either intravenously (IV) or subcutaneously (SC) from serum over 24 hrs. 2P2 administered via either route resulted in a significant increase in serum retention of hIL-21 at all time points tested when compared to hIL-12 administered alone. 2P2 enhanced serum AUC of hIL-21 54 fold when administered subcutaneously (SC IL-21 alone AUC 117; SC IL-21/2P2 AUC 6340) and 164 (IV IL-21 alone AUC 91.36; IV IL-21/2P2 AUC 14993) when administered intravenously.

Example 6 Antibody 2P2 Enhances IL-21 Activity In Vivo

The inventors then determined whether 2P2 enhances IL-21 activity in vivo. A mouse strain was generated by replacing the endogenous mIL-21 receptor with the hIL-21 receptor. These mice have no endogenous IL-21 cytokine and are referred to as homozygous hIL-21R$^{KI/KI}$ and hIL21$^{KI/KI}$. The mice have a normal immune system and physiological expression of hIL-21R so they can be used to test the function of hIL-21 and 2P2 in vivo. Mice were injected intravenously with hIL-21 or hIL-21 and 2P2 at D0, D2 and D4. The treatment schedule is set out in Table 2 below.

TABLE 2

Treatment regimen

| Group (n = 3) | Treatment |
|---|---|
| 1 | 5 µg IL-21 |
| 2 | 25 µg IL-21 |
| 3 | 5 µg IL-21 + 125 µg 2P2 |
| 4 | 5 µg IL-21 + 125 µg 3A3 |

Antibody 3A3 (commercially available) which binds to human IL-21 but does not enhance the activity of IL-21 was used as a control. At D5 mice were sacrificed and their spleen and lymph nodes harvested. Administration of hIL-21/2P2 complex was found to enlarge the spleens to a greater extent compared to recombinant hIL-21 alone in hIL-21R knock-in mice, suggesting a better immunostimulatory function of 2P2 in vivo.

Single cell suspensions were prepared according to standard protocols. For B cell detection, the cell suspension was stained with antibodies and analyzed by FACS (flow cytometry LSR2 from BD). Populations of B cells were analyzed as followed:

follicular zone (FZ) B cells—CD3$^-$B220$^+$ IgD$^+$;
marginal zone (MZ) B cells—CD3$^-$B220+ IgM+CD23$^-$;
transitional B cells—CD3$^-$B220$^+$ IgM$^+$ AA4.1$^+$.

Figure 7:
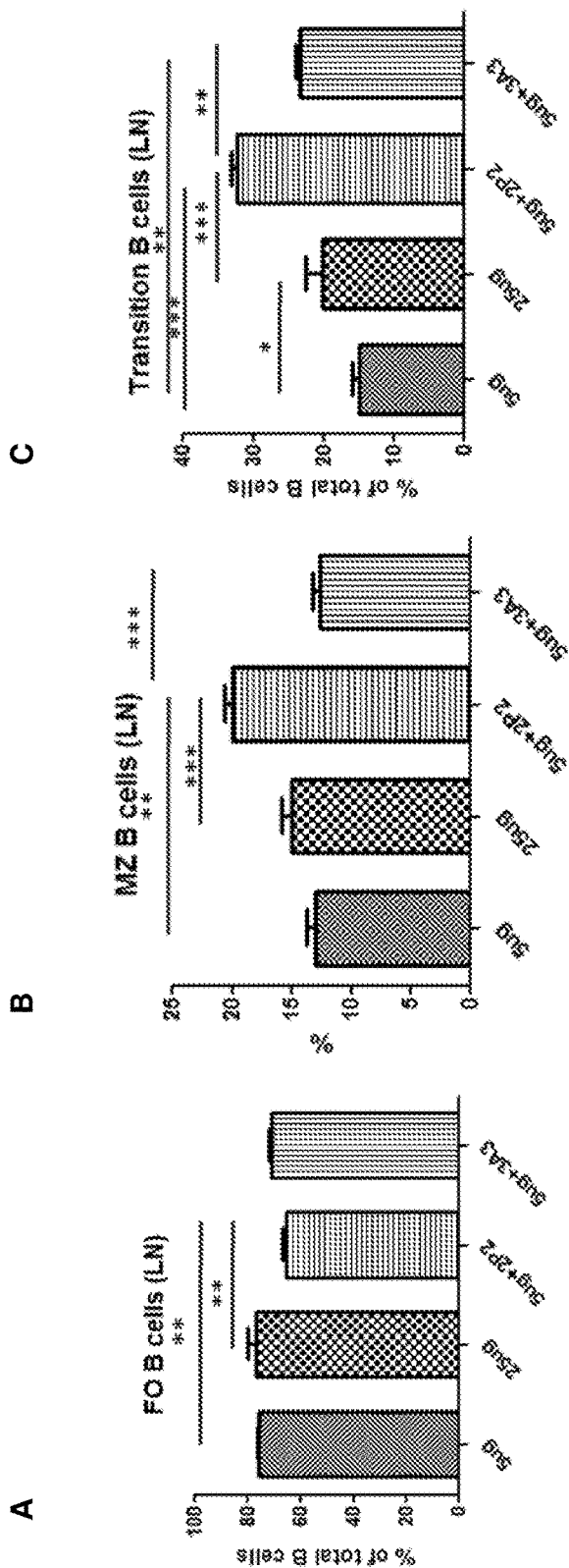
FIG. 7 shows the results of 2P2 enhancement of IL-21 mediated B cell proliferation in the lymph node for follicular B cells (A), marginal zone B cells (B) and transition B cells (C) (n=3±SEM; *P>0.05,  P>0.01 *P>0.001).
Figure 8:
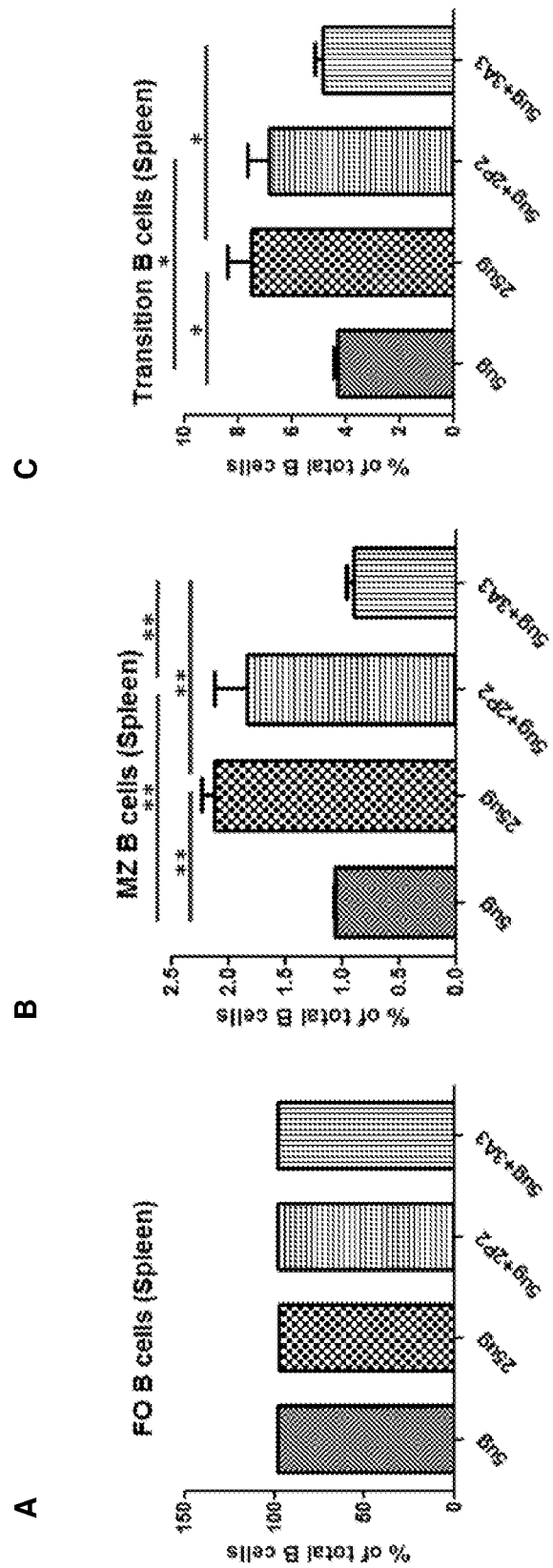
FIG. 8 shows the results of 2P2 enhancement of IL-21 mediated B cell proliferation in the spleen for follicular B cells (A), marginal zone B cells (B) and transition B cells (C) (n=3±SEM; *P>0.05,  P>0.01 *P>0.001).

The results are shown in FIG. 7 for FZ, MZ and transitional B cells from the lymph node and FIG. 8 for FZ, MZ and transitional B cells from the spleen. Statistical analysis was performed using a One-Way ANOVA (Newman-Keuls test) for analysis of differences between multiple groups. (Graphpad Prism Statistical software (Graphpad Software Inc, La Jolla, Calif. USA). The results showed that addition of 2P2 significantly increased transitional B cells in lymph node and spleen and significantly increase marginal zone B cells of the lymph node Table 4 and Table 5.

TABLE 4

One-Way ANOVA Summary

| One-way ANOVA | FO B cells (LN) | MZ B cells (LN) | Transition B cells (LN) | FO B cells (spleen) | MZ B cells (spleen) | Transition B cells (spleen) |
|---|---|---|---|---|---|---|
| P value | 0.0076 | 0.0003 | 0.0001 | 0.32.0 | 0.0016 | 0.0184 |
| P value summary | ** | *** | *** | ns | ** | * |

TABLE 5

Newman-Keuls Multiple Comparison test

| Newman-Keuls Multiple Comparison test | FO B cells (LN) | MZ B cells (LN) | Transition B cells (LN) | FO B cells (spleen) | MZ B cells (spleen) | Transition B cells (spleen) |
|---|---|---|---|---|---|---|
| 5 µg v 25 µg | ns | ns | * | — | ** | * |
| 5 µg v 5 µg + 2P2 | ** | *** | *** | — | ** | * |
| 5 µg v 5 µg + 3A3 | ns | ns | ** | — | ns | ns |
| 25 µg v 5 µg + 2P2 | ** | ** | *** | — | ns | ns |
| 25 µg v 5 µg + 3A3 | ns | ns | Ns | — | ** | * |
| 5 µg + 2P2 v 5 µg + 3A3 | ns | * |  | — | ** | Ns | ns = not significant,
*P < 0.05,
**P < 0.01 and
***P < 0.001

Example 7 Epitope Refinement

The inventors then sought to determine which residues of human IL-21 were bound by the 2P2 antibody. FIG. 9 shows the sequence of human IL-21 which residues in bold predicted to be residues bound by antibody 2P2 according to structural simulation studies, underlined residues are located within IL-21 helix regions. The inventors generated 5 peptides of hIL-21 as follows and as shown in FIG. 9:

```
Peptide 1 (P1, 30 aa; SEQ ID NO: 19):
FLPAPEDVETNCEWSAFSCFQKAQLKSANT

Peptide 2 (P2, 27 aa; SEQ ID NO: 20):
AQLKSANTGNNERIINVSIKKLKRKPP

Peptide 3 (P3, 30 aa; SEQ ID NO: 4):
IKKLKRKPPSTNAGRRQKHRLTCPSCDSYE

Peptide 4 (P4, 23 aa; SEQ ID NO: 21):
PPSTNAGRRQKHRLTCPSCDSYE

Peptide 5 (P5, 15 aa; SEQ ID NO: 22):
PPSTNAGRRQKHRLT
```

Figure 10:
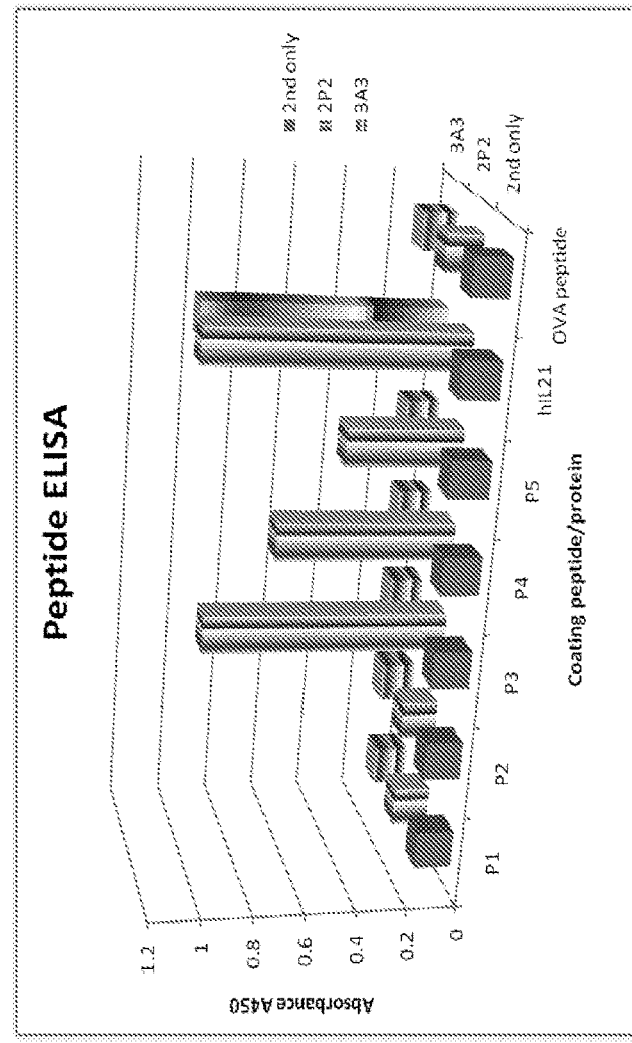
FIG. 10 shows binding between peptide fragments of human IL-21 and 2P2 and control antibody 3A3 determined by ELISA.
Figure 11:
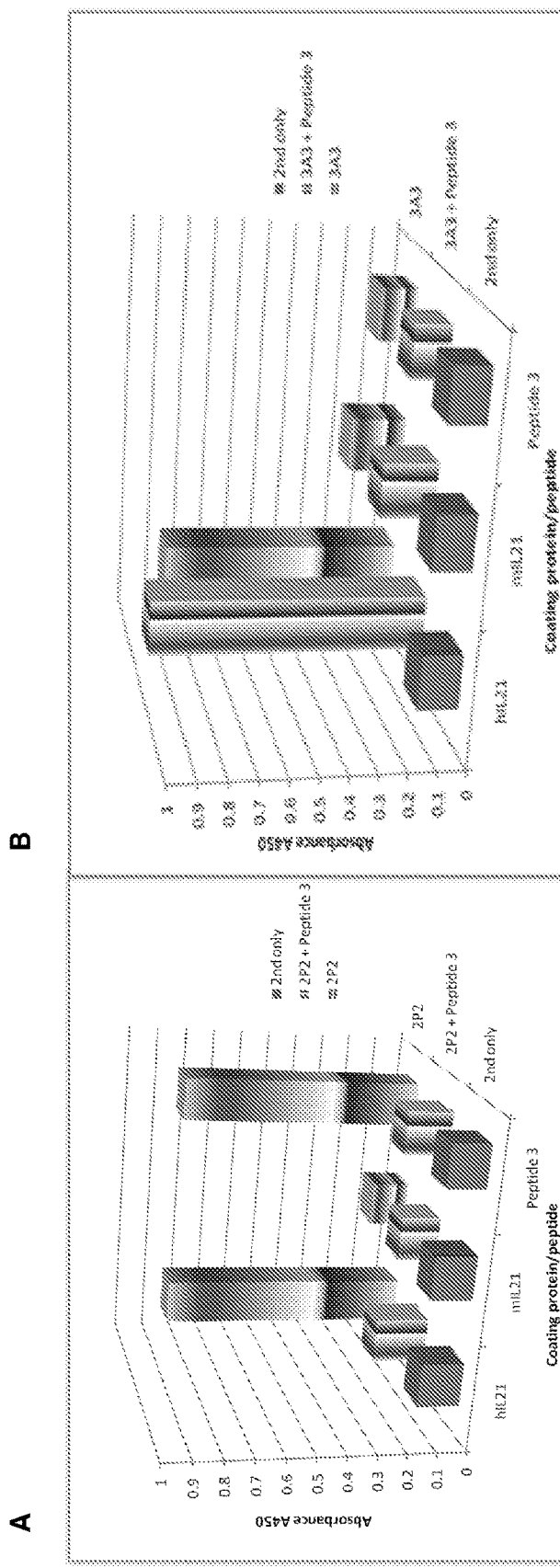
FIG. 11 shows (A) binding between human IL-21 or mouse IL-21 with 2P2 (B) shows binding between human IL-21 and mouse IL-21 with control antibody 3A3.

An ELISA assay was used to examine binding between antibodies 2P2 and 3A3 and a Streptavidin-HRP secondary only control to each of the peptides P1 to P5, hIL-21 and OVA peptide. As shown in FIG. 10, antibody 2P2 bound peptide 3 the strongest, followed by peptide 4 and peptide 5. Thus, the epitope recognized by antibody 2P2 comprised a minimal sequence of 9 mer to 15 mer, with the core sequence being STNAGRRQK (SEQ ID NO:23). Binding was stronger with the sequence CPSCD was also present and strongest binding was observed when the sequences IKKLK, CPSCD and STNAGRRQK were present. Strongest binding was observed with peptide 3 comprising the sequence IKKLKRKPPSTNAGRRQKHRLTCPSCDSYE (SEQ ID NO:4) (Summarized in FIG. 10). When pre-incubating 2P2 with peptide 3, 2P2 failed to bind to full length hIL-21 (FIG. 11A). Pre-incubating control antibody 3A3 with peptide 3 did not inhibit binding to full length hIL-21 (FIG. 11B). This demonstrated that epitope consisting in peptide 3 is sufficient for the binding of 2P2 to hIL-21.

Example 8 Binding Affinity of 2P2 to hIL-21

Surface Plasma Resonance binding kinetics assay were performed on a Bio-rad XPR36 system by the direct amine coupling method. Briefly, a flow of mixture of EDC [N-ethyl-N'-(3-diethylamino-propyl) carbodiimide] and NHS (N-hydroxysuccinimide) was used to activate the cell surface of a GLC sensor chip before 25 µg/ml anti-IL-21 mAb was flowed through, then a shot flow of ethanolamine was used to block the remaining active sites on the cell surface. Afterwards, serial diluted solutions of IL-21 from 0 to 40 nM were flown over the cell surface to bind to the immobilized anti-IL-21 mAb molecules. Binding kinetics were performed at 25° C. with a flow rate of 30 µL/min, association time of 3 min and dissociation time of 6 min. The buffer consisted of Hepes, NaCl, tween20, and 1 mg/mL BSA at pH 7.4. The flow cell regeneration buffer between cycles was 15 mM phosphoric acid. Double references were used to process the sensorgrams. The binding curves were globally fit to the 1:1 Langmuir binding model.

The final binding affinity of 2P2 with hIL-21 was calculated as 3.0E-09 M from the average of n=5 measurements (table 6). The affinity of hIL-21 and 2P2 range from $2.47 \times 10^{-9}$ to $4.29 \times 10^{-9}$, with an average of $3.33 \times 10^{-9}$ and a SD of $0.74 \times 10^{-9}$.

TABLE 6

| Dissociation constant hIL-21/2P2 complex | |
|---|---|
| Complex/well number | KD (M) |
| IL-21/2P2 well 1 | $3.83 \times 10^{-9}$ |
| IL-21/2P2 well 2 | $3.29 \times 10^{-9}$ |
| IL-21/2P2 well 3 | $2.79 \times 10^{-9}$ |
| IL-21/2P2 well 4 | $4.29 \times 10^{-9}$ |
| IL-21/2P2 well 5 | $2.47 \times 10^{-9}$ |

Example 9 Humanisation of 2P2

Humanized 2P2 (h2P2) mAbs were generated by transferring the CDRs of the 2P2 mAb (CDR-H1; CDR-H2; CDR-H3; CDR-L1; CDR-L2; and CDR-L3) onto human framework regions using standard molecular techniques. IMGT/V-QUEST and IMGT/Junctions analysis tools were used to identify human germline genes in which sequences from the variable regions of both the heavy and light chains were closely aligned with those of murine antibody. Framework sequences of these selected human germline genes were used as acceptor sequences for the mouse 2P2 CDRs (IGHV3-48*02 and IGKV2-28*01 human genes according to IMGT database). However, murine residues were retained in the critical "Vernier" zone. The humanized VH and VL genes, which were also codon optimized for expressed in CHO cells, were synthesized by Genescript.

Example 10 Confirmation of Ability of Humanised 2P2 to Enhance IL-21

Figure 12:
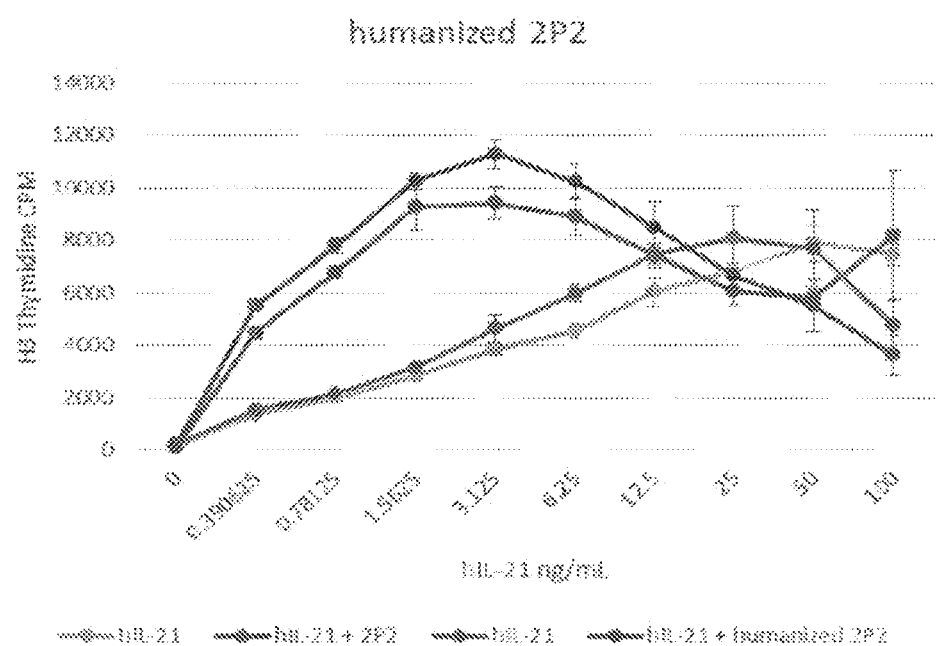
FIG. 12 shows that humanized 2P2 antibody retains the ability to enhance IL-21 activity as the murine 2P2 antibody. BAF3 mouse cell line was transduced to express human IL-21 receptor, BAF3-hIL21R cells, proliferate and incorporate H3 Thymidine in response to hIL-21. 2P2 (A) and human-2P2 (B) enhance hIL-21 to a similar extent (overlay (c)).

To confirm that the h2P2 had the same ability to enhance hIL-21 as murine 2P2, BAF3 mouse cell line was transduced to express human IL-21 receptor (BAF3-hIL21R). BAF3-hIL21R cells proliferate and incorporate H3 Thymidine in response to hIL-21. Murine 2P2 antibody enhances hIL-21 mediated H3 Thymidine incorporation (FIG. 12(*a*) where the murine 2P2 antibody is indicated as the 'original 2P2') indicating a potentiation of hIL-21 mediated cell proliferation. Humanised-2P2 also enhances hIL-21 mediated H3 Thymidine incorporation (FIG. 12(*b*). Overlay of the results with murine 2P2 and humanized 2P2 (FIG. 12(*c*)) reveal that the humanization process outlined in Example 9 did not affect the function of the 2P2 antibody and that the humanized 2P2 antibody retains the ability to enhance the activity of IL-21.

Figure 15:
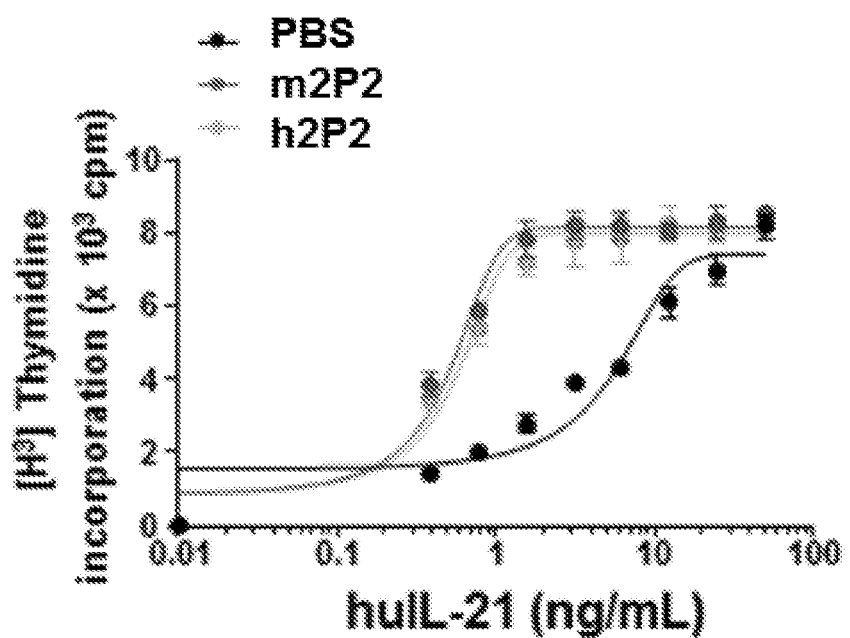
FIG. 15 shows additional H3 Thymidine incorporation assay with h2P2 and m2P2 displaying similarly high potency to enhance IL-21 activity.

Further experimental data is shown in FIG. 15. Starved hIL-21R-BAF3 overnight. Culture hIL-21R-BAF3 cells with increasing concentrations of hIL-21+10 ug or mouse 2P2 (m2P2) or humanized 2P2 (h2P2). Culture for 4 days. Add 1 uCi of Thymidine, incubate for another 16 hours. Harvest and read plates.

Example 11 Confirmation of Ability of Humanised 2P2 to Bind with High Affinity to hIL-21

Wells of 96-well Maxisorb Immuno plates (Nunc, Roskilde, Denmark) were coated with 1 ug/ml of purified hIL-21 in carbonate-coating buffer overnight at 4 degree C. Wells were blocked with 200 ml of 5% MPBS for 2 h at 37 degree C. Serial dilutions of the original mouse mAb 2P2 (m2P2)

and the humanized 2P2 (h2P2) purified antibodies were incubated in wells with hIL-21. After washing, a ½000 dilution of anti-mouse IgG HRP-conjugate or anti-human IgG HRP-conjugate was added to each well and incubated for a further 1 h at RT. The substrate TMB was added and absorbance was read at 405 nm. Data are plotted as a mean+/−SD.

Figure 13:
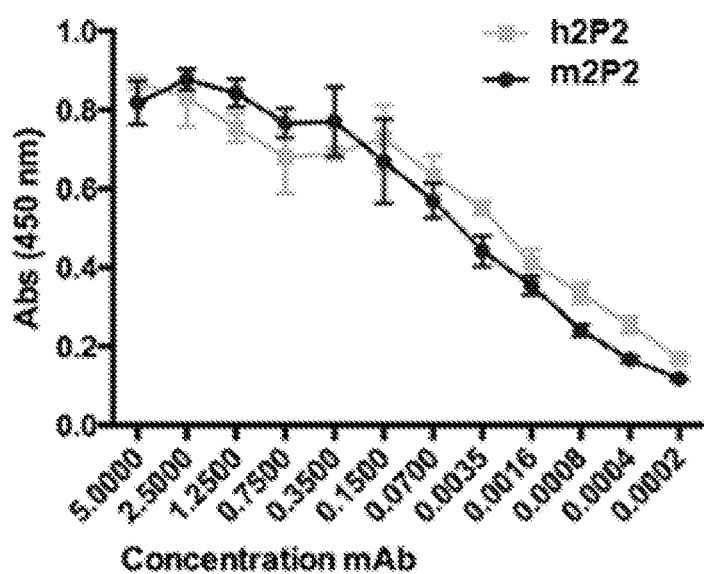
FIG. 13 shows comparable binding of the humanized 2P2 antibody (h2P2) and the original murine 2P2 antibody (m2P2).

FIG. 13 shows that the humanized 2P2 antibody binds to human IL-21 with equivalent affinity to the original murine 2P2 antibody.

Surface plasma resonance (SPR) data showed high binding affinity of mouse 2P2 and its humanised counterpart (denoted as humanised 2P2) to the antigen human IL-21. The kinetics of the interactions were also displayed as well as the binding affinities in Table 7. Triplicates SPR measurements were conducted on ProtOn XPR36 (Bio-rad). NLC chips (Bio-rad) were used to immobilise biotinylated hIL21 on ligand channels, followed by flowing through of various concentrations of mouse 2P2 or humanised 2P2.

Figure 14:
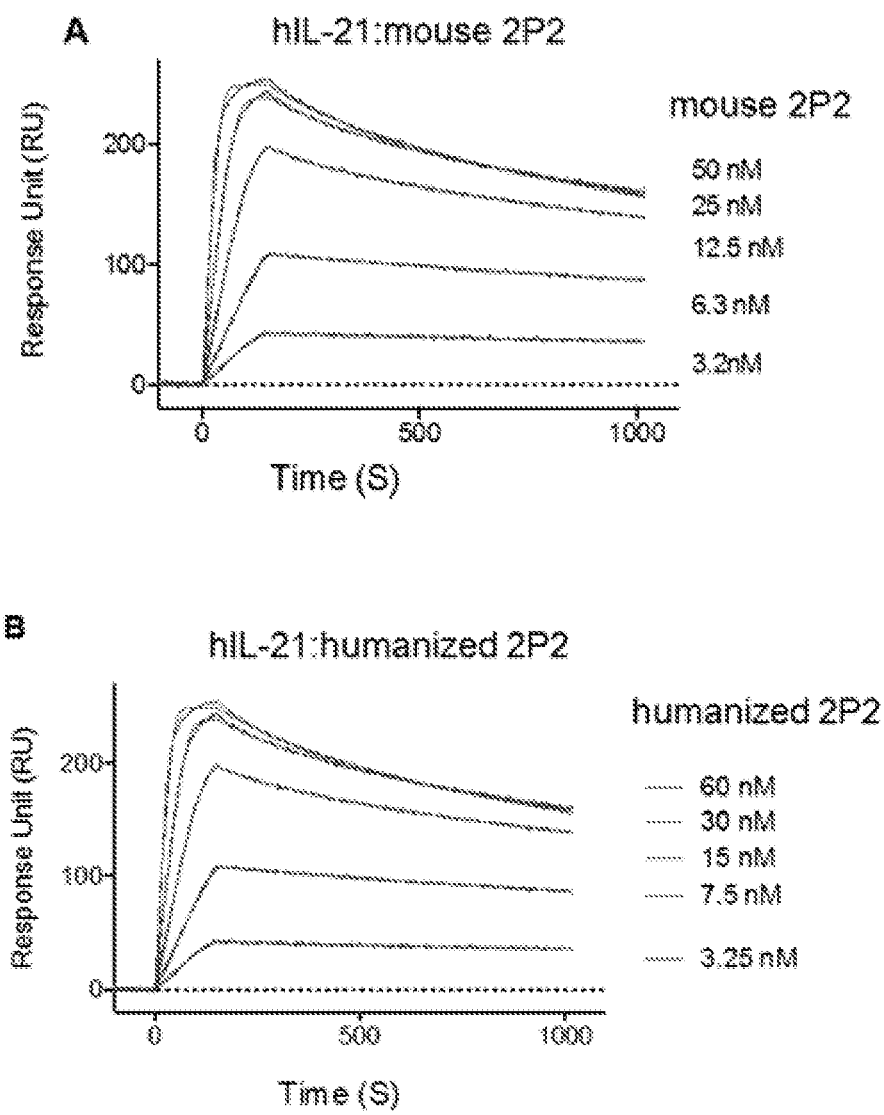
FIG. 14 shows surface plasma resonance (SPR) data of high binding affinity of mouse 2P2 and its humanised counterpart (denoted as humanised 2P2) to the antigen human IL-21.

FIG. 14 shows near equivalent binding kinetics and dissociation constants for mouse 2P2 and the humanized 2P2.

TABLE 7

On and off-rates and dissociation constant of mouse and humanized 2P2

|  | Kon(1/s) | Koff(1/s) | KD(M) |
| --- | --- | --- | --- |
| Mouse 2P2 | 2.55E+07 | 5.12E−04 | 2.01E−11 |
| Humanized 2P2 | 1.21E+07 | 3.70E−04 | 3.05E−11 |

The invention claimed is:

1. An IL-21 binding protein comprising an antigen binding domain of an antibody, wherein the antigen binding domain binds to IL-21 and enhances IL-21 activity, and comprises a VH and a VL; wherein:
   (i) the VH comprises FR1-CDR1-FR2-CDR2-FR3-CDR3-FR4,
      wherein the CDR1-3 comprise the amino acid sequences of SEQ ID NO:5-7, respectively; and
      wherein the FR1 comprises a sequence at least 65% identical to SEQ ID NO: 24; the FR2 comprises a sequence at least 80% identical to SEQ ID NO: 25; the FR3 comprises a sequence at least 75% identical to SEQ ID NO: 26; and the FR4 comprises a sequence at least 80% identical to SEQ ID NO: 27; and
   (ii) the VL comprises FR1a-CDR1a-FR2a-CDR2a-FR3a-CDR3a-FR4a,
      wherein the CDR1a-3a comprises the amino acid sequences of SEQ ID NO:8-10, respectively; and
      wherein the FR1a comprises a sequence at least 80% identical to SEQ ID NO: 28, the FR2a comprises a sequence at least 80% identical to SEQ ID NO: 29, the FR3a comprises a sequence at least 80% identical to SEQ ID NO: 30, and the FR4a comprises a sequence at least 80% identical to SEQ ID NO: 31;
   or
   (iii) the VH comprises FR1-CDR1-FR2-CDR2-FR3-CDR3-FR4,
      wherein the CDR1 comprises the amino acid sequence of SEQ ID NO:11; the CDR2 comprises the amino acid sequence of SEQ ID NO:12 or 42; and the CDR3 comprises the amino acid sequence of SEQ ID NO:13; and wherein the FR1 comprises a sequence at least 65% identical to SEQ ID NO: 32; the FR2 comprises a sequence at least 80% identical to SEQ ID NO: 33; the FR3 comprises a sequence at least 75% identical to SEQ ID NO: 34; and the FR4 comprises a sequence at least 80% identical to SEQ ID NO: 35; and (iv) the VL comprises FR1a-CDR1a-FR2a-CDR2a-FR3a-CDR3a-FR4a, wherein the CDR1a comprises the amino acid sequence of SEQ ID NO: 14; the CDR2a comprises the amino acid sequence of SEQ ID NO: 15; and the CDR3a comprises the amino acid sequence of SEQ ID NO: 10 or 16; and wherein the FR1a comprises a sequence at least 80% identical to SEQ ID NO: 36; the FR2a comprises a sequence at least 80% identical to SEQ ID NO: 37; the FR3a comprises a sequence at least 80% identical to SEQ ID NO: 38; and the FR4a comprises a sequence at least 80% identical to SEQ ID NO: 39.

2. The IL-21 binding protein according to claim 1, wherein the FRs comprise each of the sequences set forth in SEQ ID NOs: 24 to 31.

3. The IL-21 binding protein according to claim 1, wherein the FRs comprise each of the sequences set forth in SEQ ID NOs: 32 to 39.

4. The IL-21 binding protein according to claim 1, wherein the antigen binding domain comprises the VH comprising the amino acid sequence of SEQ ID NO: 40 and the VL comprising the amino acid sequence of SEQ ID NO: 41.

5. The IL-21 binding protein according to claim 1 wherein the antigen binding domain binds to an epitope of IL-21, wherein the epitope comprises the amino acid sequence of SEQ ID NO: 23.

6. A pharmaceutical composition comprising the IL-21 binding protein of claim 1 and a pharmaceutically acceptance diluent, excipient, or carrier.

7. A method of treating a viral infection or cancer in a subject in need thereof, the method comprising administering the IL-21 binding protein according to claim 1.

8. The method of claim 7, wherein the IL-21 binding protein is administered in combination with one or more immunotherapeutic compounds, selected from a checkpoint inhibitor, tyrosine kinase inhibitor, cytokine or interleukin; interferon; granulocyte macrophage colony stimulating factor; cancer vaccine, infectious disease vaccine; antiviral drug or an oncolytic virus.

* * * * *